(12) United States Patent
Arbabi Ghahroudi et al.

(10) Patent No.: US 9,926,363 B2
(45) Date of Patent: Mar. 27, 2018

(54) ANTI-CAMPYLOBACTER JEJUNI ANTIBODIES AND USES THEREFOR

(71) Applicant: NATIONAL RESEARCH COUNCIL OF CANADA, Ottawa (CA)

(72) Inventors: Mehdi Arbabi Ghahroudi, Ottawa (CA); Ali Riazi, Thornhill (CA); Christine M. Szymanski, Edmonton (CA); Greg Hussack, Ottawa (CA); Jamshid Tanha, Ottawa (CA); Roger MacKenzie, Ottawa (CA)

(73) Assignee: National Research Council of Canada, Ottawa, Ontario ( * ) Notice: Subject to any disclaimer, the term of this patent is extended or adjusted under 35 U.S.C. 154(b) by 0 days.

(21) Appl. No.: 14/438,412

(22) PCT Filed: Oct. 24, 2013

(86) PCT No.: PCT/CA2013/050806
§ 371 (c)(1),
(2) Date: Apr. 24, 2015

(87) PCT Pub. No.: WO2014/063253
PCT Pub. Date: May 1, 2014

(65) Prior Publication Data
US 2015/0307597 A1    Oct. 29, 2015

Related U.S. Application Data

(60) Provisional application No. 61/718,062, filed on Oct. 24, 2012.

(51) Int. Cl.
| | | |
|---|---|---|
| C07K 16/12 | (2006.01) | |
| A61K 39/40 | (2006.01) | |
| G01N 33/569 | (2006.01) | |
| A61K 45/06 | (2006.01) | |
| A61K 39/00 | (2006.01) | |

(52) U.S. Cl.
CPC .......... *C07K 16/121* (2013.01); *A61K 39/40* (2013.01); *A61K 45/06* (2013.01); *G01N 33/56922* (2013.01); *A61K 2039/505* (2013.01); *C07K 2317/22* (2013.01); *C07K 2317/35* (2013.01); *C07K 2317/565* (2013.01); *C07K 2317/569* (2013.01); *C07K 2317/92* (2013.01); *G01N 2333/205* (2013.01); *G01N 2469/10* (2013.01)

(58) Field of Classification Search
None
See application file for complete search history.

(56) References Cited

U.S. PATENT DOCUMENTS

| | | |
|---|---|---|
| 6,551,599 B2 | 4/2003 | Mandrell et al. |
| 8,173,130 B2 | 5/2012 | Salzman et al. |
| 2009/0208506 A1 | 8/2009 | Rachamim et al. |
| 2010/0239583 A1 | 9/2010 | Murthy et al. |

OTHER PUBLICATIONS

Newell 1986 (Monoclonal antibodies directed against the flagella of Campylobacter jejuni: cross-reacting and serotypic specificity and potential use in diagnosis; Journal of Hygiene 96(3):377-384).*
Greenspan et al. 1999 (Defining epitopes: It's not as easy as it seems; Nature Biotechnology, 17:936-937).*
Sela-Culang et al. 2013 (The structural basis of antibody-antigen recognition; Frontiers in Immunology 4(302):1-13).*
Alfredson D.A. et al., 2007. Antibiotic resistance and resistance mechanisms in Campylobacter jejuni and Campylobacter coli-Review. FEMS Microbiol Lett. 277(2): 123-32.
Blaser MJ, et al., 1986. Extraintestinal Campylobacter jejuni and Campylobacter coli infections: host factors and strain characteristics. J. Infect. Dis. 153:552-559.
Blaser MJ., 1997. Epidemiologic and clinical features of Campylobacter jejuni infections. J. Infect. Dis. suppl. 2: S103-105.
Boyd Y. et al., 2005. Host genes affect intestinal colonisation of newly hatched chickens by Campylobacter jejuni. Immunogenetics, 57, 248-53.
Burr et al., 1988. Mucosal and systemic immunity to Campylobacter jejuni in rabbits after gastric inoculation. Infect Immun. 1988: 56(1):99-105.
Buzby JC, et al., 1997. The economic burden of Campylobacter-associated Guillain-Barre syndrome. J Infect Dis.176 Suppl 2:S192-7.
Carrillo C, et al., 2005. Bacteriophage therapy to reduce Campylobacter jejuni colonization of broiler chickens. Appl Environ Microbiol. 71 (11):6554-63.
Casadevall A. et al., Passive antibody therapy for infectious diseases. Nat Rev Microbiol-Review. Sep. 2004;2(9):695-703.
Castillo S.L. et al., 2011. Extracts of edible and medicinal plants in inhibition of growth, adherence, and cytotoxin production of Campylobacter jejuni and Campylobacter coli. J Food Sci. 76(6): M421-6.
Cawthraw S.A. et al., 2000. Antibodies, directed towards Campylobacter jejuni antigens, in sera from poultry abattoir workers. Clin Exp Immunol. 122(1):55-60.

(Continued)

*Primary Examiner* — Mary Lyons
(74) *Attorney, Agent, or Firm* — Roula Thomas

(57) ABSTRACT

*Campylobacter jejuni* is a leading cause of bacterial food-borne diseases in humans, ranging from acute diarrheal disease to neurological disorders. An isolated or purified antibody or fragment thereof specific to *C. jejuni* is described. The antibody or fragment thereof binds to a flagellar protein and reduces motility of *C. jejuni*. The antibody or fragment thereof is derived from a heavy chain IgG variable domain fragment ($V_HH$) of a camelid animal immunized with *C. jejuni* flagellar protein. A multivalent form, as well as a phage format, of the antibody or fragment thereof is described. Methods of reducing presence of *C. jejuni* in an animal or an animal environment, methods and formulations for treating *C. jejuni* infection, and method of detecting *C. jejuni* are also described.

15 Claims, 15 Drawing Sheets

(56) References Cited

OTHER PUBLICATIONS

Clark J.D. et al., 2012. Eimeria species parasites as novel vaccine delivery vectors: anti- Campylobacter jejuni protective immunity induced by Eimeria tenella-delivered CjaA. Vaccine. 30(16):2683-8.
De Los Santos F. et al., 2009. The natural feed additive caprylic acid decreases Campylobacter jejuni colonization in market-aged broiler chickens. Poult Sci. 88(1):61-4.
De Zoete M.R. et al., 2007. Vaccination of chickens against Campylobacter. Vaccine, 25, 5548-57.
Dolby JM et al., 1986. The protection of infant mice from colonization with Campylobacter jejuni by vaccination of the dams. J Hyg (Lond). 1986: 96(2): 143-51.
El-Shibiny A et al., 2009. Application of a group II Campylobacter bacteriophage to reduce strains of Campylobacter jejuni and Campylobacter coli colonizing broiler chickens. J Food Prot. 72(4):733-40.
European Food Safety Authority (EFSA). Scientific Opinion on Campylobacter in broiler meat production: controloptions and performance objectives and/or targets at different stages of the food chain. 201 1. EFSA Journal.9 (4) 2105: 1-141.
Gellynck X et al., 2008. Economics of reducing Campylobacter at different levels within the Belgian poultry meat chain.J Food Prot. 71 (3):479-85.
Hariharan H. et al., 2004. Campylobacter jejuni: Public health hazards and potential control methods in poultry: a review. Vet. Med.—Czech, 49: 441-446.
Hermans D. et al., 2011, Poultry as a host for the zoonotic pathogen Campylobacter jejuni. Review Vector Borne Zoonotic Dis. Feb. 2012; 12(2):89-98.
Kaiser, P. et al., 2009, Towards the selection of chickens resistant to Salmonella and Campylobacter infections. Bull Mem Acad R Med Belg, 164, 17-25; discussion 25-6.
Layton S.L. et al., Evaluation of Salmonella-vectored Campylobacter peptide epitopes for reduction of Campylobacter jejuni in broiler chickens. Clin Vaccine Immunol. Mar. 2011; 18(3):449-54.
Lin J. 2009. Novel approaches for Campylobacter control in poultry-review. Foodborne Pathog Dis. 6(7):755-65.
Luangtongkum T et al., 2009. Antibiotic resistance in Campylobacter: emergence, transmission and persistence-Review. Future Microbiol. 4(2): 189-200.
Man SM. 2011 The clinical importance of emerging Campylobacter species. Nat Rev Gastroenterol Hepatol. 25;8(12):669-85.
Messaoudi S. et al., 2011, Identification of lactobacilli residing in chicken ceca with antagonism against Campylobacter. Int Microbiol. 14(2): 103-10.
Newell DG, Fearnley C. 2003. Sources of Campylobacter colonization in broiler chickens. Appl Environ Microbiol. 69(8):4343-51.
Nurmi E., and Rantala M. 1973. New aspects of *Salmonella* infection in broiler production. Nature. 241(5386) :210-1.
Nyachuba DG. 2010 Foodborne illness: is it on the rise? Nutr Rev. 68(5):257-69.
Pavlovskis OR, et al., 1991. Significance of flagella in colonization resistance of rabbits immunized with *Campylobacter* spp. Infect Immun. 59(7):2259-64.
Rollwagen FM et al., Killed Campylobacter elicits immune response and protection when administered with an oral adjuvant. Vaccine 1993. 11 (13): 1316-20.
Sahin O, et al., 2003. Effect of Campylobacter-specific maternal antibodies on Campylobacter jejuni colonization in young chickens. Appl Environ Microbiol. 69(9): 5372-9.
Santini C, et al., 2010. Characterization of probiotic strains: an application as feed additives in poultry against Campylobacter jejuni. Int J Food Microbiol. 141 Suppl 1 :S98-108.
Silva J, et al., 2011, *Campylobacter* spp. as a Foodborne Pathogen: A Review. Front Microbiol. 2:200: 1-12.
Smith, J.L. et al., 2010. Fluoroquinolone resistance in campylobacter-review. J Food Prot. Jun. 2010;73(6):1 141-52.
Stern N.J., et al., 1990. Influence of antibody treatment of Campylobacter jejuni on the dose required to colonize chicks. Avian Dis. 34(3):595-601.
Stern N.J. et al., 2003. Enumeration of *Campylobacter* spp. in broiler feces and in corresponding processed carcasses. J Food Prot. 66(9): 1557-63.
Svetoch E.A. and Stern N.J. (2010) Bacteriocins to control *Campylobacter* spp. in poultry—A review. Poult Sci. 89(8): 1763-8. Review.
Ueki Y et al., (1987) Protection against Campylobacter jejuni infection in suckling mice by anti-flagellar antibody. Microbiol Immunol 31 : 1161-1171.
Wagenaar J.A. et al., 2008. Poultry colonization with Campylobacter and its control at the primary productionlevel. In: Campylobacter, 3rd edition. Navhamkin I., Szymanski CM. and Blaser M.J. (eds.). Washington, DC: American Society for Microbiology, 2008, pp. 667-678.
Willis W.L., and Reid L. 2008. Investigating the effects of dietary probiotic feeding regimens on broiler chicken production and Campylobacter jejuni presence. Poult Sci. 87(4):606-11.
Zeng X. et al., 2010. Development and Evaluation of CmeC Subunit Vaccine against Campylobacter jejuni. J Vaccines Vaccin. 1 (3): 1-21.
Zhang G. et al., 2007. Potential competitive exclusion bacteria from poultry inhibitory to Campylobacter jejuni and *Salmonella*. J Food Prot. 70(4): 867-73.
Young T.K. et al., Campylobacter jejuni: molecular biology and pathogenesis, Nature Reviews Microbiology, 2007, vol. 5, No. 9, pp. 665-679.
Written Opinion for corresponding PCT application No. PCT/CA2013/050806 dated Jan. 21, 2014.
International Search Report for corresponding PCT application No. PCT/CA2013/050806 dated Jan. 21, 2014.
Wagenaar J.A., et al., 2005, Phage therapy reduces campylobacter jejuni colonization in broilers, Vet Microbiol, 109, 275-283.
Wagenaar J.A., et al., 2006, Campylobacter in primary animal production and control strategies to reduce the burden of human campylobacteriosis, Rev Sci Tech 25(2), 581-94.
Hermans D. et al., Intestinal mucus protects campylobacter jejuni in the ceca of colonized broiler chickens against the bactericidal effects of medium-chain fatty acids; Poutl Sci 89(6): 114-55.

* cited by examiner

```
FlagV1M          QVKLEESGGGLVQAGGSRRLSCATSGLTFRNFHMAWFRQVAGKEREVVAAISWSRDRQYY 60
FlagV1F23M       QVQLVESGGGLVQAGGSRRLSCATSGLTFRNFHMAWFRQVAGKEREVVAAISWSRDRQYY 60
FlagV1MDSB       QVKLEESGGGLVQAGGSRRLSCATSGLTFRNFHMAWFRQVAGKEREVVCAISWSRDRQYY 60
FlagV1F23MDSB    QVQLVESGGGLVQAGGSRRLSCATSGLTFRNFHMAWFRQVAGKEREVVCAISWSRDRQYY 60
                 **:* *******************************************.**********

FlagV1M          PDPVKGRFTITRDNAKNTVYLQMNSLKPEDTAVYYCAARTASASGDWYKGSYQYWGQGTQ 120
FlagV1F23M       PDPVKGRFTITRDNAKNTVYLQMNSLKPEDTAVYYCAARTASASGDWYKGSYQYWGQGTQ 120
FlagV1MDSB       PDPVKGRFTCTRDNAKNTVYLQMNSLKPEDTAVYYCAARTASASGDWYKGSYQYWGQGTQ 120
FlagV1F23MDSB    PDPVKGRFTCTRDNAKNTVYLQMNSLKPEDTAVYYCAARTASASGDWYKGSYQYWGQGTQ 120
                 ********* **************************************************

FlagV1M          VTVSS 125    SEQ ID NO:8
FlagV1F23M       VTVSS 125    SEQ ID NO:9
FlagV1MDSB       VTVSS 125    SEQ ID NO:30
FlagV1F23MDSB    VTVSS 125    SEQ ID NO:31
                 *****

FlagV6M          QVKLEESGGGLVQAGGSLRVSCTASVSTFSINALGWYRQAPGKARELVAAIGSDGTVYYT 60
FlagV6F23M       QVQLVESGGGLVQAGGSLRVSCTASVSTFSINALGWYRQAPGKARELVAAIGSDGTVYYT 60
FlagV6MDSB       QVKLEESGGGLVQAGGSLRVSCTASVSTFSINALGWYRQAPGKARELVCAIGSDGTVYYT 60
FlagV6F23MDSB    QVQLVESGGGLVQAGGSLRVSCTASVSTFSINALGWYRQAPGKARELVCAIGSDGTVYYT 60
                 **:* *******************************************.**********

FlagV6M          DSVKGRFTISRDNAKNTVSLQMSSLKPEDTAVYYCNAAGKRIGSDGSIWFAVASFGSWGQ 120
FlagV6F23M       DSVKGRFTISRDNAKNTVSLQMSSLKPEDTAVYYCNAAGKRIGSDGSIWFAVASFGSWGQ 120
FlagV6MDSB       DSVKGRFTCSRDNAKNTVSLQMSSLKPEDTAVYYCNAAGKRIGSDGSIWFAVASFGSWGQ 120
FlagV6F23MDSB    DSVKGRFTCSRDNAKNTVSLQMSSLKPEDTAVYYCNAAGKRIGSDGSIWFAVASFGSWGQ 120
                 ******** ***************************************************

FlagV6M          GTQVTVSS 128    SEQ ID NO:13
FlagV6F23M       GTQVTVSS 128    SEQ ID NO:14
FlagV6MDSB       GTQVTVSS 128    SEQ ID NO:32
FlagV6F23MDSB    GTQVTVSS 128    SEQ ID NO:33
                 ********

FlagV1P          QVKLEESGGGLVQAGGSRRLSCATSGLTFRNFHMAWFRQVAGKEREVVAAISWSRDRQYY 60
FlagV6P          QVKLEESGGGLVQAGGSLRVSCTASVSTFSINALGWYRQAPGKARELVAAIG-SDGTVYY 59
                 ***************** *:**::*  **     :.*:**..** **:****. *  **

FlagV1P          PDPVKGRFTITRDNAKNTVYLQMNSLKPEDTAVYYCAAR---TASASGDWYK-GSYQYWG 116
FlagV6P          TDSVKGRFTISRDNAKNTVSLQMSSLKPEDTAVYYCNAAGKRIGSDGSIWFAVASFGSWG 119
                 .*.*******:******* ***.************ *       .*  .*: .*:  **

FlagV1P          QGTQVTVSSGPGGGSGGGSTPDCVTGKVEYTKYNDEDTFTVKVGDKELFTNRANLQSLL 176
FlagV6P          QGTQVTVSSGPGGGSGGGSTPDCVTGKVEYTKYNDEDTFTVKVGDKELFTNRANLQSLL 179
                 ***********************************************************

FlagV1P          LSAQITGMTVTIKTNACHNGGGFSEVIFR 205    SEQ ID NO:19
FlagV6P          LSAQITGMTVTIKTNACHNGGGFSEVIFR 208    SEQ ID NO:21
                 ****************************
```

FIG. 1

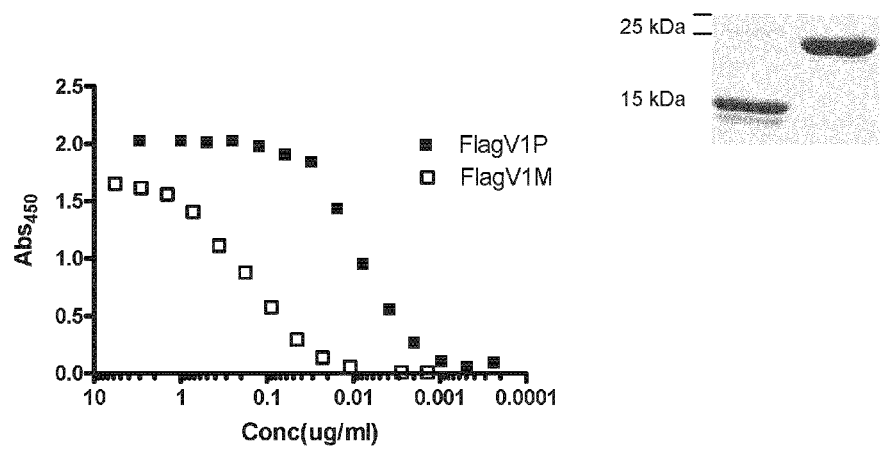
FIG. 2
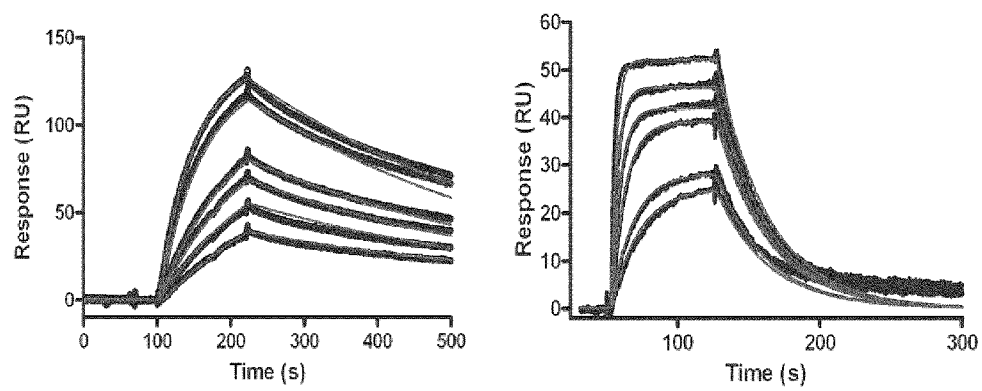
FIG. 3A
FIG. 3B

ANTI-CAMPYLOBACTER JEJUNI ANTIBODIES AND USES THEREFOR

CROSS REFERENCE TO RELATED APPLICATIONS

This application is a national phase entry of International Patent Application No. PCT/CA2013/050806 filed Oct. 24, 2013, and claims the benefit of U.S. Provisional Patent Application U.S. Ser. No. 61/718,062 filed Oct. 24, 2012, the entire contents of both are herein incorporated by reference.

FIELD

The present disclosure relates generally to antibodies, fragments thereof, and to derivatives and applications of such proteins. The antibodies and fragments described are directed against flagellar proteins of C. jejuni.

BACKGROUND

The Campylobacter genus encompasses a large number of morphologically diverse groups (spiral, curved or rod shaped) of bacteria with over 35 species and subspecies reported, 20 of which are found to be either pathogenic to humans causing enteric and extraintestinal illnesses or to colonize a diverse number of sites in humans. (Man, 2011).

Campylobacter jejuni, a Gram negative spiral bacterium, is currently one of the most prevalent food-borne pathogens and a leading cause of bacterial gastroenteritis in humans worldwide. In North America, campylobacteriosis outnumbers the reported cases of illnesses caused by Salmonella, Shigella, Listeria and E. coli combined (Stern & Robach, 2003; Newell et al., 2003; Blaser, 1997). Despite relatively mild diarrheal illness, Campylobacter infection has been associated with severe long-term complications, including: Guillain-Barré Syndrome (GBS), the leading cause of paralysis since the eradication of polio; the non-paralytic variant Miller Fisher syndrome (Humphery et al. 2007; Hariharan et al. 2004; Blaser et al. 1986); reactive arthritis (ReA); and inflammatory bowel disease (IBD) (Rautelin et al. 2000; Gellynck et al. 2008).

It is estimated that between 50-80% of human campylobacteriosis cases can be attributed to chicken consumption, and therefore broiler chicken meat is considered the primary vector for transmitting the pathogen to humans (EFSA Journal 2011; Hermans et al. 2011). Control and reduction of Campylobacter levels in poultry, and chickens in particular, could improve poultry product safety and decrease the incidence of Campylobacter-induced gastroenteritis. Thus, long term complications in humans could be reduced, resulting in saving of tens of billions dollars in hospitalization and other associated costs around the world (EFSA report, 2011; Nyachuba, 2010; Buzby et al. 1997).

Current intervention strategies against C. jejuni and other less frequent strains (e.g., C. coli and C. lari) are applied at various stages of production, including during poultry breeding (primary interventions), during meat production and/or during meat processing. The most accepted strategy is to prevent Campylobacter spp. from entering the flock by installing hygiene barriers and fly screens, the use of high quality water, reduction of slaughter age and discontinued thinning (Newell & Wagenaar, 2000; Wagenaar et al., 2006, 2008; Lin 2009; EFSA report, 2011). However, the susceptibility of chickens to infection by C. jejuni and its ubiquity in the environment have negatively impacted the success of these biosecurity approaches, highlighting the need for alternative approaches by which the bacterial infection can be controlled or eliminated. A reduction in cecal campylobacter levels of 0.5-5 $\log_{10}$ CFU/g has been reported for administration of bacteriophages to chickens as a feed-additive or veterinary drug (El-Shibiny et al., 2009; Carrillo et al., 2005; Wagenaar et al., 2005).

More effectively, treatment with bacteriocins added to poultry drinking water completely eliminated the pathogen in 90% of cases or reduced its levels by $10^6$ fold or more (Svetoch et al., 2010). Other biological reagents such as probiotics (Santini et al., 2010; Willis et al., 2008) and plant bioactive compounds (Castillo et al., 2011; Kureckci et al., 2012) have also been used as food or water additives and shown to significantly reduce the campylobacter loads in chicken feces. The bactericidal effects of probiotic strains such as lactic acid bacteria (LAB) against C. jejuni have been attributed to the production of organic acids, bacteriocin or bacteriocin-like substances (Santini et al., 2010; Messaoudi et al., 2011). Many of these approaches have not been widely adopted in the field because of issues such as efficacy, safety, toxicity, scale-up of production and purification, and the development of campylobacter resistance.

Antibiotics such as fluoroquinolone and macrolides have been approved for the treatment of Campylobacter spp. in both poultry and humans. However, their prolonged use in human and animal health has led to a rapid increase of resistant campylobacter strains in many countries around the world and their use is no longer recommended in animal feed stocks (Smith et al., 2010; Luangtongkum et al., 2009; Alfredson et al., 2007; Silva et al., 2011). Medium chain fatty acids (e.g., caprylic acid) and monoacyl glycerols are alternatives to antibiotics and have been used as feed and water additives to control or eliminate the campylobacter loads in chickens (de los Santos et al., 2009; Hermans et al., 2010, Molatova et al., 2010). Nonetheless, data related to the numbers and prevalence of Campylobacter upon treatment with chemical compounds is inconsistent and no clear conclusion could be made on their effectiveness (The EFSA Journal, 2011). Antibiotic therapy including the use of virginiamycin, erythromycin, neomycin or ciprofloxacin to reduce or eliminate the source of infection in poultry or to treat human infection is a useful tool. However, a growing concern regarding wide-spread use of antibiotic treatment in animal production is the development of resistant Campylobacter strains and the fact that antibiotic-resistant Campylobacter from chickens might cause antibiotic-resistant infections in humans.

Vaccination against a large number of infectious diseases is widely used in commercially reared chickens (Clark et al., 2012). Vaccination of poultry for protection against Campylobacter spp. colonization has also been extensively studied. However, identification of a cross-reactive vaccinal target capable of eliciting a rapid and strong immune response over a short period of time (3-4 weeks) coupled with the need for novel adjuvants are some of the challenges to be overcome (de Zoete et al., 2007; Layton et al., 2011; Zeng et al., 2010; Clark et al., 2012). Consequently, no commercial vaccine against C. jejuni is currently available.

A competitive exclusion (CE) approach, first described by Nurmi and Rantala (1973), is based on the establishment of a protective enteric flora using defined or undefined microorganisms from the guts of healthy chickens to prevent campylobacter from occupying its specific niche, especially the cecum (Zhang et al., 2007; Chen, 2001; Stern, 2001). Difficulties in applying the CE approach include a lack of standardization in identifying the complex species in CE products as well as limited and variable success rates in reducing *campylobacter* infections (Lin, 2009; EFSA Journal 2011).

Lastly, it has been suggested that the susceptibility or resistance of chickens to *Campylobacter* spp. is dependent on the hosts' genetic system and involves both non-immune and immune mechanisms (Kaiser et al., 2009). Therefore, selective breeding would be a method of choice to expand the genetically inherited resistant chicken lines. In this regard, a 10-100 fold difference in *Campylobacter* spp. colonization was observed between four inbred chicken lines and the inherited resistance pattern was consistent with single autosomal dominant locus (Boyd et al., 2005). Establishment of resistant chicken lines while preserving meat or egg production and quality, is, however, a time-consuming process with unpredictable results. To date, none of the above-mentioned experimental interventions has been modeled or applied at the field level and, therefore, none has been successfully commercialized.

Antibodies were originally recognized as effective antimicrobial reagents by Behring and Kitasato in the early 1890s (Behring & Kitasato, 1890; Casadevall et al., 2004) and since then, serum therapy became an effective strategy to combat many infectious diseases. The presence of specific antibodies in the serum or intestinal secretions has been associated with resistance of rabbits (Burr et al., 1988; Pavlovskis et al., 1991; Rollwagen et al., 1993) and mice (Dolby & Newell 1986; Rollwagen et al., 1993) to colonization by *C. jejuni*. In young chickens (less than 2-3 weeks old), the presence of maternal antibodies against *Campylobacter* spp. delays the onset of colonization and reduces the rate of horizontal spread of *C. jejuni* in the flock (Sahin et al., 2003), suggesting that passive immunotherapy using anti-*Campylobacter* spp. antibodies could be an attractive approach for interfering with bacterial colonization in chickens. Indeed, passive immunization with anti-flagella monoclonal antibodies has already been shown to reduce *C. jejuni* colonization in mice (Ueki et al. 1987). Similarly, the use of hyperimmune anti-*C. jejuni* rabbit serum or anti-*C. jejuni* antibodies appear to be effective in diminishing *C. jejuni* colonization in chickens (Stern et al., 1990). Consistent with this, others have shown that poultry abattoir workers who have high titers of *Campylobacter* spp.-specific IgGs circulating in their blood rarely acquire campylobacteriosis (Cawthraw et al., 2000). Despite all these observations, antibodies as agents for reducing *Campylobacter* loads have not gained market attention largely due to the high cost of manufacturing, sensitivity of conventional antibodies to GI tract proteases, lack of effective GI tract delivery systems, and high antigenic variation among *Campylobacter* spp., which requires multiple antibody preparations to target different strains of *Campylobacter*.

U.S. Pat. No. 8,173,130 (Salzman et al.), U.S. Patent Publication No. 2009/0208506 (Rachamim et al.), and U.S. Patent Publication No. 2010/0239583 (Murthy et al.), describe monoclonal antibodies to flagellin from various Gram-negative bacteria including *Campylobacter*, which can be used to deter bacterial infection, as well as treat or prevent diseases including inflammatory bowel disease. These antibodies share common disadvantages of such molecules including difficulty in engineering, difficulty in and cost of production, and slow tissue penetration when used in vivo. Additionally, mAb and fragments thereof (for example, scFv and Fab) are very sensitive to GI tract proteases, which is disadvantageous when oral administration is desired.

The presence of specific antibodies in the serum or intestinal secretions of rabbits and mice has been associated with a resistance to gastrointestinal tract colonization by *C. jejuni*. Studies in chickens also suggest that active immunization can reduce the level of intestinal infection by *C. jejuni*, but the window of time to obtain a sufficient immune response prior to the early slaughter of chickens, as well as cost and feasibility, make this approach impractical.

Control of *Campylobacter* at source, particularly within poultry farms, would reduce the risk of human exposure to the pathogen and would have a significant impact on food safety and public health. Advantageously, a safer food supply permits a supplier to avoid costly operational shutdowns and product recalls. Reducing environmental exposure, improving biosecurity, competitive exclusion, vaccination, host genetics selection, and antimicrobial or antibiotic strategies including bacteriophage therapy and bacteriocin treatment are beneficial, but there is still a need for improved strategies to reduce *C. jejuni* in the food supply. Innovative approaches to the challenges presented by *Campylobacter jejuni* would be of benefit to the public.

Therefore, there remains a need in the art for a cost-effective method of reducing *C. jejuni* in the food supply; there also remains a need in the art for antibodies that have high affinity but can overcome the shortcomings of IgGs and their variants.

SUMMARY

The present disclosure relates generally to antibodies, fragments thereof, and to derivatives and applications of such proteins. The antibodies and fragments described are directed against flagellar proteins of *C. jejuni*.

Isolated or purified antibodies or fragments thereof are as described herein, together with modifications thereof, including multimeric forms, such as pentabodies. The affinity specificity of the antibodies or fragments thereof for *C. jejuni* flagella is illustrated. The antibodies show efficacy in reducing *C. jejuni* colonization levels in chickens, for example when orally administered. The antibodies disclosed display specific binding to the bacterial flagella. The antibodies and multimers described herein reduce *C. jejuni* motility. Further variants are described with advantageous biophysical properties. Through specific panning efforts and disulfide-bond engineering strategies, antibodies are described which display good thermal stability and protease tolerance or resistance. A hyper-stabilized antibody or fragment thereof is also described, having superior thermal stability and resistance to the major gastrointestinal (GI) proteases.

Thus, the present disclosure provides an isolated or purified antibody or fragment thereof specifically binding to *C. jejuni* flagella, comprising
- a complementarity determining region (CDR) 1 comprising the sequence GLTFRNFHMA (SEQ ID NO:1) or VSTFSINALG (SEQ ID NO:4);
- a CDR2 comprising the sequence ISWSRDRQ (SEQ ID NO:2) or IGSDGTV (SEQ ID NO:5); and
- a CDR3 comprising the sequence AARTASASGDWYKGSYQY (SEQ ID NO:3) or NAAGKRIGSDGSIWFAVASFGS (SEQ ID NO:6).

The isolated or purified antibody or fragment thereof as described above may comprise a CDR1 of sequence GLTFRNFHMA (SEQ ID NO:1), a CDR2 of sequence ISWSRDRQ (SEQ ID NO:2), and a CDR3 of sequence AARTASASGDWYKGSYQY (SEQ ID NO:3). More specifically, the isolated or purified antibody or fragment thereof may comprise the sequence:

(SEQ ID NO: 7)
$QVX_1LX_2ESGGGLVQAGGSRRLSCATSGLTFRNFHMAWFRQVAGKEREVV$
$X_3AISWSRDRQYYPDPVKGRFTX_4TRDNAKNTVYLQMNSLKPEDTAVYYC$
AARTASASGDWYKGSYQYWGQGTQVTVSS, where $X_1$=K or Q; $X_2$=E or V; $X_3$=A or C; $X_4$=I or C; or a sequence substantially identical thereto. In a specific, non-limiting example, the isolated or purified antibody or fragment thereof may comprise the sequence:

(SEQ ID NO: 8)
QVKLEESGGGLVQAGGSRRLSCATSGLTFRNFHMAWFRQVAGKEREVVAA

ISWSRDRQYYPDPVKGRFTITRDNAKNTVYLQMNSLKPEDTAVYYCAART

ASASGDWYKGSYQYWGQGTQVTVSS;

(SEQ ID NO: 9)
QVQLVESGGGLVQAGGSRRLSCATSGLTFRNFHMAWFRQVAGKEREVVAA

ISWSRDRQYYPDPVKGRFTITRDNAKNTVYLQMNSLKPEDTAVYYCAART

ASASGDWYKGSYQYWGQGTQVTVSS;

(SEQ ID NO: 10)
QVKLEESGGGLVQAGGSRRLSCATSGLTFRNFHMAWFRQVAGKEREVVCA

ISWSRDRQYYPDPVKGRFTCTRDNAKNTVYLQMNSLKPEDTAVYYCAART

ASASGDWYKGSYQYWGQGTQVTVSS;

(SEQ ID NO: 11)
QVQLVESGGGLVQAGGSRRLSCATSGLTFRNFHMAWFRQVAGKEREVVCA

ISWSRDRQYYPDPVKGRFTCTRDNAKNTVYLQMNSLKPEDTAVYYCAART

ASASGDWYKGSYQYWGQGTQVTVSS;

or a sequence substantially identical thereto.

Alternatively, the isolated or purified antibody or fragment thereof may comprise a CDR1 of sequence VSTFSINALG (SEQ ID NO:4), a CDR2 of sequence IGSDGTV (SEQ ID NO:5), and a CDR3 of sequence NAAGKRIGSDGSIWFAVASFGS (SEQ ID NO:6). More specifically, the isolated or purified antibody or fragment thereof may comprise the sequence:

(SEQ ID NO: 12)
$QVX_1LX_2ESGGGLVQAGGSLRVSCTASVSTFSINALGWYRQAPGKARE$
$LVX_3AIGSDGTVYYTDSVKGRFTX_4SRDNAKNTVSLQMSSLKPEDTAV$
YYCNAAGKRIGSDGSIWFAVASFGSWGQGTQVTVSS, where $X_1$=K or Q; $X_2$=E or V; $X_3$=A or C; $X_4$=I or C; or a sequence substantially identical thereto. In a specific, non-limiting example, the isolated or purified antibody or fragment thereof may comprise the sequence:

(SEQ ID NO: 13)
QVKLEESGGGLVQAGGSLRVSCTASVSTFSINALGWYRQAPGKARELVAA

IGSDGTVYYTDSVKGRFTISRDNAKNTVSLQMSSLKPEDTAVYYCNAAGK

RIGSDGSIWFAVASFGSWGQGTQVTVSS;

-continued (SEQ ID NO: 14)
QVQLVESGGGLVQAGGSLRVSCTASVSTFSINALGWYRQAPGKARELVAA

IGSDGTVYYTDSVKGRFTISRDNAKNTVSLQMSSLKPEDTAVYYCNAAGK

RIGSDGSIWFAVASFGSWGQGTQVTVSS;

(SEQ ID NO: 15)
QVKLEESGGGLVQAGGSLRVSCTASVSTFSINALGWYRQAPGKARELVCA

IGSDGTVYYTDSVKGRFTCSRDNAKNTVSLQMSSLKPEDTAVYYCNAAGK

RIGSDGSIWFAVASFGSWGQGTQVTVSS;

(SEQ ID NO: 16)
QVQLVESGGGLVQAGGSLRVSCTASVSTFSINALGWYRQAPGKARELVCA

IGSDGTVYYTDSVKGRFTCSRDNAKNTVSLQMSSLKPEDTAVYYCNAAGK

RIGSDGSIWFAVASFGSWGQGTQVTVSS;

or a sequence substantially identical thereto.

The isolated or purified antibody or fragment thereof as described herein may specifically bind to flagellin; more specifically, the isolated or purified antibody or fragment thereof may specifically bind to the Fla A component of flagellin.

The isolated or purified antibody or fragment thereof as described above may be a single-domain antibody (sdAb). The sdAb may be of camelid origin.

The isolated or purified antibody or fragment thereof may be provided in a multivalent display. For example, the isolated or purified antibody or fragment thereof may be expressed as a fusion protein with the verotoxin B subunit. The fusion protein may assemble into a pentabody. In a specific, non-limiting example, the multimer may comprise one or more than one fusion protein selected from:

(SEQ ID NO: 19)
QVKLEESGGGLVQAGGSRRLSCATSGLTFRNFHMAWFRQVAGKEREVVAA
ISWSRDRQYYPDPVKGRFTITRDNAKNTVYLQMNSLKPEDTAVYYCAART
ASASGDWYKGSYQYWGQGTQVTVSSGPGGGSGGGGSTPDCVTGKVEYTKY
NDEDTFTVKVGDKELFTNRANLQSLLLSAQITGMTVTIKTNACHNGGGFS
EVIFR;

(SEQ ID NO: 20)
QVQLVESGGGLVQAGGSRRLSCATSGLTFRNFHMAWFRQVAGKEREVVAA
ISWSRDRQYYPDPVKGRFTITRDNAKNTVYLQMNSLKPEDTAVYYCAART
ASASGDWYKGSYQYWGQGTQVTVSSGPGGGSGGGGSTPDCVTGKVEYTKY
NDEDTFTVKVGDKELFTNRANLQSLLLSAQITGMTVTIKTNACHNGGGFS
EVIFR;

(SEQ ID NO: 34)
QVKLEESGGGLVQAGGSRRLSCATSGLTFRNFHMAWFRQVAGKEREVVCA
ISWSRDRQYYPDPVKGRFTCTRDNAKNTVYLQMNSLKPEDTAVYYCAART
ASASGDWYKGSYQYWGQGTQVTVSSGPGGGSGGGGSTPDCVTGKVEYTKY
NDEDTFTVKVGDKELFTNRANLQSLLLSAQITGMTVTIKTNACHNGGGFS
EVIFR;

(SEQ ID NO: 35)
QVQLVESGGGLVQAGGSRRLSCATSGLTFRNFHMAWFRQVAGKEREVVCA
ISWSRDRQYYPDPVKGRFTCTRDNAKNTVYLQMNSLKPEDTAVYYCAART

-continued

ASASGDWYKGSYQYWGQGTQVTVSSGPGGGSGGGGSTPDCVTGKVEYTKY

NDEDTFTVKVGDKELFTNRANLQSLLLSAQITGMTVTIKTNACHNGGGFS

EVIFR;

(SEQ ID NO: 21)
QVKLEESGGGLVQAGGSLRVSCTASVSTFSINALGWYRQAPGKARELVAA

IGSDGTVYYTDSVKGRFTISRDNAKNTVSLQMSSLKPEDTAVYYCNAAGK

RIGSDGSIWFAVASFGSWGQGTQVTVSSGPGGGSGGGGSTPDCVTGKVEY

TKYNDEDTFTVKVGDKELFTNRANLQSLLLSAQITGMTVTIKTNACHNGG

GFSEVIFR;

(SEQ ID NO: 22)
QVQLVESGGGLVQAGGSLRVSCTASVSTFSINALGWYRQAPGKARELVAA

IGSDGTVYYTDSVKGRFTISRDNAKNTVSLQMSSLKPEDTAVYYCNAAGK

RIGSDGSIWFAVASFGSWGQGTQVTVSSGPGGGSGGGGSTPDCVTGKVEY

TKYNDEDTFTVKVGDKELFTNRANLQSLLLSAQITGMTVTIKTNACHNGG

GFSEVIFR;

(SEQ ID NO: 36)
QVKLEESGGGLVQAGGSLRVSCTASVSTFSINALGWYRQAPGKARELVCA

IGSDGTVYYTDSVKGRFTCSRDNAKNTVSLQMSSLKPEDTAVYYCNAAGK

RIGSDGSIWFAVASFGSWGQGTQVTVSSGPGGGSGGGGSTPDCVTGKVEY

TKYNDEDTFTVKVGDKELFTNRANLQSLLLSAQITGMTVTIKTNACHNGG

GFSEVIFR;

(SEQ ID NO: 16)
QVQLVESGGGLVQAGGSLRVSCTASVSTFSINALGWYRQAPGKARELVCA

IGSDGTVYYTDSVKGRFTCSRDNAKNTVSLQMSSLKPEDTAVYYCNAAGK

RIGSDGSIWFAVASFGSWGQGTQVTVSSGPGGGSGGGGSTPDCVTGKVEY

TKYNDEDTFTVKVGDKELFTNRANLQSLLLSAQITGMTVTIKTNACHNGG

GFSEVIFR;

or a sequence substantially identical thereto.

The present disclosure also provides a nucleic acid sequence encoding the isolated or purified antibody or fragment thereof described herein. A vector comprising the nucleic acid molecule just described is also provided.

The isolated or purified antibody or fragment thereof of the present disclosure may be linked to a detectable label.

The present disclosure further provides a method of reducing presence of *C. jejuni* in an animal or an animal environment. The method comprises administering to the animal the isolated or purified antibody or fragment thereof of the present disclosure. The isolated or purified antibody or fragment thereof may be administered orally. The isolated or purified antibody or fragment thereof may be comprised in a yeast expression system. In the method as described, an antibiotic, bacteriocin, or other plant- or animal-derived compound effective against *C. jejuni* may additionally be administered to the animal; alternatively, a competing microbe, optionally co-expressed or co-contained in a probiotic system, may additionally be administered to the animal.

The present disclosure also provides a method of reducing introduction of *C. jejuni* into an animal environment. The isolated or purified antibody or fragment thereof is administered to an inductee animal, prior to introducing the inductee animal into the animal environment.

The present disclosure further provides a *C. jejuni* vaccine or formulation comprising the isolated or purified antibody or fragment thereof of as described herein and an excipient. The vaccine may be for oral delivery.

A method of treating a *C. jejuni* infected subject is also provided; the subject is treated by administering the isolated or purified antibody or fragment thereof as described herein. Optionally, the method may also comprise administering an antibiotic effective against *C. jejuni*. In the method as just described, the subject may be a livestock animal selected from the group consisting of a chicken, cow, or sheep; alternatively, the subject may be a human.

The present disclosure further provides a use of the isolated or purified antibody or fragment thereof described herein for treating or for preparing a medicament for treating a *C. jejuni* infection in a subject in need thereof.

A method of detecting *C. jejuni* in a sample is also provided. The sample is contacted with the isolated or purified antibody or fragment thereof described herein, then the presence of bound antibody is detected. The sample may comprise a bodily fluid or fecal material; alternatively, the sample may comprise a food product or a surface swab from a food product.

The present disclosure also provides a kit for detecting *C. jejuni* in a sample. The kit may comprise the isolated or purified antibody or fragment thereof of the present disclosure and instructions for use in detecting *C. jejuni*. A detection reagent for detecting *C. jejuni* in a sample is also provided that comprises the isolated or purified antibody or fragment thereof described herein and a suitable carrier.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 1 shows sequences of $V_HH$ monomers and pentamers prepared herein.

FIG. 2 shows an ELISA analysis of binding of the monomeric and pentameric $V_HH$ to a *C. jejuni* surface antigen, as well as an image of coomassie-stained purified monomer and pentamer antibodies. Various concentrations (ranging from 10 to 0.0001 µg/ml) of monomeric (FlagV1M) and pentameric (FlagV1P) form of Flagella-specific antibodies ($V_HH$) were used in ELISA. Absorbance data were normalized for the actual number of $V_HH$ molecules in monomeric and pentameric formats. Solid squares represent pentabodies $V_HH$ and open squares show momoneric $V_HH$. A representative image of the coomassie-stained purified monomeric and pentameric $V_HH$ is shown above the ELISA analysis.

FIGS. 3A, 3B and 3C show SPR analysis of the binding of monomeric $V_HH$ FlagV1M and FlagV6M to *C. jejuni* flagella The sensorgram shows binding of 28, 42, 56, 70, 140 and 190 nM FlagV1M (FIG. 3A) or FlagV6M (FIG. 3B) to 700 RUs of biotinylated flagellin captured on an SA sensorchip. The open circles are the data points and the curved lines are the fitting of the data to a 1:1 interaction model. FIG. 3C is a SPR sensorgram for pentameric FlaV1P showing increase in functional affinity (avidity); this confirms the ELISA results shown in FIG. 2.

Flagella prepared from Fla A mutant (lane 1), Fla B mutant (lane 2) and wild type 81-176 (lane 3) strains of *C. jejuni*, were blotted onto nitrocellulose membrane, and were reacted with FlagV1P. The flagellin component was detected by anti-His AP conjugates (lane 1-3).

Figure 5:
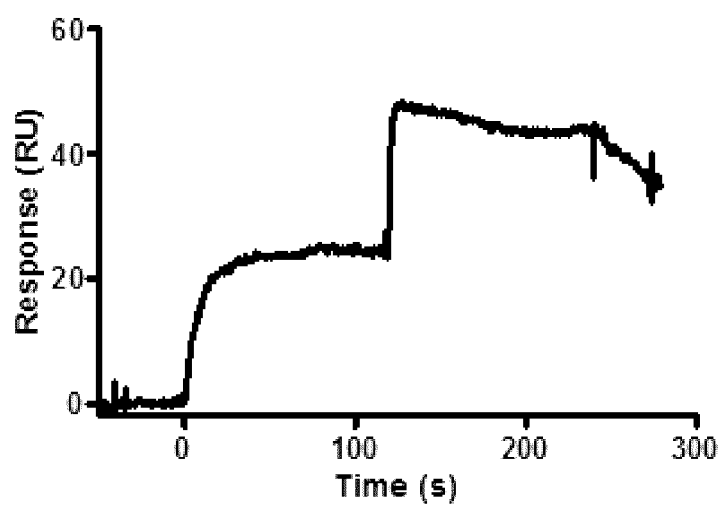

FIG. 5 is a sensorgram showing results of SPR co-injection experiments for FlagV1M and FlagV6M. Each $V_H H$ was injected over immobilized flagella. FlagV1M and FlagV6M appeared to bind distinct, non-overlapping epitopes since the signal approximately doubled with the second injection.

Figure 6:
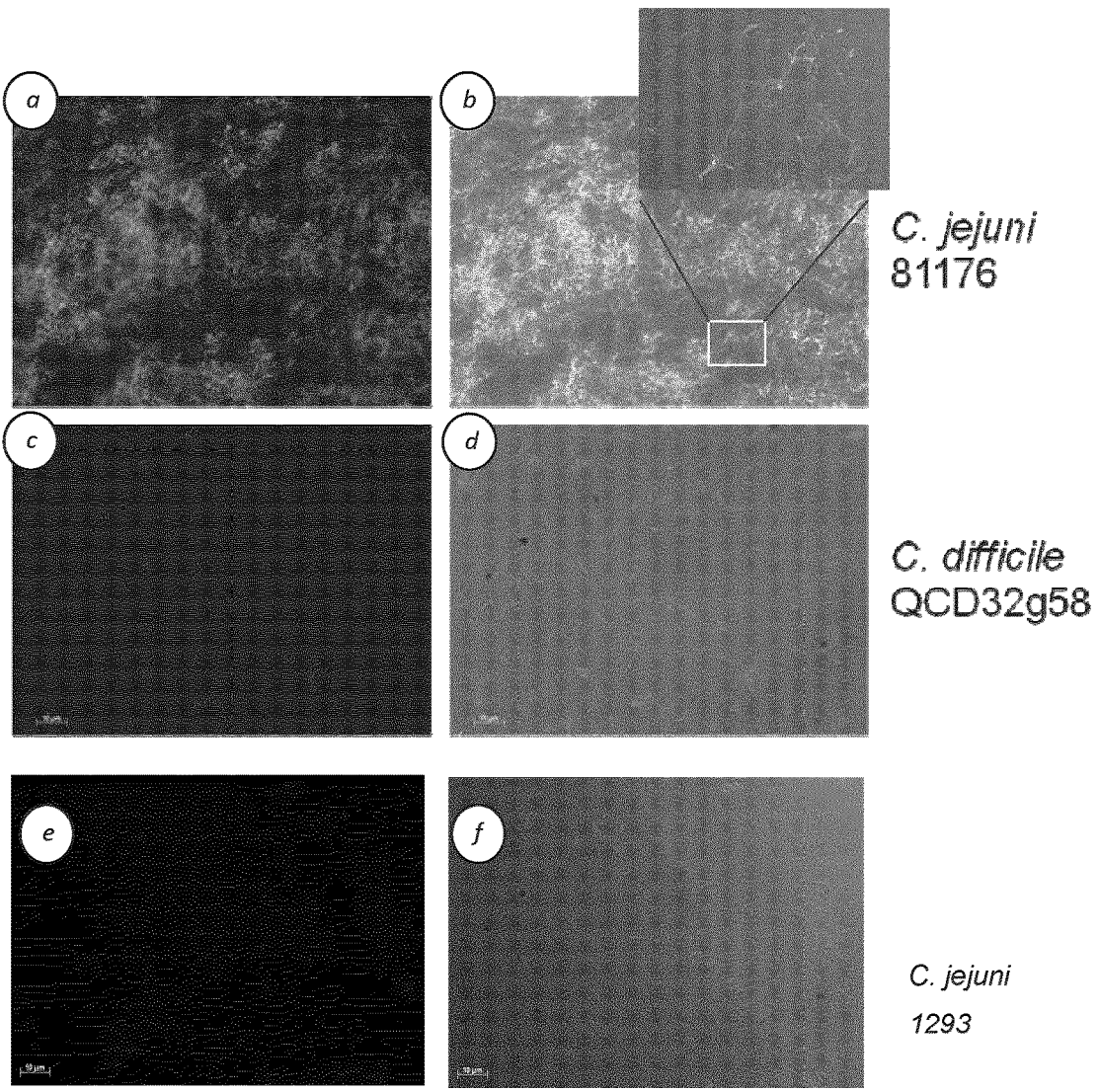

FIG. 6 shows photographs showing fluorescently labeled FlagV1P hybridized with either *C. jejuni* (strain 81176) (panel a,b), or *C. difficile* bacteria (panel c, d) and *C. jejuni* (strain 1293) (panel e,f) as controls. *C. jejuni* strain (a, b) were specifically detected by FITC-labeled pentamer and shown in white in the image (a, b) while control strains are nor stained by the same antibodies (shown as dark or grey background; c, d, e, and f).

Figure 7:
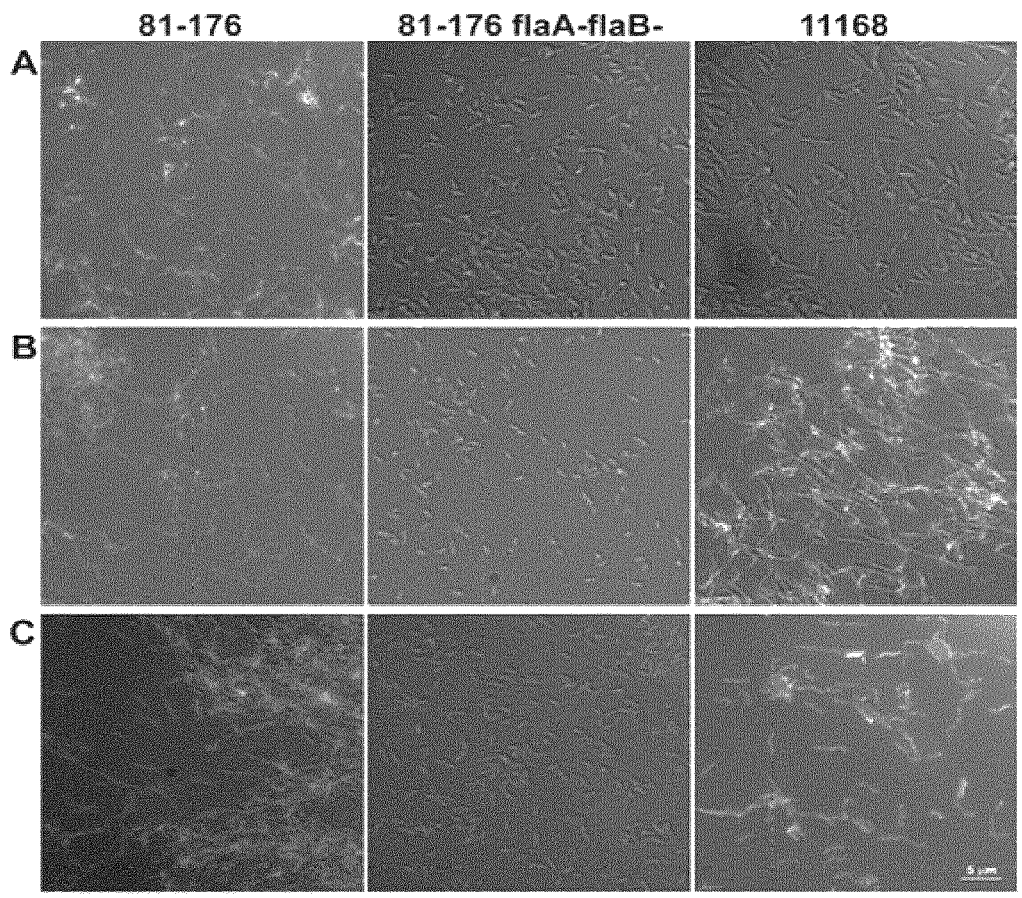

FIG. 7 is a collection of fluorescence microscopy images showing FlagV1P (row A) and FlagV6P (row B) binding to various *C. jejuni* strain 81-176, 81-176 flaA-flaB-, or *C. jejuni* strain 11168 flagella. Row C is fluorescence microscopy images showing rabbit polyclonal anti-81-176 flagella antibodies binding to each of the three strains. Representative field of view are shown for all images at the same magnification, as indicated by the 5 µm bar. The binding of FITC-labeled pentabodies appeared as white in the images of row A (left panel); row B (left and right panels); and row C (left and right panels). FlagV1P did not label *C. jejuni* strain 1168 (row A, right panel); both FlagV1P and FlagV6P did not label 81-176 flaA-flab-mutants (rows A, B, and C, middle panels).

Figure 8:
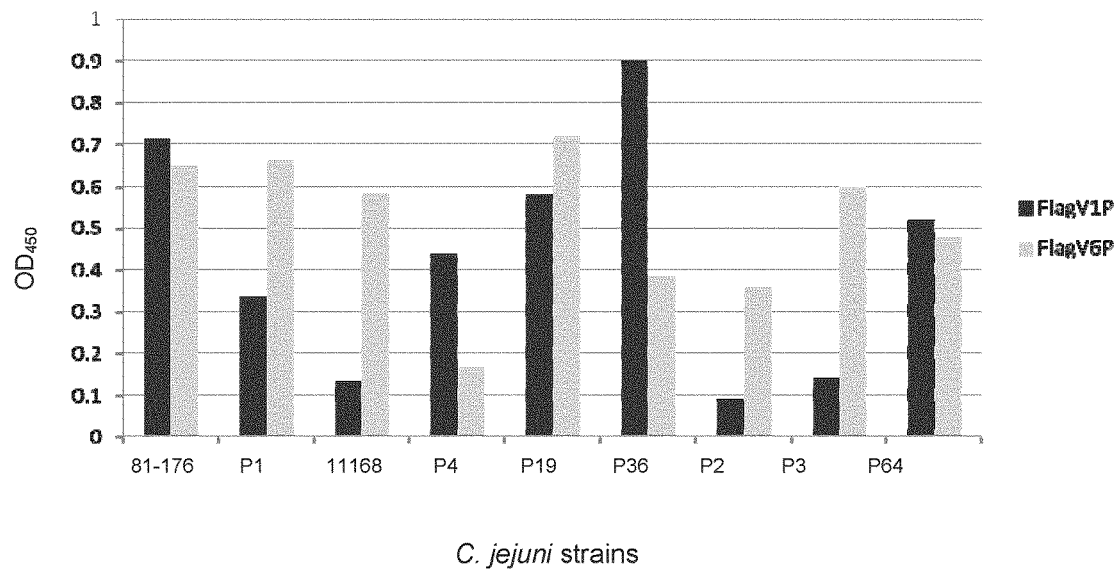

FIG. 8 is a bar graph showing ELISA results of binding of Flag1V1P and FlagV6P to flagella isolates from 9 different strains of *C. jejuni*. Absorbance values indicate an average of two independent experiments.

Figure 9:
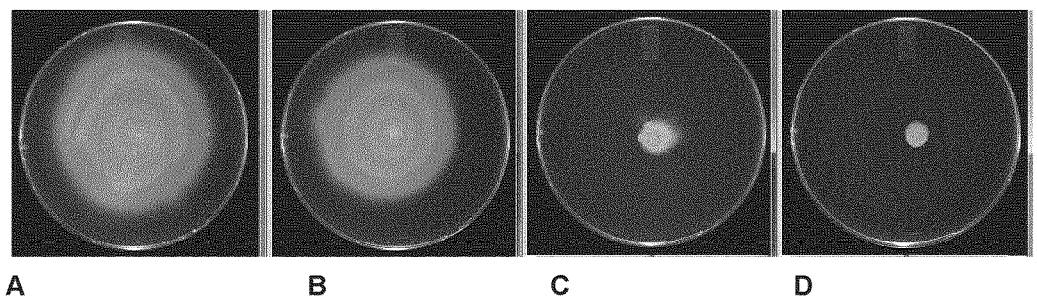

FIG. 9 illustrates the results of a motility assay of *C. jejuni* in the absence or presence of FlagV1P. Pictures were taken after 53 hrs of incubation. Panel A: *C. jejuni* bacteria incubated with buffer as control; panel B: bacteria incubated with an unrelated pentabody; panel C: bacteria incubated with FlagV1M; and panel D: bacteria incubated with FlagV1P.

Figure 10:
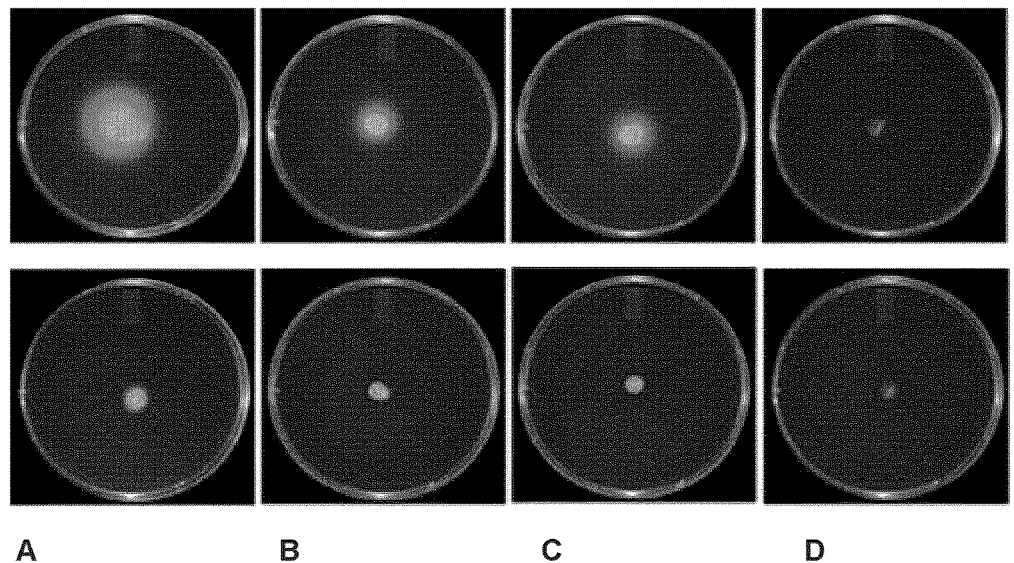

FIG. 10 depicts the results of a motility assay of *C. jejuni* when the bacteria were treated with a combination of pentabodies and antibiotics. The top row illustrates bacterial growth when treated with the control buffer while the bottom row represents the bacteria treated with FlagV1P (at a concentration of 1 µg/ml). Increasing concentrations of tetracycline were used: 0 µg/ml (column A), 4 µg/ml (column B), 16 µg/ml (column C), and 64 µg/ml (column D). Pictures were taken after 24 h of incubation.

Figure 11A:
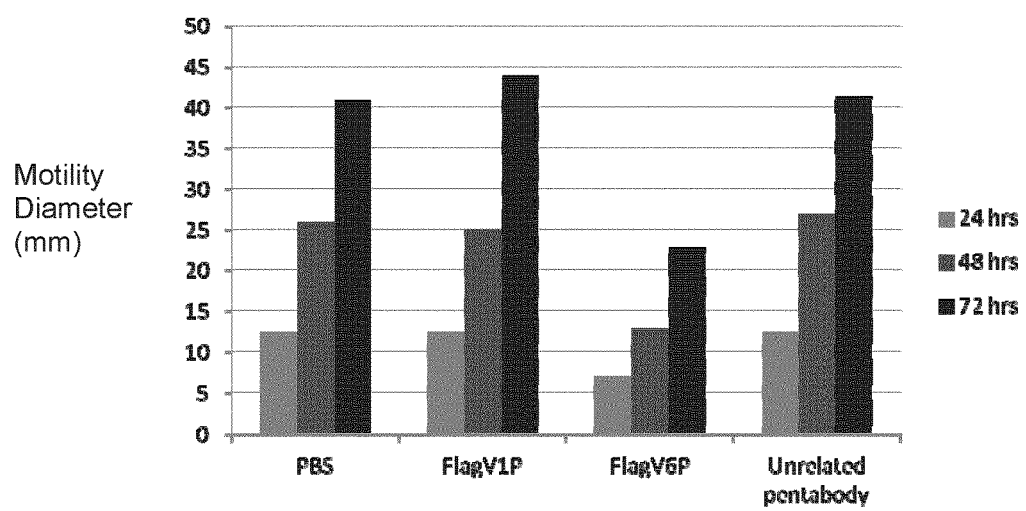
Figure 11B:
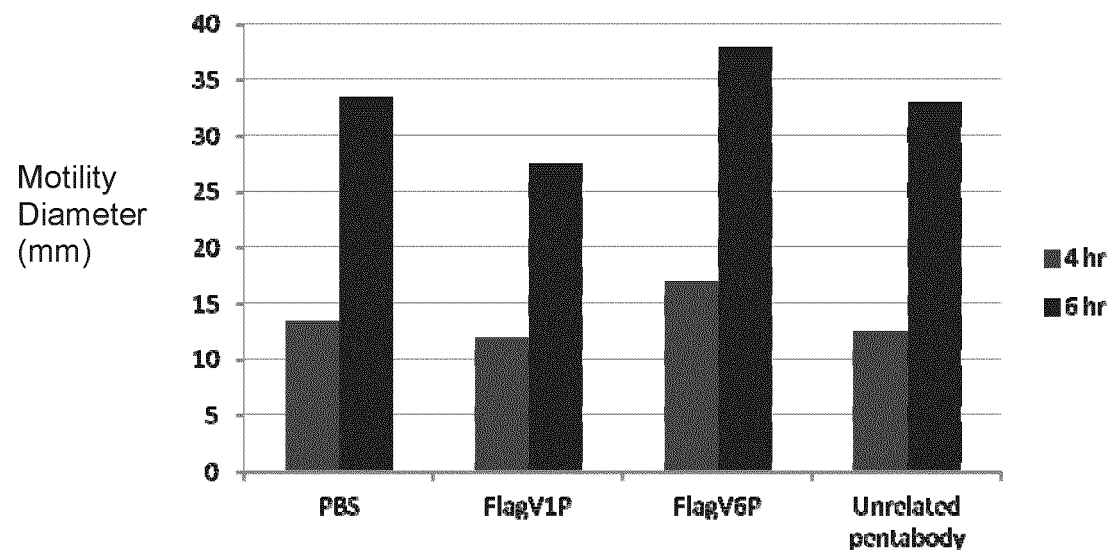

FIGS. 11A and 11B show the results of motility assays, illustrating the cross-reactivity of the FlagV6P to *C. coli* but not *Salmonella typhimurium*. The bacterial growth of *C. coli* strain VC167 (FIG. 11A) and *S. enterica* serovar *typhimurium* (FIG. 11B) were measured at different time points. Antibodies were used at a concentration of 1 µg/µl.

Figure 12A:
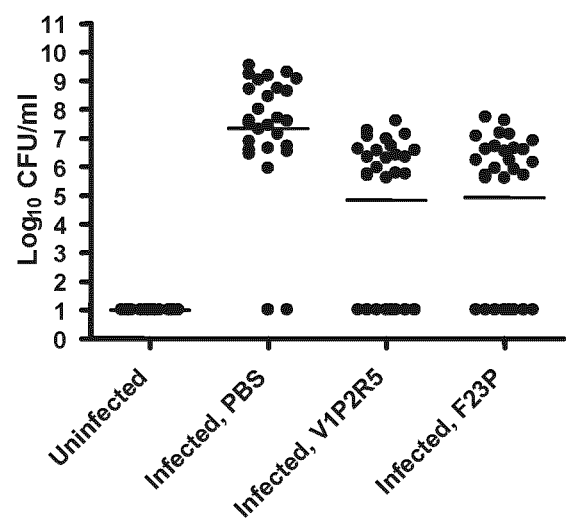
Figure 12B:
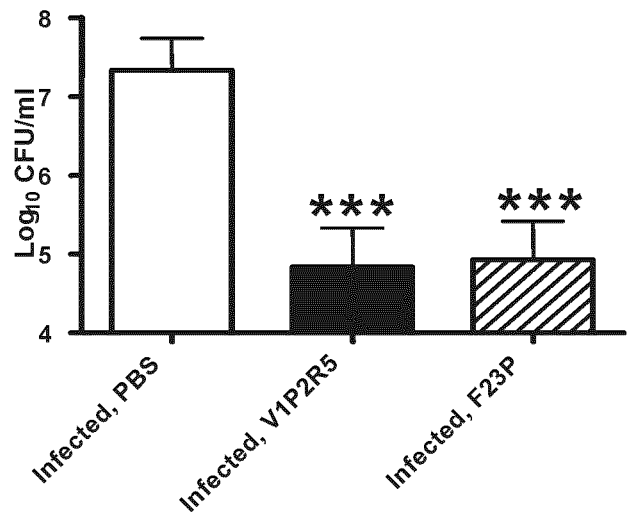

FIGS. 12A and 12B illustrate the effect of oral administration of FlagV1P and FlagV1F23P on the levels of *Campylobacter jejuni* colonization of chickens inoculated with $10^8$ *C. jejuni* cells. After challenge with *C. jejuni*, chickens received FlagV1P (labeled FlagV1P2R5) or FlagV1F23P (labeled F23P). An uninfected, negative control group was also included. FIG. 12A shows a scatterplot of the bacterial burdens in the individual ceca, with the mean cecal bacterial burden denoted by a horizontal line. FIG. 12B shows the bacterial burdens (mean+SEM) in the ceca of chickens treated with PBS (open bars), FlagV1P (closed bars), or FlagV1F23P (hatched bars). ***$p<0.001$, One-way ANOVA, followed by Bonferroni multiple comparison test.

Figure 13:
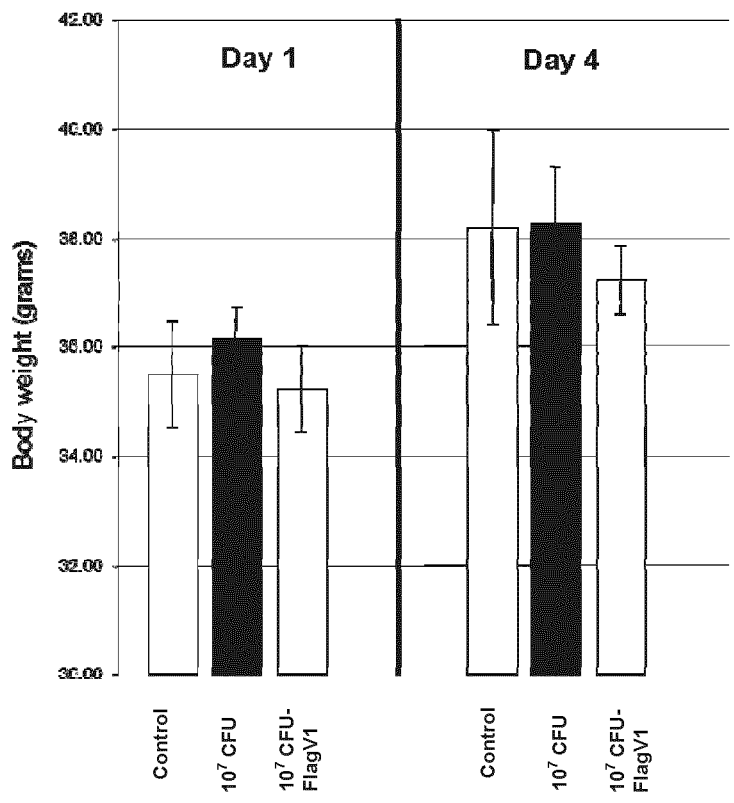

FIG. 13 shows the effect of administration of FlagV1P (1 mg) on chicken body weight. Chicken were weighed one day and four days after challenging with *C. jejuni* alone or challenge followed by pentabody administration. PBS was used as control and body weights (in grams) were measured at day one and day four. The average body weight±standard deviation of the values obtained from 28 replicates is shown for each group. No significant difference was found between the groups.

Figure 14:
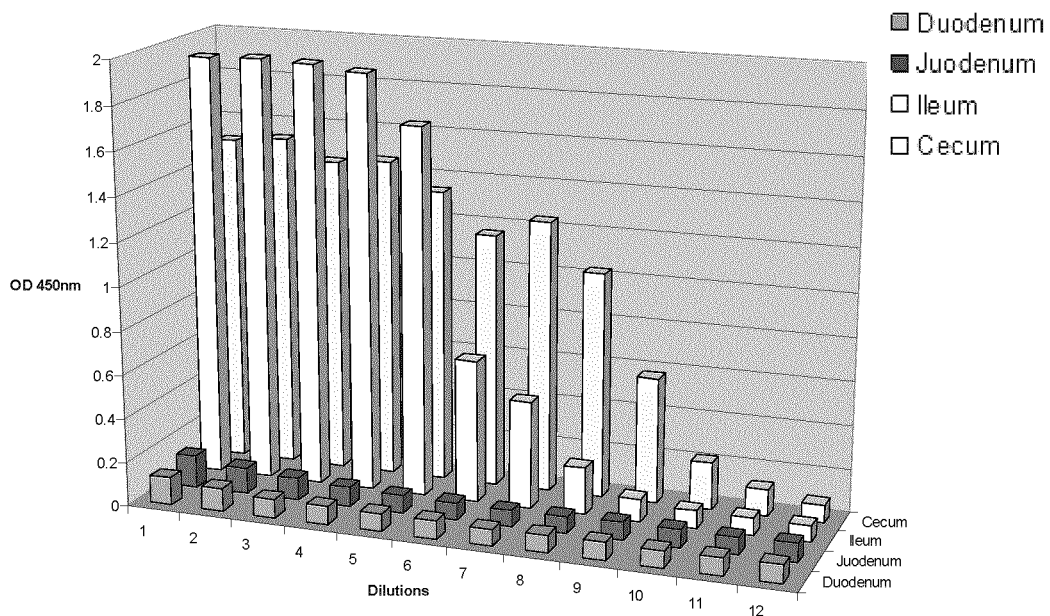

FIG. 14 is a bar graph showing results of the detection of FlagV1P in different parts of chicken intestinal tract. Chicken were gavaged with the FlagV1P and intestinal fluids were collected from cecum, ileum, jejunum, and duodenum. 2-fold serial dilutions were prepared and subjected to ELISA. Results in the graph show that pentabodies were detected mostly in cecum and Ileum fluid extracts.

Figure 15A:
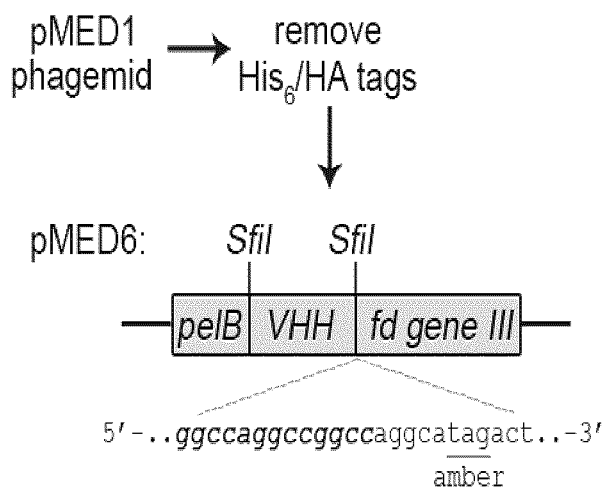
Figure 15B:
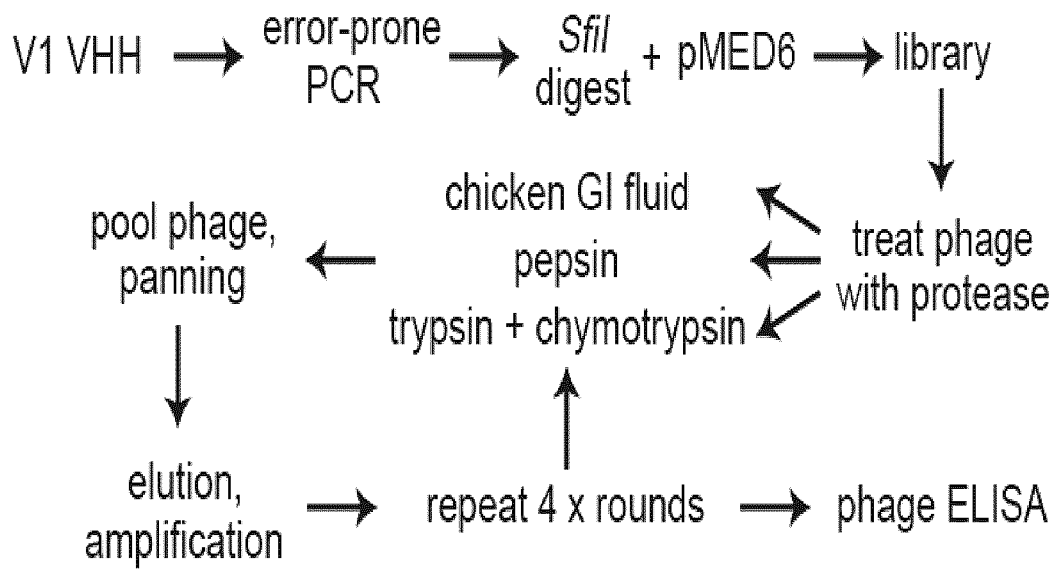
Figure 15C:
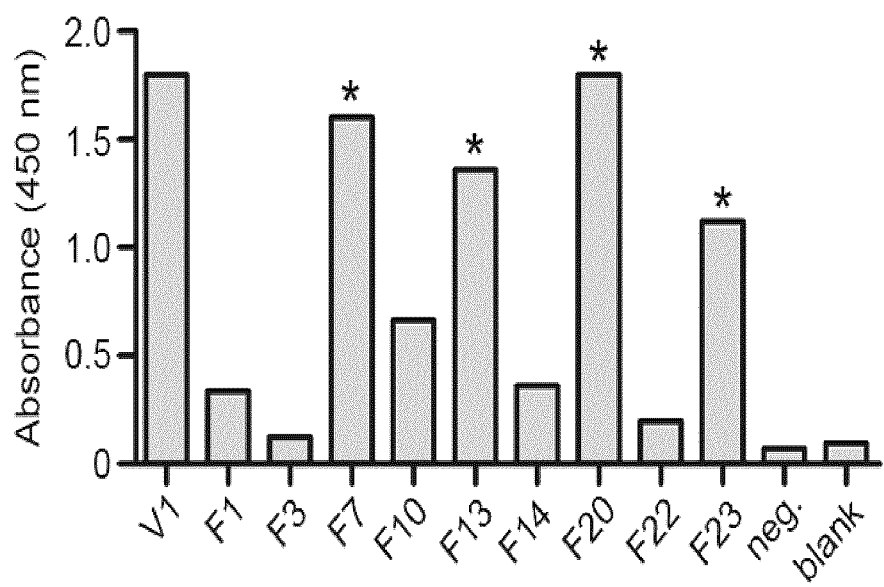

FIGS. 15A, 15B, and 15C illustrate methodology for isolation of protease-resistant $V_H H$ FlagV1M variants. FIG. 15A shows the multi-cloning site of the phagemid vector pMED6. DNA encoding the $His_6$/HA tag was removed from the sequence between the '3 SfiI site (bold and italics) and the amber stop codon (underlined). FIG. 15B shows the work-flow diagram highlighting the construction of the FlagV1M $V_H H$ error-prone PCR library, protease treatment of phages and panning scheme. FIG. 15C is a bar graph showing phage ELISA results for 9 $V_H H$ isolated from panning of protease-treated phages from the V1 error-prone PCR library. Asterisks denote the clones that showed comparable signals to FlagV1M.

Figure 16A:
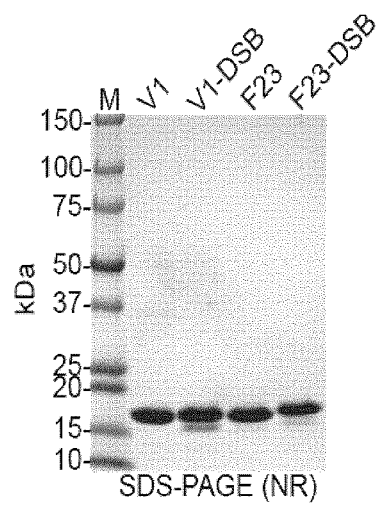
Figure 16B:
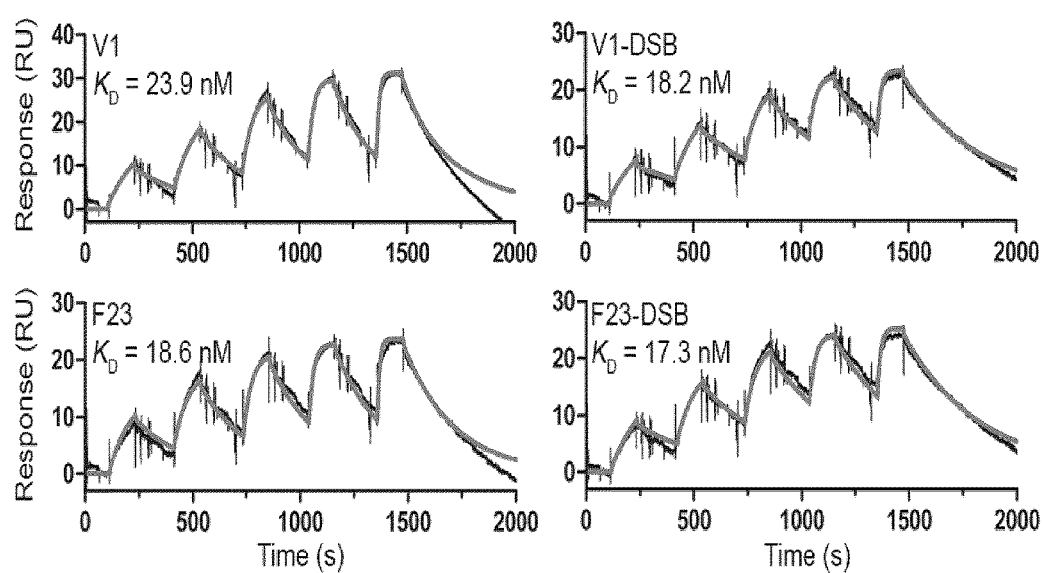
Figure 16C:
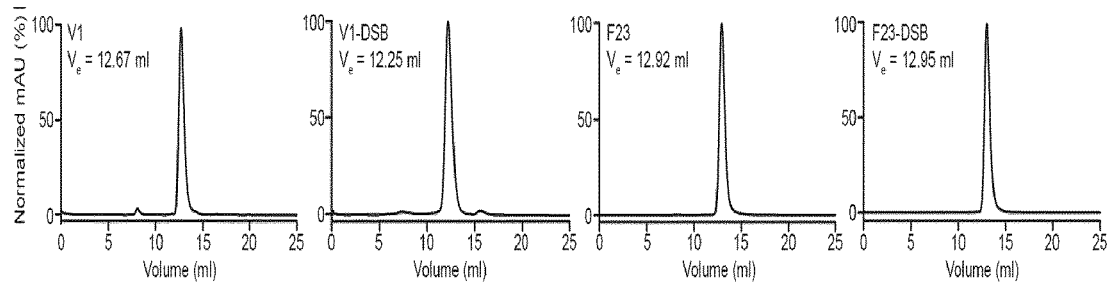

FIGS. 16A, 16B and 16C provide biophysical characterization of FlagV1-derived antibodies. V1=FlagV1M; F23=FlagV1F23M; V1-DSB=FlagV1MDSB; F23-DSB=FlagV1F23MDSB. FIG. 16A is a non-reducing SDS-PAGE gel showing separation of various $V_H H$; the soluble bacterial expression yielded up to 23 mg/L $V_H H$. All ran at their expected molecular masses. FIG. 16B shows single-cycle kinetic SPR sensorgrams of the various $V_H H$. The $V_H H$ retain high affinity binding to immobilized *C. jejuni* flagella and fit a 1:1 binding model. The $K_D$ for each $V_H H$ is shown on the sensorgrams. FIG. 16C shows Superdex 75™ size-exclusion chromatography profiles of the various $V_H H$, demonstrating that all are non-aggregating monomers, with all samples approaching 100% monomer peaks.

Figure 17:
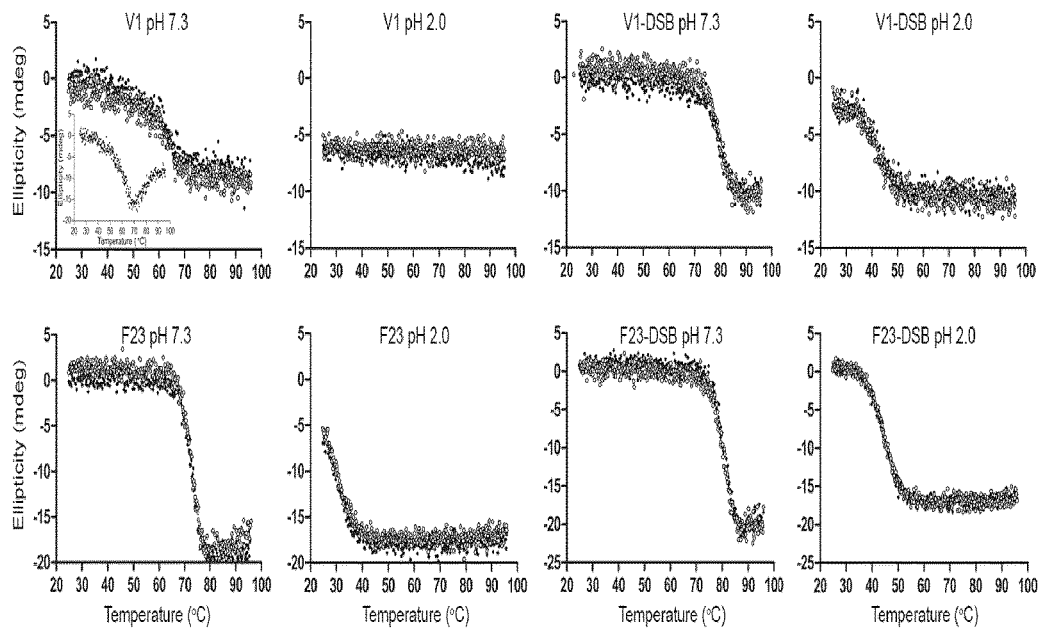
Figure 18:
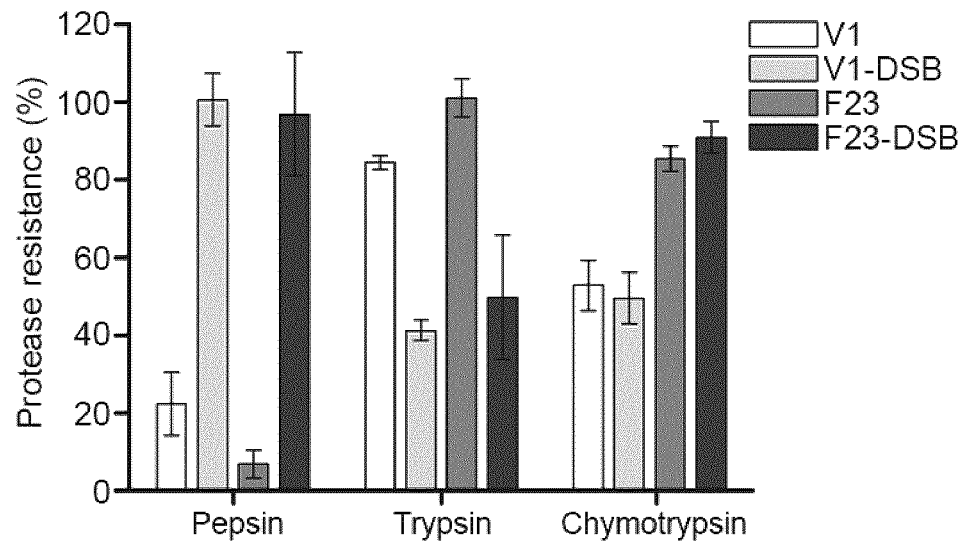

FIG. 17 shows thermal unfolding curves of FlagV1M and FlagV1F23M $V_H H$ and their disulfide-bond variants at neutral pH (7.3) and acidic pH (2.0). Mid-point unfolding temperatures (melting temperature, $T_m$) were calculated. At pH 2.0, V1 was fully denatured and FlagV1F23M partially denatured at the starting temperature of 25° C. FlagV1MDSB was partially denatured at pH 2.0 while FlagV1F23MDSB was fully folded, demonstrating the additive effects of the FlagV1F23M and extra disulfide bond on $V_H H$ thermal stability. Open circles represent replicate 1; solid circles represent replicate 2. V1=FlagV1M; F23=FlagV1F23M; V1-DSB=FlagV1MDSB; F23-DSB=FlagV1F23MDSB FIG. 18 shows the protease susceptibility of FlagV1M and FlagV1F23M $V_H H$ and their disulfide-bond variants to the major gastrointestinal proteases. $V_H H$ were digested with pepsin, trypsin, and chymotrypsin; in control experiments, $V_H H$ were incubated in the absence of the enzymes. Digested $V_H H$ and controls were separated by SDS-PAGE.

Figure 19A:
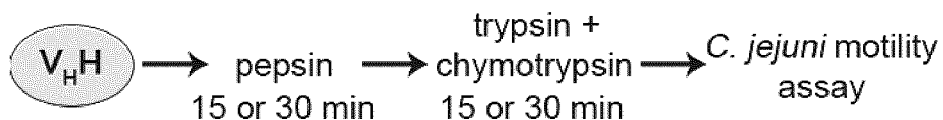
Figure 19B:
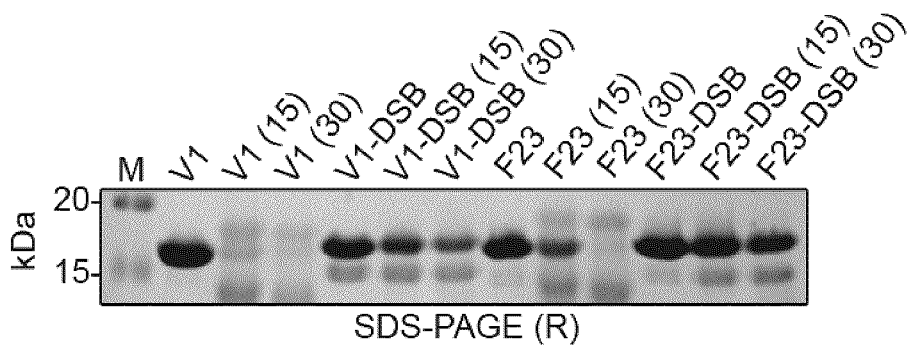
Figure 19C:
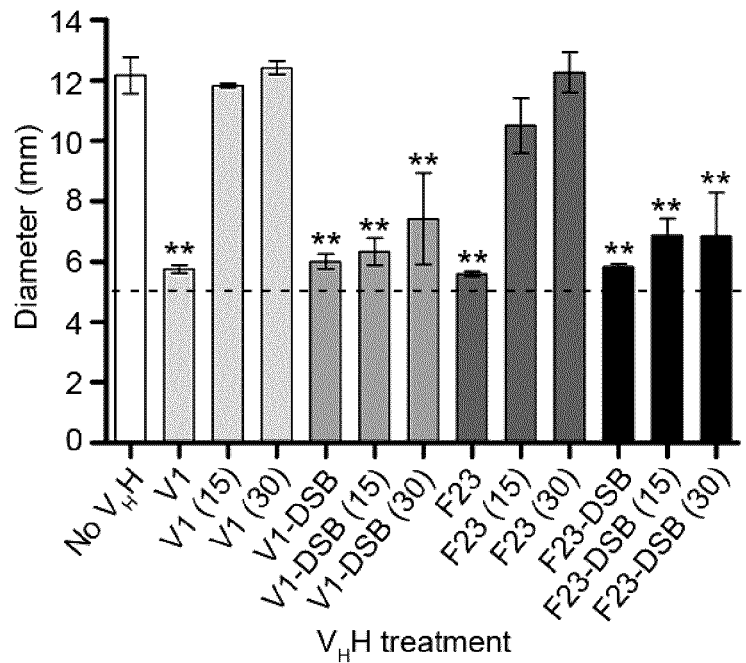
Figure 20:
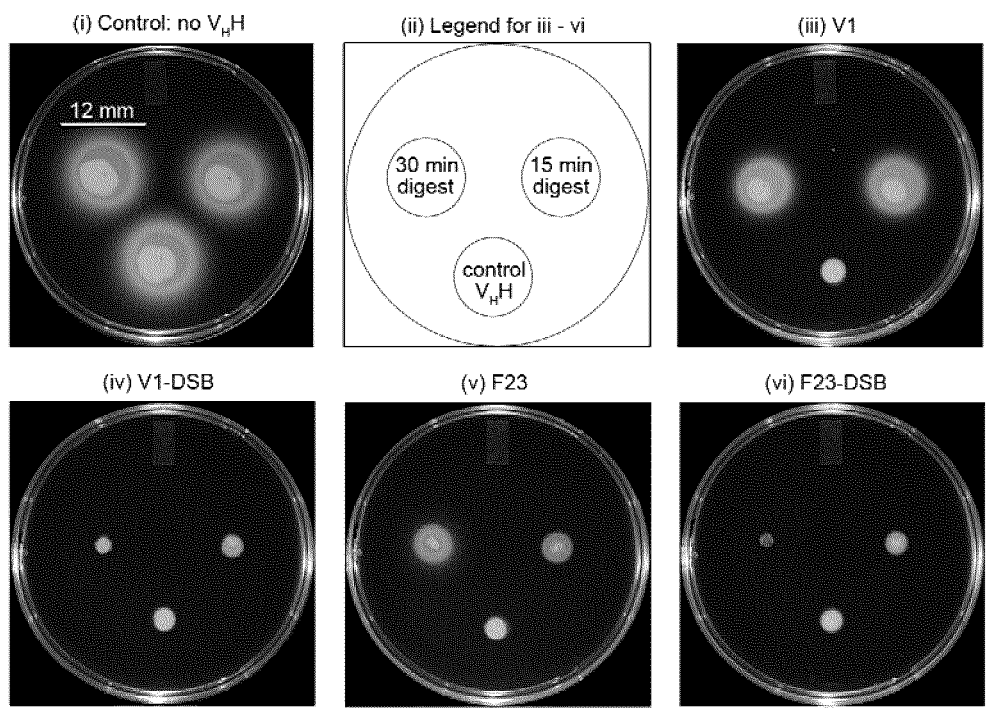

The bar graph summarizes the protease resistance profiles generated by densitometric analysis of SDS-PAGE gels. A total of 3 independent digestions were performed for each $V_HH$ and each protease. Error bars represent mean protease resistance±SEM. V1=FlagV1M; F23=FlagV1F23M; V1-DSB=FlagV1MDSB; F23-DSB=FlagV1F23MDSB FIGS. 19A, 19B, and 19C show a reduction of *C. jejuni* motility by $V_HH$ exposed to multiple proteases. FIG. 19A is a schematic diagram illustrating the sequential digest of $V_HH$ with pepsin followed by trypsin and chymotrypsin. FIG. 19B is a reducing SDS-PAGE gel analysis of sequential digests. FIG. 19C is a bar graph summary of motility assays. The bars represent the mean diameter of *C. jejuni* on plates treated with buffer control, $V_HH$, or protease-digested $V_HH$ from 3 independent experiments; the error bars represent the SEM. The dashed line at 5 mm represents the starting diameter of *C. jejuni* on the plates. Statistical analysis was performed by one-way ANOVA followed by Dunnett's multiple comparison test, all relative to the control with no $V_HH$ (**p<0.01). FlagV1M and FlagV1F23M $V_HH$ FIG. 20 depicts the result of a representative *C. jejuni* motility assay. *C. jejuni* motility is reduced in the presence of functional $V_HH$. *C. jejuni* strain 81-176 was applied to plates with control buffer or $V_HH$. The diameter of the bacterial growth was measured 24 h after plate inoculation. (i) control *C. jejuni* after 24 h incubation with control buffer (no $V_HH$) containing proteases, (ii) legend for images, (iii) FlagV1M control, 15 and 30 min digests, (iv) FlagV1MDSB control, 15 and 30 min digests, (V) FlagV1F23M control, 15 and 30 min digests, and (vi) FlagV1F23MDSB control, 15 and 30 min digests.

DETAILED DESCRIPTION

Generally, the present disclosure relates to antibodies and fragments thereof that specifically bind to *C. jejuni*. The antibodies and fragments thereof described herein are useful in controlling or diminishing *C. jejuni* prevalence in the food chain. Methods involving administration of *C. jejuni*-specific single-domain antibodies to animals are described, which reduce *C. jejuni* levels.

An isolated or purified antibody or fragment thereof specifically binding to *C. jejuni* flagella, comprising
 a complementarity determining region (CDR) 1 comprising the sequence GLTFRNFHMA (SEQ ID NO:1) or VSTFSINALG (SEQ ID NO:4);
 a CDR2 comprising the sequence ISWSRDRQ (SEQ ID NO:2) or IGSDGTV (SEQ ID NO:5); and
 a CDR3 comprising the sequence AARTASASGDWYKGSYQY (SEQ ID NO:3) or NAAGKRIGSDGSIWFAVASFGS (SEQ ID NO:6).

The purified antibody or fragment thereof exhibits specific binding to *C. jejuni* flagella. The anti-*C. jejuni* functionality may be determined in terms of binding to flagellar proteins of *C. jejuni*, reducing motility of *C. jejuni*, or reducing colonization or incidence of infection of *C. jejuni*. Evaluation of binding and/or motility is well within the capabilities of a skilled artisan using techniques described herein. In one non-limiting example, the purified antibody or fragment thereof binds specifically to flagellin. In a further non-limiting example, the purified antibody or fragment thereof binds specifically to the Fla A component of flagellin.

The term "antibody", also referred to in the art as "immunoglobulin" (Ig), used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immmunoglobulin light chain folds into a variable ($V_L$) and a constant ($C_L$) domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen binding determinants of the molecule, and thus determines the specificity of an antibody for its target antigen. The majority of sequence variability occurs in six hypervariable regions, three each per variable heavy ($V_H$) and light ($V_L$) chain; the hypervariable regions combine to form the antigen-binding site, and contribute to binding and recognition of an antigenic determinant. The specificity and affinity of an antibody for its antigen is determined by the structure of the hypervariable regions, as well as their size, shape and chemistry of the surface they present to the antigen. Various schemes exist for identification of the regions of hypervariability, the two most common being those of Kabat and of Chothia and Lesk. Kabat et al (1991a; 1991b) define the "complementarity-determining regions" (CDR) based on sequence variability at the antigen-binding regions of the $V_H$ and $V_L$ domains. Chothia and Lesk (1987) define the "hypervariable loops" (H or L) based on the location of the structural loop regions in the $V_H$ and $V_L$ domains. As these individual schemes define CDR and hypervariable loop regions that are adjacent or overlapping, those of skill in the antibody art often utilize the terms "CDR" and "hypervariable loop" interchangeably, and they may be so used herein. For this reason, the regions forming the antigen-binding site are presently referred to herein as CDR L1, CDR L2, CDR L3, CDR H1, CDR H2, CDR H3 in the case of antibodies comprising a $V_H$ and a $V_L$ domain; or as CDR1, CDR2, CDR3 in the case of the antigen-binding regions of either a heavy chain or a light chain. The CDR/loops are referred to herein according to the IMGT numbering system (Lefranc, M.-P. et al., 2003), which was developed to facilitate comparison of variable domains. In this system, conserved amino acids (such as Cys23, Trp41, Cys104, Phe/Trp118, and a hydrophobic residue at position 89) always have the same position. Additionally, a standardized delimitation of the framework regions (FR1: positions 1 to 26; FR2: 39 to 55; FR3: 66 to 104; and FR4: 118 to 129) and of the CDR (CDR1: 27 to 38, CDR2: 56 to 65; and CDR3: 105 to 117) is provided.

The region outside of the CDR is referred to as the framework region (FR). The FR provides structural integrity to the variable domain and ensures retention of the immunoglobulin fold. This characteristic structure of antibodies provides a stable scaffold upon which substantial antigen-binding diversity can be explored by the immune system to obtain specificity for a broad array of antigens (Padlan et al, 1994).

An "antibody fragment" as referred to herein may include any suitable antigen-binding antibody fragment known in the art. The antibody fragment may be obtained by manipulation of a naturally-occurring antibody, or may be obtained using recombinant methods. For example, an antibody fragment may include, but is not limited to Fv, single-chain Fv (scFv; a molecule consisting $V_L$ and $V_H$ connected with a peptide linker), Fab, Fab', F(ab')$_2$, single domain antibody (sdAb), and multivalent presentations of these.

In a non-limiting example, the antibody fragment may be a single domain antibody (sdAb) derived from naturally-occurring sources. Heavy chain antibodies of camelid origin (Hamers-Casterman et al, 1993) lack light chains and thus their antigen binding sites consist of one domain, termed $V_H$H. sdAb have also been observed in shark and are termed VNARs (Greenberg et al., 1995; Nuttall et al, 2003); other sdAb may be engineered based on human heavy or light chain sequences (Jespers et al, 2004; To et al, 2005). As used herein, "sdAb" includes those directly isolated from $V_L$, $V_H$, $V_H$H or $V_{NAR}$ reservoir of any origin through phage display or other display technologies and those generated through further modification of such sdAb by humanization, affinity maturation, stabilization, solubilization (e.g., camelization), or other methods of antibody engineering. Also encompassed by embodiments described herein are homologues, derivatives, or fragments that retain the antigen-binding function and specificity of the sdAb.

SdAb are excellent building blocks for novel antibody molecules due to their high thermostability, high detergent resistance, relatively high resistance to proteases (Dumoulin et al, 2002) and high production yield (Arbabi-Ghahroudi et al, 1997); they can also be engineered to have very high affinity by isolation from an immune library (Li et al, 2009) or by in vitro affinity maturation (Davies & Riechmann, 1996).

For applications such as toxin neutralization and/or target inactivation, antibody fragments (particularly sdAb) are preferable to whole antibodies (e.g., IgG) due to lower production cost in prokaryotic systems and ease of genetic manipulation. Additionally, $V_H$H, have been shown to be extremely stable when cloned and expressed as monomers using recombinant expression systems (Arbabi-Ghahroudi et al., 1997; Muyldermans 2001).

A person of skill in the art would be well-acquainted with the structure of a single-domain antibody. A sdAb comprises a single immunoglobulin domain that retains the immunoglobulin fold; most notably, only three CDR form the antigen-binding site. However, not all CDR may be required for binding the antigen. For example, and without wishing to be limiting, one, two, or three of the CDR may contribute to binding and recognition of the antigen by the sdAb of the present disclosure. The CDR of the sdAb are referred to herein as CDR1, CDR2, and CDR3, and are based on IMGT numbering system (Lefranc, M.-P. et al., 2003).

As previously stated, the antibody or fragment thereof may be a sdAb. The sdAb may be of camelid origin, and thus may be based on camelid framework regions; alternatively, the CDR may be grafted onto the framework regions of other antibody domains, for example but not limited to VNAR, human $V_H$ or human $V_l$ framework regions. In yet another alternative, the CDR described above may be grafted onto the framework regions of other types of antibody fragments (Fv, scFv, Fab). The present embodiment further encompasses an antibody fragment that is "humanized" using any suitable method know in the art, for example, but not limited to CDR grafting and veneering. Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In the process of CDR grafting, one or more than one of the heavy chain CDR defined herein may be fused or grafted to a human variable region ($V_H$, or $V_L$), or to other human antibody fragment framework regions (Fv, scFv, Fab). In such a case, the conformation of said one or more than one hypervariable loop is preserved, and the affinity and specificity of the sdAb for its target (i.e., flagella) is also preserved. CDR grafting is known in the art and is described in at least the following: U.S. Pat. No. 6,180,370, U.S. Pat. No. 5,693,761, U.S. Pat. No. 6,054,297, U.S. Pat. No. 5,859,205, and European Patent No. 626390. Veneering, also referred to in the art as "variable region resurfacing", involves humanizing solvent-exposed positions of the antibody or fragment; thus, buried non-humanized residues, which may be important for CDR conformation, are preserved while the potential for immunological reaction against solvent-exposed regions is minimized. Veneering is known in the art and is described in at least the following: U.S. Pat. No. 5,869,619, U.S. Pat. No. 5,766,886, U.S. Pat. No. 5,821,123, and European Patent No. 519596. Persons of skill in the art would be amply familiar with methods of preparing such humanized antibody fragments.

The isolated or purified antibody or fragment thereof of the present disclosure may comprise a CDR1 of sequence GLTFRNFHMA (SEQ ID NO:1), a CDR2 of sequence ISWSRDRQ (SEQ ID NO:2), and a CDR3 of sequence AARTASASGDWYKGSYQY (SEQ ID NO:3). The antibody or fragment thereof may be a sdAb. The sdAb may be of camelid origin, and thus may be based on camelid framework region. In a more specific example, the isolated or purified antibody or fragment thereof may comprise the sequence:

```
                                       (SEQ ID NO: 7)
QVX₁LX₂ESGGGLVQAGGSRRLSCATSGLTFRNFHMAWFRQVAGKERE

VVX₃AISWSRDRQYYPDPVKGRFTX₄TRDNAKNTVYLQMNSLKPEDTA

VYYCAARTASASGDWYKGSYQYWGQGTQVTVSS,
``` where $X_1$=K or Q; $X_2$=E or V; $X_3$=A or C; $X_4$=I or C; or a sequence substantially identical thereto. In a further, non-limiting example, the isolated or purified antibody or fragment thereof may comprise the sequence:

```
                                       (SEQ ID NO: 8)
QVKLEESGGGLVQAGGSRRLSCATSGLTFRNFHMAWFRQVAGKEREVVAA

ISWSRDRQYYPDPVKGRFTITRDNAKNTVYLQMNSLKPEDTAVYYCAART

ASASGDWYKGSYQYWGQGTQVTVSS, also referred to herein as FlagV1M;

(SEQ ID NO: 9)
QVQLVESGGGLVQAGGSRRLSCATSGLTFRNFHMAWFRQVAGKEREVVAA

ISWSRDRQYYPDPVKGRFTITRDNAKNTVYLQMNSLKPEDTAVYYCAART

ASASGDWYKGSYQYWGQGTQVTVSS, also referred to herein as FlagV1F23M;

(SEQ ID NO: 10)
QVKLEESGGGLVQAGGSRRLSCATSGLTFRNFHMAWFRQVAGKEREVVCA

ISWSRDRQYYPDPVKGRFTCTRDNAKNTVYLQMNSLKPEDTAVYYCAART

ASASGDWYKGSYQYWGQGTQVTVSS, also referred to herein as FlagV1MDSB;
```

```
                                                    (SEQ ID NO: 11)
QVQLVESGGGLVQAGGSRRLSCATSGLTFRNFHMAWFRQVAGKEREVVCA

ISWSRDRQYYPDPVKGRFTCTRDNAKNTVYLQMNSLKPEDTAVYYCAART

ASASGDWYKGSYQYWGQGTQVTVSS, also referred to herein as FlagV1F23MDSB;
``` or a sequence substantially identical thereto.

An isolated or purified antibody or fragment thereof is described herein, comprising a CDR1 of sequence VSTF-SINALG (SEQ ID NO:4), a CDR2 of sequence IGSDGTV (SEQ ID NO:5), and a CDR3 of sequence NAAGKRIGS-DGSIWFAVASFGS (SEQ ID NO:6). The antibody or fragment thereof may be a sdAb. The sdAb may be of camelid origin, and thus may be based on camelid framework regions. In a more specific example, the isolated or purified antibody or fragment thereof may comprise the sequence:

```
                                                    (SEQ ID NO: 12)
QVX₁LX₂ESGGGLVQAGGSLRVSCTASVSTFSINALGWYRQAPGKARE

LVX₃AIGSDGTVYYTDSVKGRFTX₄SRDNAKNTVSLQMSSLKPEDTAV

YYCNAAGKRIGSDGSIWFAVASFGSWGQGTQVTVSS
``` where $X_1$=K or Q; $X_2$=E or V; $X_3$=A or C; $X_4$=I or C; or a sequence substantially identical thereto. In a further, non-limiting example, the isolated or purified antibody or fragment thereof may comprise the sequence:

```
                                                    (SEQ ID NO: 13)
QVKLEESGGGLVQAGGSLRVSCTASVSTFSINALGWYRQAPGKARELVAA

IGSDGTVYYTDSVKGRFTISRDNAKNTVSLQMSSLKPEDTAVYYCNAAGK

RIGSDGSIWFAVASFGSWGQGTQVTVSS, also referred to herein as FlagV6M;

(SEQ ID NO: 14)
QVQLVESGGGLVQAGGSLRVSCTASVSTFSINALGWYRQAPGKARELVAA

IGSDGTVYYTDSVKGRFTISRDNAKNTVSLQMSSLKPEDTAVYYCNAAGK

RIGSDGSIWFAVASFGSWGQGTQVTVSS, also referred to herein as FlagV6F23M;

(SEQ ID NO: 15)
QVKLEESGGGLVQAGGSLRVSCTASVSTFSINALGWYRQAPGKARELVCA

IGSDGTVYYTDSVKGRFTCSRDNAKNTVSLQMSSLKPEDTAVYYCNAAGK

RIGSDGSIWFAVASFGSWGQGTQVTVSS, also referred to herein as FlagV6MDSB;

(SEQ ID NO: 16)
QVQLVESGGGLVQAGGSLRVSCTASVSTFSINALGWYRQAPGKARELVCA

IGSDGTVYYTDSVKGRFTCSRDNAKNTVSLQMSSLKPEDTAVYYCNAAGK

RIGSDGSIWFAVASFGSWGQGTQVTVSS, also referred to herein as FlagV6F23MDSB;
``` or a sequence substantially identical thereto.

A substantially identical sequence may comprise one or more conservative amino acid mutations. It is known in the art that one or more conservative amino acid mutations to a reference sequence may yield a mutant peptide with no substantial change in physiological, chemical, or functional properties compared to the reference sequence; in such a case, the reference and mutant sequences would be considered "substantially identical" polypeptides. Conservative amino acid mutation may include addition, deletion, or substitution of an amino acid; in one non-limiting example, the conservative amino acid mutation is a conservative amino acid substitution. A conservative amino acid substitution is defined herein as the substitution of an amino acid residue for another amino acid residue with similar chemical properties (e.g. size, charge, or polarity).

A conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), BLAST-P, Blast-N, or FASTA-N, or any other appropriate software that is known in the art.

The substantially identical sequences may be at least 90% identical; in another example, the substantially identical sequences may be at least 90, 91, 92, 93, 94, 95, 96, 97, 98, 99, or 100% identical at the amino acid level to sequences described herein. For example, and without wishing to be limiting in any manner, alignment of FlagV1M, FlagV1F23M, FlagV1MDSB, and FlagV1F23MDSB leads to sequence identities of between 96.8% and 98.4%. Importantly, the substantially identical sequences retain the activity and specificity of the reference sequence. As would be known to one of skill in the art, certain amino acid residues of an antibody, particularly within the framework regions may be mutated without affecting the antigen-binding and other functional properties of the antibody.

The antibody or fragment thereof may also comprise additional sequences to aid in expression, detection, or purification of a recombinant antibody or fragment thereof. For example, and without wishing to be limiting, the antibody or fragment thereof may comprise a targeting or signal sequence (for example, but not limited to ompA), a detection tag (for example, but not limited to c-Myc), a purification tag (for example, but not limited to a histidine purification tag, His$_5$ or His$_6$), or any combination thereof.

The antibody or fragment thereof may also be in a multivalent display. Multimerization may be achieved by any suitable method of known in the art. For example, and without wishing to be limiting in any manner, multimerization may be achieved using self-assembly molecules (Zhang et al, 2004; Merritt & Hol, 1995), as described in WO2003/046560. The described method produces pentabodies by expressing a fusion protein comprising the antibody or fragment thereof and the pentamerization domain of the B-subunit of an AB$_5$ toxin family (Nielson et al, 2000; WO2003/046560); for example, and without wishing to be limiting, the sequence of the pentamerization domain may be (SEQ ID NO: 17)
TPDCVTGKVEYTKYNDEDTFTVKVGDKELFTNRANLQSLLLSAQITGMTV

TIKTNACHNGGGFSEVIFR.

The pentamerization domain assembles into a pentamer, through which a multivalent display of the antibody or fragment thereof is formed. As would be recognized by the skilled person, each subunit in the pentamer comprises the fusion protein described above. As would also be readily recognized by the person of skill in the art, pentamerization of the antibody or fragment thereof in no way alters its antigen binding or recognition (ie., the antibody or fragment thereof binds the same antigen, in the same manner, with the same specificity and affinity). The resulting pentabodies are compact, have high avidity (functional affinity), and are stable antigen-binding molecules (Zhang et al., 2004). These pentavalent antibodies are also capable of enhancing agglutination when bound to antigens (Zhang et al., 2004), thereby increasing their efficacy.

Each subunit of the multimers described herein may be the same or different. Additionally, the multimerization domain may be linked to the antibody or antibody fragment using a linker; such a linker should be of sufficient length and appropriate composition to provide flexible attachment of the two molecules, but should not hamper the antigen-binding properties of the antibody. In one non-limiting example, the linker may be the linker GPGGGSGGGGS (SEQ ID NO:18).

In one specific, non-limiting example, a multimer may comprise the sequence:

(SEQ ID NO: 19)
QVKLEESGGGLVQAGGSRRLSCATSGLTFRNFHMAWFRQVAGKEREVVAA

ISWSRDRQYYPDPVKGRFTITRDNAKNTVYLQMNSLKPEDTAVYYCAART

ASASGDWYKGSYQYWGQGTQVTVSSGPGGGSGGGGSTPDCVTGKVEYTKY

NDEDTFTVKVGDKELFTNRANLQSLLLSAQITGMTVTIKTNACHNGGGFS

EVIFR, also referred to herein as FlagV1P;

(SEQ ID NO: 20)
QVQLVESGGGLVQAGGSRRLSCATSGLTFRNFHMAWFRQVAGKEREVVAA

ISWSRDRQYYPDPVKGRFTITRDNAKNTVYLQMNSLKPEDTAVYYCAART

ASASGDWYKGSYQYWGQGTQVTVSSGPGGGSGGGGSTPDCVTGKVEYTKY

NDEDTFTVKVGDKELFTNRANLQSLLLSAQITGMTVTIKTNACHNGGGFS

EVIFR, also referred to herein as FlagV1F23P;

(SEQ ID NO: 34)
QVKLEESGGGLVQAGGSRRLSCATSGLTFRNFHMAWFRQVAGKEREVVCA

ISWSRDRQYYPDPVKGRFTCTRDNAKNTVYLQMNSLKPEDTAVYYCAART

ASASGDWYKGSYQYWGQGTQVTVSSGPGGGSGGGGSTPDCVTGKVEYTKY

NDEDTFTVKVGDKELFTNRANLQSLLLSAQITGMTVTIKTNACHNGGGFS

EVIFR, also referred to herein as FlagV1PDSB;

(SEQ ID NO: 35)
QVQLVESGGGLVQAGGSRRLSCATSGLTFRNFHMAWFRQVAGKEREVVCA

ISWSRDRQYYPDPVKGRFTCTRDNAKNTVYLQMNSLKPEDTAVYYCAART

ASASGDWYKGSYQYWGQGTQVTVSSGPGGGSGGGGSTPDCVTGKVEYTKY

NDEDTFTVKVGDKELFTNRANLQSLLLSAQITGMTVTIKTNACHNGGGFS

EVIFR, also referred to herein as FlagV1F23PDSB;

(SEQ ID NO: 21)
QVKLEESGGGLVQAGGSLRVSCTASVSTFSINALGWYRQAPGKARELVAA

IGSDGTVYYTDSVKGRFTISRDNAKNTVSLQMSSLKPEDTAVYYCNAAGK

RIGSDGSIWFAVASFGSWGQGTQVTVSSGPGGGSGGGGSTPDCVTGKVEY

TKYNDEDTFTVKVGDKELFTNRANLQSLLLSAQITGMTVTIKTNACHNGG

GFSEVIFR, also referred to herein as FlagV6P;

(SEQ ID NO: 22)
QVQLVESGGGLVQAGGSLRVSCTASVSTFSINALGWYRQAPGKARELVAA

IGSDGTVYYTDSVKGRFTISRDNAKNTVSLQMSSLKPEDTAVYYCNAAGK

RIGSDGSIWFAVASFGSWGQGTQVTVSSGPGGGSGGGGSTPDCVTGKVEY

TKYNDEDTFTVKVGDKELFTNRANLQSLLLSAQITGMTVTIKTNACHNGG

GFSEVIFR, also referred to herein as FlagV6F23P, (SEQ ID NO: 36)
QVKLEESGGGLVQAGGSLRVSCTASVSTFSINALGWYRQAPGKARELVCA

IGSDGTVYYTDSVKGRFTCSRDNAKNTVSLQMSSLKPEDTAVYYCNAAGK

RIGSDGSIWFAVASFGSWGQGTQVTVSSGPGGGSGGGGSTPDCVTGKVEY

TKYNDEDTFTVKVGDKELFTNRANLQSLLLSAQITGMTVTIKTNACHNGG

GFSEVIFR, also referred to herein as FlagV6PDSB;

(SEQ ID NO: 16)
QVQLVESGGGLVQAGGSLRVSCTASVSTFSINALGWYRQAPGKARELVCA

IGSDGTVYYTDSVKGRFTCSRDNAKNTVSLQMSSLKPEDTAVYYCNAAGK

RIGSDGSIWFAVASFGSWGQGTQVTVSSGPGGGSGGGGSTPDCVTGKVEY

TKYNDEDTFTVKVGDKELFTNRANLQSLLLSAQITGMTVTIKTNACHNGG

GFSEVIFR, also referred to herein as FlagV6F23PDSB;

or a sequence substantially identical thereto.

Other forms of multivalent display are also encompassed. For example, and without wishing to be limiting, the antibody or fragment thereof may be presented as a dimer, a trimer, or any other suitable oligomer. This may be achieved by methods known in the art, for example direct linking connection (Nielsen et al, 2000), c-jun/Fos interaction (de Kruif et al, 1996), "Knob into holes" interaction (Ridgway et al, 1996). A multimer may also be formed using the multimerization domains described by Zhu et al. (2010); this form, referred to herein as a "combody" form, is a fusion of the antibody or fragment thereof, as described herein, with a coiled-coil peptide resulting in a multimeric molecule (Zhu et al., 2010).

Another method known in the art for multimerization is to dimerize the antibody or fragment thereof using a Fc domain. In this approach, a Fc gene in inserted into an expression vector; the nucleotide sequence of the antibody or fragment thereof can be amplified and inserted into the vector such that the C-terminus of the antibody or fragment thereof is linked to the hinge region of the Fc without addition of extra residues. The resulting vector can be transfected to a mammalian cell line and the fusion protein may be recombinantly expressed, then purified by affinity chromatography (for example, on a protein A column). One non-limiting example of such a method of multimerization is described by Bell et al (2010) and Iqbal et al (in press). Techniques for implementing such dimerization would be known to those of skill in the art.

In the multimers as described above, subunits within the multimers may comprise the same or different antibodies or fragments thereof, as described herein.

Also encompassed are nucleic acid sequences encoding the antibody or fragment thereof as described herein. Given the degeneracy of the genetic code, a number of nucleotide sequences would have the effect of encoding the polypeptide, as would be readily understood by a skilled artisan. The nucleic acid sequence may be codon-optimized. Vectors comprising the nucleic acids as just described, are encompassed.

A host cell comprising the nucleotide encoding any one of the antibodies or fragment thereof described herein would also be readily recognized by the skilled artisan.

A phage comprising the antibody or fragment thereof described herein and/or display as fusion to one of the viral coat protein (for example, but not limited to g3p of filamentous phages), and/or comprising the nucleotide encoding the antibody or fragment thereof is also encompassed.

The antibody or fragment thereof described herein may be labeled with detectable label. The label may be rendered detectable or may in itself be detectable, so that the presence of binding to $C.$ $jejuni$ can be observed. The detectable label may be a radioisotope, a paramagnetic label (for example gadolinium or iron oxide), a fluorophore, a fluorophore, a fluorescent agent (for example, FITC or Enhanced Green Fluorescent Protein (EGFP)), Near Infra-Red (NIR; for example Cy5.5, Alexa680, Dylight680, or Dylight800) fluorochrome or dye, an echogenic microbubble, an affinity label (for example biotin, avidin, etc), fused to a detectable protein-based molecule, nucleotide, quantum dot, nanoparticle, nanowire, or nanotube or any other suitable agent that may be detected by imaging methods. The antibody or fragment thereof may be linked to the detectable agent using any method known in the art (recombinant technology, chemical conjugation, etc.); optionally a linker may be used as needed. The step of detecting may be accomplished by any suitable method known in the art, for example, but not limited to optical imaging, immunohistochemistry or molecular diagnostic imaging, ELISA, or other suitable method. In a specific, non-limiting example, the antibody or fragment thereof may be linked to a fluorescent agent such as FITC, or may genetically be fused to the Enhanced Green Fluorescent Protein (EGFP).

Methods of reducing the presence of $C.$ $jejuni$ in an animal or an animal environment are described herein. Within an individual animal, reducing the presence may comprise reducing contamination on the surface of the animal, or within the gastrointestinal tract of an animal. Should an animal be systemically infected, the method described herein could be used for reducing the presence of $C.$ $jejuni$. The environment of an animal can relate to the animal's immediate surroundings, such as the walls or floors of a cage or facility, the feeding or watering apparatuses within an animal compound, the bedding materials found in an animal compound, or simply the fecal material present external to the animal within the animal's confines. Administering to an animal the antibody or fragment thereof described herein can be for the purpose of reducing the presence of $C.$ $jejuni$ within the animal to which the antibody or fragment thereof is administered, or an offspring of such an animal, or within the flock, cage or barn in which the animal lives. Reducing $C.$ $jejuni$ within the animal's gastrointestinal tract is one way to reduce contamination within the animal's environment, leading to a safer food supply chain, with lower incidence of contamination.

Administration to the animal may be by any suitable method known in the art. Advantageously, the antibody or fragment thereof described herein may be administered orally. Oral delivery permits the antibody or fragment thereof to be delivered within the water or food supply to an animal, and is less noticeable or stressful to an animal than an injection. Gavage is also an acceptable oral route when highly accurate delivery of an oral dosing regime is desirable. Other routes of administration can also be considered, such as via a systemic, or rectal delivery route. For example, and without wishing to be limiting in any manner, the antibody or fragment thereof may be included in the animal's food supply. In one non-limiting example, the antibody or fragment thereof may be provided in a yeast expression system that is included in the animal's food supply. In a non-limiting example, the antibody or fragment thereof may be displayed on yeast coat protein(s) or expressed internally or externally by the yeast.

Co-administration of another substance that is effective against $C.$ $jejuni$ is also a possible strategy for reducing $C.$ $jejuni$ in an animal environment. For example, administering to the animal an antibiotic either at the same time or at an adjacent time to the delivery of the antibody or fragment thereof can have an additive effect or may have a synergistic effect. The result of which is a reduced likelihood of $C.$ $jejuni$ contamination, but also a reduced usage of antibiotic. A bacteriocin effective against $C.$ $jejuni$ can also be provided to the animal with the antibody or fragment thereof for an additive or synergistic effect. In addition to, or as an alternative to bacteriocin, any other plant- or animal-derived compound, such as a small molecule, peptide, or protein that has effect against $C.$ $jejuni$ may be used together with the antibody or fragment thereof described herein. A competitive microbe may also be provided to the animal concurrently with the antibody or fragment thereof in order to achieve an additive or a synergistic effect. The competitive microbe may be used together with the antibody or fragment thereof described herein as part of a probiotic system. Within such a probiotic system, the antibody or fragment thereof may be co-administered with the competitive microbe, or may be delivered sequentially. Expression of the antibody or fragment thereof described herein within a probiotic system may also be undertaken.

Scaffold engineering of portions of the antibody or fragment thereof outside of the CDR regions can confer additional protease resistance, as well as thermal and low pH resistance. The form of delivery may also be altered with coatings or excipients that provide a protective effect against gut enzymes, thermal or low pH effects, and in this way, the sequence of the antibody or fragment thereof itself need not be modified, but rather the formulation prepared for oral delivery may itself be optimized for the species of subject to which the antibody or fragment thereof is to be delivered.

The dosage form may be of any type acceptable for peptide delivery to animals. Coated forms and slow release forms could be used if desirable. Liquid, powder, crystal, gel, semi-solid, or tablet forms can be used.

The animal to which the antibody or fragment thereof may be delivered may be a bird, such as a broiler chicken or laying hen. Other types of livestock animals, such as cows, sheep, etc. may also benefit from the peptide if *C. jejuni* is present in the animal's gut or surrounding environment. Thus, livestock applications are not limited to poultry. A typical animal environment may be a barn or farm, such as a poultry farm. In order to avoid contamination of an animal environment that is substantially free of *C. jejuni*, a method is provided that prevents introduction of a new contaminated animal or "inductee" animal into the environment, such as a barn. In such a method, the antibody or fragment thereof administering to an inductee prior to introducing the inductee animal into the animal environment, such as a barn or farm. In this way, the animal could be cleared of the likelihood of contamination prior to taking up residence with the other animals who may have already received treatment.

An anti-*C. jejuni* vaccine is described herein which comprises the antibody or fragment thereof described herein, together with an excipient. The vaccine may be formulated for oral delivery, as described above.

A method of treating a *C. jejuni* infected subject is also described, comprising administering to the subject the antibody or fragment thereof described above. Optionally, an antibiotic effective against *C. jejuni* can be co-administered to the subject. While the subject may be livestock, such as a chicken, the method is also applicable to human subjects.

A formulation for such a use in treating *C. jejuni* infection comprises the antibody or fragment thereof together with an excipient. Thus, the antibody or fragment thereof may be used in the preparation of a medicament to treat *C. jejuni* infection in a subject in need thereof.

The antibody or fragment thereof described herein is also useful for methods of detecting *C. jejuni* in a sample. In such a method, a sample is contacted with the antibody or fragment thereof, with or without the presence of a label, and subsequently, the presence of bound antibody or fragment thereof is detected using any acceptable means. The sample may comprise a bodily fluid or fecal material for those instances where detection is used to determine contamination or infection of an individual. In embodiments where the presence of *C. jejuni* is to be assessed in a food product, or in a food processing environment, the sample which is contacted by the antibody or fragment thereof may be a food product, a food container, food processing equipment, or a surface swab from a food product, container or processing equipment.

A kit is provided for conducting such a method, which would include the antibody or fragment thereof itself, together with instructions for use in detecting *C. jejuni*. Optionally, reagents to be used in such a detection kit may be included for the user's convenience.

The antibody or fragment thereof itself may be the main component of detection reagent that is to be used for detecting *C. jejuni* in a sample. Such a detection reagent would also a suitable carrier, such as a buffer.

The present inventors have isolated FlagV1M and FlagV6M, flagellin-binding single domain antibodies (sdAb) isolated from a hyperimmunized llama phage display library by panning against flagella proteins. FlagV1F23M was isolated from a library in which an error-prone PCR approach was used to introduce random mutations in FlagV1M DNA; panning was performed under protease treatment conditions. The equivalent mutations were also conferred to FlagV6M, resulting in FlagV6F23M. Pentavalency was conferred to the FlagV1M, FlagV1F23M, and FlagV6M antibodies by fusion of the sdAb with a protein domain derived from the verotoxin B homopentamer, producing proteins FlagV1P, FlagV1F23P, and FlagV6P. The resulting antibody or fragment thereof, which may be referred to as "pentabodies", are compact, showed high avidity, and are stable antigen-binding molecules. These pentavalent $V_HH$ were capable of enhancing agglutination of *C. jejuni* and *C. coli* when bound to antigens.

Single domain antibodies are, in general, significantly more resistant to proteases than the conventional antibody fragments. However, FlagV1M, FlagV1F23M, FlagV6M, and FlagV6F23M were also modified to possess increased tolerance to gut enzymes, thus increasing efficacy of oral delivery. Typical gut enzymes which may have a destructive effect on a polypeptide include pepsin, trypsin and chymotrypsin. Thus, resistance to these enzymes is advantageous, as the peptide would have more exposure time to bind with ambient *C. jejuni* within the intestinal tract. The modification to FlagV1M, FlagV1F23M, FlagV6M, and FlagV6F23M was made by introducing a second disulfide bridge between residues 54 and 78, producing sdAb FlagV1MDSB, FlagV1F23MDSB, FlagV6MDSB, and FlagV6F23MDSB, respectively. Sites for modification in preparing the disulfide bridge modified antibodies were selected based on optimal alteration to $V_HH$ thermostability and proteolytic stability when cysteine residues are introduced at specific sites.

The $V_HH$ and pentabodies counterparts were specific for flagellin, a *C. jejuni* cell surface antigen, as demonstrated by fluorescence microscopy. Furthermore, the inventors demonstrated that the pentabodies developed against flagellin bind to flaA protein, which plays a role in invading mammalian cells. SPR demonstrated that the $V_HH$ had low nanomolar affinity to the target. The $V_HH$ were also capable of preventing/disrupting *Campylobacter* growth and motility, as demonstrated in a motility assay. The $V_HH$ also significantly reduced the levels of *C. jejuni* colonization in chickens when orally administered. Additionally, studies of the combinatorial therapy of antibodies and antibiotics in the control of *Campylobacter* illustrate that the administration of the $V_HH$ and pentabodies can lower the required dose of antibiotics by up to 35-fold.

The present invention will be further illustrated in the following examples. However, it is to be understood that these examples are for illustrative purposes only and should not be used to limit the scope of the present invention in any manner.

Example 1: Preparation of Antigen

Flagella were prepared for use as the antigen in subsequent examples.

*C. jejuni* (strain 81-176) flagella were isolated as described previously (Power et al., 2003). Briefly, to prepare flagella, *C. jejuni* was cultured overnight and cells were scraped off into Muller-Hinton broth and incubated for overnight. Cells were then harvested by centrifugation and re-suspended in 100 mL of tris-buffered saline solution. Flagella were sheared from the cells using a Waring blender on ice. Cell debris was pelleted by centrifugation and the supernatant was transferred to an ultracentrifugation tube. Flagella were pelleted by centrifugation for 1 hour at 45,000 rpm. Further purification was done by re-suspension in 2% SDS and centrifugation of the samples. Pellets were re-suspended in 200-500 µL of dH$_2$O.

Example 2: Llama Immunization and Serum Response

To isolate V$_H$H that target the *C. jejuni* flagella, a llama was immunized with the flagella antigen obtained in Example 1.

A male llama (*Lama glama*) was immunized subcutaneously with *C. jejuni* flagella (Example 1). Seven injections were performed in total and, for each injection, 100 µg of antigen in a total volume of 0.5 ml was mixed with an equal volume of either complete (day 1) or incomplete (days 21, 35, 49, 63) Freund's adjuvant (Sigma). The last two injections (days 76 and 90) were performed with 100 µg of antigen without adjuvant. Preimmune blood (15-20 ml) was collected before the first injection and on days 21, 49, 76 and 90. The specific immune responses were analyzed by ELISA using total preimmune and immune sera. Llama serum from day 90 was fractionated according to Hamers-Casterman et al. (1993). Protein G and A columns (GE Healthcare) were used for serum fractionation according to the manufacturer's instructions and separated fractions were adjusted to pH 6 with 1 M Tris/HCl, pH 8.8, and dialyzed against pre-chilled PBS at 4° C. overnight. Individual heavy fractions (G1, A1 and A2) and G2 (conventional IgG) were analyzed for specific binding to flagella by ELISA. Briefly, microtitre plates (Maxisorp™ plates) (Nalge Nunc International, Rochester, N.Y.) were coated overnight at 4° C. with 5 µg/ml of flagella antigen (Example 1) in PBS. Wells were rinsed and blocked with 200 µl of 1% casein. Different dilutions of purified IgG fractions (G1, G2, A1 and A2) were added and incubated at room temperature for 1.5 h. Wells were washed with PBST (0.05% v/v Tween-20), and incubated with goat anti-llama IgG (H+L) (1:1,000 in PBS) (Bethyl Laboratories, Montgomery, Tex.) followed by Swine-anti-goat-HRP (1:3,000 in PBS) (Cedarlane, Burlington, ON, Canada). Signal was detected by adding 100 µl/well TMB peroxidase substrate (Kirkegaard and Perry Laboratories, Gaithersburg, Md., USA). Reactions were stopped by adding 100 1M phosphoric acid and A$_{450}$ was measured using a Bio-Rad ELISA plate reader.

SDS-PAGE confirmed the purity of the llama serum fractions (G1, G2, A1 and A2; data not shown). ELISA of the fractions showed strong immune responses in heavy chain as well as conventional fractions against flagella antigens when compared with pre-immune bleeding (data not shown). These results are also comparable with the ELISA results obtained from total serum (data not shown).

Example 3: Library Constructions and Selection of Flagella-Binding V$_H$H

A hyper-immunized llama V$_H$H library was constructed based on RNA isolated from the serum collected in Example 2.

Phage display library was constructed as described previously (Arbabi Ghahroudi et al., 2009). In brief, total RNA was isolated from approximately 1×10$^7$ lymphocytes collected on day 90 post-immunization using QIAamp RNA blood mini kit (Qiagen, Mississauga, Ontario, Canada). First-strand cDNA was synthesized with oligo(dT) primer using 5 µg total RNA as template according to manufacturer's recommendations (GE Healthcare) (Arbabi Ghahroudi et al., 2009). Variable and part of the constant domains DNAs were amplified using oligonucleotides MJ1-3 (sense) and two CH2 domain antisense primers CH2 and CH2b3 (for primer sequences see Arbabi Ghahroudi et al., 2009) and heavy chain fragments (550-650 bp in length) were gel-purified using QIA quick gel extraction kit (Qiagene). The variable regions of heavy chain antibodies (IgG2 and IgG3) were re-amplified in a second PCR reaction using MJ7 and MJ8 primers (for primer sequences see Arbabi Ghahroudi et al., 2009). The amplified PCR products were purified with a QIAquick PCR purification kit (Qiagene), digested with SfiI (New England BioLabs, Pickering, Ontario, Canada), and re-purified using the same kit. Twelve micrograms of digested V$_H$H fragments were ligated with 40 µg (3:1 molar ratio, respectively) Sfi-digested pMED1 phagemid vector (Arbabi Ghahroudi et al., 2009) using LigaFast Rapid DNA ligation system and its protocol (Promega, Madison, Wis.), transformed into commercial electrocompetent TG1 *E. coli* cells (Stratagene, La Jolla, Calif.) as described previously (Arbabi Ghahroudi et al., 2009) and a library size of 5×10$^7$ transformants was obtained. The V$_H$H fragments from 30 colonies were PCR-amplified and sequenced to analyze the complexity of the library; all clones had inserts of expected sizes and were different from each other at their CDR regions as determined by sequencing of their encoding V$_H$H fragments. The library was grown for 3-4 hours at 37° C., 250 rpm in 2× YT/Amp-Glucose (2% w/v) medium. The bacterial cells were pelleted, resuspended in the same medium and stored as glycerol stock at −80° C. as described previously (Arbabi Ghahroudi et al., 2009).

Panning experiments was essentially performed as described previously (Arbabi Ghahroudi et al., 1997 and 2009). Panning was performed for a total of four rounds against the flagella antigens. Two milliliters of the library stock was grown in for 1-2 hours at 37° C., 250 rpm in 2× YT/Amp-Glucose (2% w/v) medium (A$_{600}$=0.4-0.5), infected with M13KO7 helperphage (New England Biolobas) for 1 hour at 37° C. After centrifugation of the culture at 4° C., the infected cell pellets were resuspended in 200 ml of 2× YT/Amp with 50 µg/ml kanamycin and incubated overnight at 37° C. and 250 rpm. The phage particles in culture supernatant were PEG-precipitated as described previously (Arbabi-Ghahroudi et al., 2009) and the phage pellets were resuspended in 2 ml of sterile PBS and the phage titration was determined. 96-well Maxisorp™ plate was coated with 30 µg of flagella antigen overnight at 4° C. The wells were rinsed with PBS and blocked with PBS/1% (w/v) casein for 2 h at 37° C. Approximately 10$^{12}$ rescued phage particles were added to the blocked wells and incubated for 2 hours at 37° C. The wells were washed 5× with PBST (0.1% v/v Tween-20) and 5× with PBS. The bound phages were eluted with 0.1 M triethylamine, neutralized with 1M Tris-HCL, PH 7.4 and incubated with exponentially growing TG1 cells. After 30 min incubation at 37° C., the cells were superinfected with M13KO7 for additional 15 min and grown in 2× YT-Amp-Kan overnight at 37° C. Panning was continued for three more rounds following the same conditions except that antigen concentration was reduced to 20, 15, and 10 µg/well and washing was increased 7, 10 and 12× with PBS-T and PBS for the second, third and fourth rounds of panning, respectively.

After four rounds of panning, 48 randomly picked colonies were grown and subjected to phage ELISA screening as described previously (Arbabi Ghahroudi et al., 2009) except that 5 μg/ml of Flagella were coated onto microtiter plates. Positive clones include FlagV1M and FlagV6M (SEQ ID NO:8 and SEQ ID NO:13; FIG. 1), which are further studied herein.

Example 4: Expression and Purification of Monomeric $V_HH$ $V_HH$ against flagella identified in Example 3 were PCR amplified from the pMED1 phagemid vector with BbsI1-$V_HH$ forward primer and BamHI-$V_HH$ reverse primer (Table 1). The PCR fragments were digested with the BbsI and BamHI restriction enzymes and ligated into the similarly digested pSJF2H expression vector (Arbabi-Ghahroudi et al., 2009). Upon ligation, all plasmids were transformed into electrocompetent TG1 E. coli and selected on LB agar plates+ampicillin. Colonies were screened by colony PCR for inserts and the DNA sequenced.

$V_HH$ antibodies were expressed using the 5-day minimal media method (Arbabi-Ghahroudi et al., 2009). After induction of protein expression, cell cultures were harvested at 6,000 rpm×30 min (4° C.), the supernatant decanted, and the periplasmic contents extracted from the cell pellet. Briefly, the pellet of monomeric $V_HH$ was resuspended in 20 ml of ice cold TES (0.2 M Tris-HCl pH 8.0, 20% (w/v) sucrose, 0.5 mM EDTA) and incubated on ice for 30 min. Next, 30 ml of ice-cold 1/8 TES (diluted in dH$_2$O) was added, incubated an additional 30 min on ice, and the slurry centrifuged at 12,000 rpm for 30 min (4° C.). The resulting supernatant containing $V_HH$ was dialysed overnight into immobilized metal-affinity chromatography (IMAC) buffer A (10 mM HEPES pH 7.0, 500 mM NaCl) and purified as described (Arbabi-Ghahroudi et al., 2009). Purification of antibodies was done using HiTrap™ Chelating HP columns (GE Healthcare) according to the instruction. Fractionation was performed on an ÄKTA FPLC purification system (GE Healthcare) with 10 mM HEPES, 500 mM NaCl, pH 7.0 as the starting buffer and 10 mM HEPES, 500 mM NaCl, 500 mM imidazole, pH 7.0 as the elution buffer.

Purified protein fractions were pooled and dialyzed against PBS. Eluted fractions were analyzed by SDS-PAGE and Western blotting before being dialysed into PBS. $V_HH$ concentrations were determined by absorbance measurements at 280 nm using theoretical MW and extinction coefficients calculated with the ExPASy ProtParam Tool (http://expasy.org/tools/protparam.html) according to Pace et al., 1995. The yield of the purified monomeric FlagV1M and FlagV6M $V_HH$ ranged from 10 to 80 mg/l bacterial culture (FIG. 2).

Table 1, below, shows the primers used in the construction of monomeric and pentameric VHH clones, as described in Examples 4 and 5.

TABLE 1

Primers used in the construction of monomeric and pentameric $V_HH$ clones

| Name | Sequence 5'→3' |
|---|---|
| BbsI1-$V_HH$ forward primer | TATGAAGACACCAGGCCCAGGTAAAGCTGGAGGAGTCT (SEQ ID NO: 23) |
| BamHI-$V_HH$ reverse primer | TTGTTCGGATCCTGAGGAGACGGTGACCTG (SEQ ID NO: 24) |
| ApaI-$V_HH$ reverse primer | ATTATTATGGGCCCTGAGGAGACGGTGACCTGGGTC (SEQ ID NO: 25) |

Example 5: Expression and Purification of Pentameric $V_HH$

Pentamers of the monomeric $V_HH$ were prepared by fusing the $V_HH$ to the pentamerization domain of the B-subunit of an AB$_5$ toxin family. Once expressed, the subunits self-assemble with pentamers. FlagV1P and FlagV6P (SEQ ID NO:19 and SEQ ID NO:21; FIG. 1) were prepared.

$V_HH$ against flagella identified in Example 3 were PCR amplified from the pMED1 phagemid vector with BbsI1-$V_HH$ forward primer and ApaI-$V_HH$ reverse primer (Table 1). The PCR fragments were digested with the BbSI and ApaI restriction enzymes and ligated into the similarly digested pVT2 expression vector (Arbabi-Ghahroudi et al., 2009). Upon ligation, all plasmids were transformed into electrocompetent TG1 E. coli and selected on LB agar plates+ampicillin. Colonies were screened by colony PCR for inserts and the DNA sequenced.

Pentameric antibodies were expressed using the 5-day minimal media method (Arbabi-Ghahroudi et al., 2009). After induction of protein expression, cell cultures were harvested at 6,000 rpm×30 min (4° C.), the supernatant decanted, and the periplasmic contents extracted from the cell pellet. The cells were re-suspended in 100 ml of ice-cold lysis buffer (50 mM Tris-HCl, pH 8.0, 25 mM NaCl,) kept on ice at −20° C. overnight or frozen on dry ice for 1 h. One ml of 100 mM PMSF and 200 μl of 1M DTT were added to the frozen suspensions which were then thawed at room temperature with occasional shaking. Cells were lysed by adding 3 ml of freshly prepared lysozyme (final concentration=150 μg/ml). The suspensions were incubated at room temperature for 30-50 min with occasional shaking until they became viscous at which time 200 μl-300 μl of DNase I (Sigma) (15 units/μl in 1 M MgCl$_2$) were added followed by an additional 15 min at room temperature. Cell lysates were centrifuged and filtered through 0.22 μm membrane filters. The resulting supernatant containing $V_HH$ was dialysed overnight into immobilized metal-affinity chromatography (IMAC) buffer A (10 mM HEPES pH 7.0, 500 mM NaCl) and purified as described (Arbabi-Ghahroudi et al., 2009). Purification of antibodies was done using HiTrap™ Chelating HP columns (GE Healthcare) according to the instruction. Fractionation was performed on an ÄKTA FPLC purification system (GE Healthcare) with 10 mM HEPES, 500 mM NaCl, pH 7.0 as the starting buffer and 10 mM HEPES, 500 mM NaCl, 500 mM imidazole, pH 7.0 as the elution buffer.

Purified protein fractions were pooled and dialyzed against PBS. Eluted fractions were analyzed by SDS-PAGE and Western blotting before being dialysed into PBS. $V_HH$ concentrations were determined by absorbance measurements at 280 nm using theoretical MW and extinction coefficients calculated with the ExPASy ProtParam Tool (http://expasy.org/tools/protparam.html) according to Pace et al., 1995. The yield of the purified pentamers ranged from 10-50 mg/l bacterial culture.

Example 6: Biophysical Characterization of Anti-Flagella Antibodies

The FlagV1M, FlagV6M, FlagV1P, and FlagV6P antibodies expressed and purified in Examples 4 and 5 were characterized.

Surface Plasmon Resonance. Monomeric and pentameric FlagV1 and FlagV6 (Example 4) were passed through size exclusion columns, Superdex 75 and Superdex 200 (GE Healthcare), respectively, in 10 mM HEPES, pH 7.4, containing 150 mM NaCl, 3 mM EDTA. Monomeric $V_HH$ fractions were collected and protein concentrations determined by measuring $A_{280}$ measurements. 0.8 mg/ml of anti-flagellin $V_HH$ were biotinylated by mixing Pierce EZ-Link Sulfo-NHS-LC-LC-biotin (GE Healthcare) with approximately 10 folds molar excess in 10 mM phosphate, 150 mM NaCl, pH 7.0 for 30 min at room temperature followed by dialysis against the same buffer. Analyses were performed with a Biacore 3000 instrument (GE Healthcare). All measurements were carried out at 25° C. in 10 mM HEPES, pH 7.4, containing 150 mM NaCl, 3 mM EDTA and 0.005% surfactant P20 (GE Healthcare). Approximately 700-900 RUs of biotinylated flagellin were captured on SA sensor chip (GE Healthcare) at a flow rate of 5 µl/min. Various concentrations of the antibodies were injected over Flagellin-SA surfaces using an SA surface as a reference at a flow rate of 40 µl/min. Surfaces were regenerated by washing with running buffer. Data were analyzed with BIAevaluation 4.1 software.

Figure 3C:
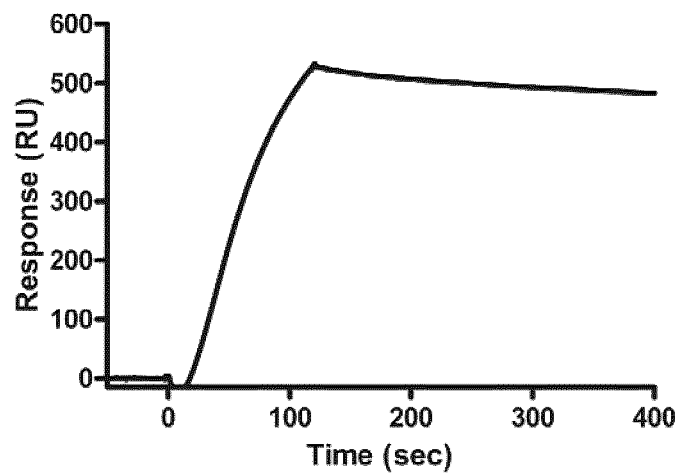

As flagella were sensitive to the acidic conditions used for immobilization on CM % sensor chips, the biotinylated antigen was captured on streptavidin. SPR results are shown in FIG. 3A-3C. All data sets showed reasonably good fitting to a 1:1 interaction model, allowing for the derivation of rate constants and affinities (shown in Table 2, below) which were in the range of in the range of 20-30 nM. FIG. 3C shows FlagV1P to have a very slow off rate compared to FlagV1M (FIG. 3A), showing an increase in functional affinity.

Antibody binding assays. ELISAs were performed as described in Example 2, except that after washing the plate with PBST and blocking with PBS-casein (1%), a 5 µg/ml solution of FlagV1M, FlagV1P, or FlagV6P was added to the respective wells and incubated for 1 hour at 37° C. Wells were washed with PBST (0.05% v/v Tween-20) and rabbit anti-His6 IgG conjugated to HRP (1:5000 in PBS) (Bethyl Laboratories) and incubated for 1 hour at room temperature. Binding was detected with TMB substrate (Kirkegaard and Perry Laboratories) and the reaction was stopped with 1M $H_3PO_4$ and $A_{450}$ was measured using an ELISA plate reader as described above.

ELISA results are shown in FIG. 2. FlagV1M showed strong binding activity by ELISA. As shown, 50% maximum binding was achieved at 0.2 µg/ml (15.6 nM) for FlagV1M, while pentamer FlagV1P achieved 50% maximum binding at 0.005 µg/ml (40 pM)—an almost 400× increase in functional affinity. The approximate affinity of FlagV1M obtained by ELISA (in the range of 20-30 nM) is in agreement with values obtained by SPR.

Epitope mapping. Flagella were prepared from Fla A and Fla B mutant strains of *C. jejuni* along with the whole cell lysate of wild type strain of 81-176 as described above. The flagella preparations were separated on 12.5% SDS-polyacrylamide gels under reducing conditions and transferred to nitrocellulose membrane. Membranes were blocked with 3% (w/v) BSA in PBS and reacted with FlagV1P pentabody for 1 hour at room temperature. After washing five times with PBST, membranes were incubated with either mouse anti-verotoxin followed by goat-anti-mouse AP conjugate or anti-His AP conjugates (diluted 1:5,000 in blocking buffer) (Abcam, Cambridge, Mass.). Finally, the membranes were washed four times and incubated with AP substrate (Bio-Rad) for 10 min. The AP reaction was stopped by rinsing the membranes with distilled $H_2O$ and air dried.

Figure 4:
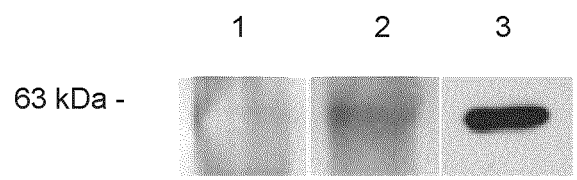
FIG. 4 illustrates the detection of the FlaA component of flagellin by the FlagV1P pentabody in a Western blot.

Results are shown in FIG. 4. FlagV1P bound the Fla A component of flagellin. Weak cross-reactivity was observed with Fla B, likely due to high DNA sequence identity (95%) between the Fla A and Fla B proteins (Wassenaar et al. 1991).

To determine whether FlagV1M and FlagV6M bound the same epitope, SPR co-injection experiments were conducted as described above. For both antibodies, 60-100 µl of each $V_HH$, at a concentration 50× its $K_D$ value, were injected over 600-700 RUs of immobilized flagella at 30 µl/min. Results are shown in FIG. 5. FlagV1M and FlagV6M appeared to bind distinct, non-overlapping epitopes since the signal approximately doubled with the second injection. This further suggests that a combination of both FlagV1 and FlagV6 monomer or pentamer might provide a higher efficiency of binding to the antigen, i.e. flagella and therefore, potentially better efficacy of antibodies in reducing the rate of *campylobacter* colonization.

FITC labelling of pentabodies and Fluorescence microscopy. FlagV1P and FlagV6P were labeled at a concentration of 2 mg/ml with FITC using the FITC-labeling kit from Invitrogen according the manufacturer's instruction. The labeled pentabodies were dialysed against PBS several times to remove unincorporated FITC. Wild-type *C. jejuni* 81176 and mutant cj1293 were fixed in log phase growth with 3% formalin overnight. The cells were washed with PBS to remove formalin, and then 10 µl was air dried onto glass coverslips at $\sim 1 \times 10^8$/ml. Non-specific binding was blocked with 50 µl 5% milk-PBS for 1 hour at room temperature. The cells were incubated for 1 hour at room temperature in 50 µl FITC-labeled FlagV1P diluted in PBS to 80 µg/ml. The cells were washed with PBS/0.1% Tween and then mounted onto glass slides with Vectashield-DAPI (Vector Laboratories, Burlington, Canada) mounting medium. The slides were examined with a Zeiss Axiovert 200M microscope (Zeiss, Toronto, Canada). Experiment was done in duplicate, on three independent occasions, with at least three fields of view on each coverslip imaged.

Results are shown in FIG. 6. The pentabodies specifically label *C. jejuni*, strain 81176, while no specific binding to *C. jejuni* (strain 1293) or *C. difficile* bacteria was detected. Binding of FlagV1P was demonstrated through fluorescence microscopy by which the antibody could be seen binding to the flagellar filaments located at the poles of *C. jejuni* 81-176 cells. Flagellins of *C. jejuni* 81-176 have been shown to be glycosylated with pseudaminic acid (Thibault et al., 2001) and inactivation of the gene pseB, which is involved in the biosynthesis of pseudaminic acid, renders cells unable to assemble flagellar filaments (Schoenhofen et al., 2006; Goon et al., 2003). As observed in FIG. 6 (panels e and f) disruption of this gene led to an inability of the FlagV1P to bind to the *C. jejuni* cells, confirming this binding is specific to the flagellar filaments.

In another experiment, fluorescence microscopy was performed essentially as described above except that *C. jejuni* strain 81-176, 81-176 flaA-flaB-, or *C. jejuni* strain 11168 was incubated with FITC-labeled FlagV1P or Flag V6P. Immunostaining with FITC-labeled rabbit anti-flagella polyclonal was used as positive control. Results in FIG. 7 show that FlagV1P binds to *C. jejuni* flagella of strain 81-176 while FlagV6P binds to the flagella of both 81-176 and 11168 strains. This demonstrates that FlagV6P antibody might interact with a wide range of flagella variants of *C. jejuni* strains.

Cross-reactivity ELISA. ELISA was used to determine the cross-reactivity of the purified anti-flagella pentamers (FlagV1P, FlagV6P) with nine different strains of *C. jejuni* (strains 81-176, P1, 11168, P4, P19, P36, P2, P3, and P64). All strains used were human clinical isolate except *C. jejuni* strain P2, which is a strain isolated from calf. Flagella were prepared from the different strains and used for coating of the microtiter plates in ELISA assays, as described in Example 2, except that wells were coated with 10 μg of *Campylobacter* flagella proteins from various strains and binding was detected using FlagV1P or FlagV6P pentabodies. Absorbance values indicate an average of two independent experiments.

Results are shown in FIG. 8. ELISA data showed that FlagV1P interacted strongly with 81-176 (the immunogen strain) and five other strains to different degrees, but did not bind strongly to 11168, P2, and P3 strains under the condition tested. These data suggest that co-application of both antibodies may provide a more effective product for preventing *C. jejuni* species and sub-species colonization.

Example 7: Preparation of Mutant $V_HH$ and Pentabodies

Altered antibodies were developed through random mutagenesis to have increased tolerance to gut enzymes, which allows them to resist the harsh environment of the chicken gastrointestinal tract. To do so, an error-prone library was constructed based on the FlagV1M $V_HH$. The work-flow diagram highlighting the construction of the $V_HH$ V1 error-prone PCR library, protease treatment of phages and panning scheme is shown in FIG. 15B.

Construction of the mutant V1 library by error-prone PCR. Before construction of the V1 error-prone PCR library, the protease-sensitive $His_6$/HA tags were removed from the pMED1 vector. The new vector was named pMED6 (FIG. 15A) and contained an amber "tag" stop codon 4 nucleotides downstream of the 5' SfiI restriction enzyme site where the previous $His_6$/HA tag was located. For error-prone PCR, 10 ng of FlagV1M DNA was used as the initial template and amplified in a 50 μl reaction using a random mutagenesis PCR kit (GeneMorph II Random Mutagenesis kit, Stratagene) and primers MJ7BACK and MJFOR 11 (Table 2) for 30 cycles (95° C. 30 s, 55° C. 30, 72° C. 60 s) followed by a 10 min extension at 72° C. The PCR products (about 500 bp in length) were purified with a QIAquick PCR purification kit (Qiagen, Mississauga, Ontario, Canada), digested with SfiI for 6 h at 50° C. (New England BioLabs, Pickering, Ontario, Canada) and re-purified using the same kit. 200 μg pMED6 vector was also digested overnight at 50° C. followed by a 2 h PstI/XhoI as described previously. The digested vector was purified with QIAquick PCR purification kit (Qiagene) and the DNA was eluted in sterile distilled $H_2O$ (Arbabi Ghahroudi et al., 2009). Forty-five micrograms of digested $V_HH$ fragments were ligated with 150 μg (3:1 molar ratio, respectively) SfiI-digested pMED6 phagemid vector (Arbabi Ghahroudi et al., 2009) using LigaFast Rapid DNA ligation system and its protocol (Promega, Madison, Wis.), transformed into commercial electrocompetent TG1 *E. coli* cells (Stratagene, La Jolla, Calif.) as described previously (Arbabi Ghahroudi et al., 2009) and a library size of approximately $2 \times 10^9$ transformants was obtained. The $V_HH$ fragments from 30 colonies were PCR-amplified and sequenced, demonstrating the presence of point mutation within the $V_HH$ amino acid sequence (data not shown). The library was grown for 3-4 h at 37° C., 250 rpm in 2× YT/Amp-Glucose (2% w/v) medium. The bacterial cells were pelleted, re-suspended in the same medium and stored as glycerol stock at −80° C. as described previously (Arbabi Ghahroudi et al., 2009).

Table 2, below shows the primers used in the construction of error prone PCR library, subcloning, and disulfide bond mutants. Methods utilizing these primer are described in Examples 7 and 10.

TABLE 2

Primers used in construction of error prone PCR library, subcloning, and disulfide bond mutants

| Name | Sequence 5'→3' | Purpose |
| --- | --- | --- |
| MJ7BACK | CAT GTG CAT GGC CTA GAC TCG CGG CCC AGC CGG CCA TGG CC (SEQ ID NO: 26) | EP-PCR |
| MJFOR 11 | CAT GTG TAG ATT CTG CCT GGC CGG CCT GGC C (SEQ ID NO: 27) | EP-PCR |
| BbsI1-$V_HH$ | TAT GAA GAC ACC AGG CCC AGG TAA AGC TGG AGG AGT CT (SEQ ID NO: 23) | Subcloning |
| BamHI-$V_HH$ | TTG TTC GGA TCC TGA GGA GAC GGT GAC CTG (SEQ ID NO: 24) | Subcloning |
| V1-DSB-for | TAG ACA GTA TTA TCC AGA TCC CGT GAA GGG CCG ATT CAC CTG CAC CAG AGA C (SEQ ID NO: 28) | DSB cloning |
| V1-DSB-rev | GGA TAA TAC TGT CTA TCT CTA CTC CAG GAA ATA GCG CAC ACT AC (SEQ ID NO: 29) | DSB cloning |

Protease-panning of the V1 error-prone PCR library. Panning experiments was essentially performed as described previously (Arbabi Ghahroudi et al., 1997; Arbabi Ghahroudi et al., 2009) except that rescued and amplified phages from the initial library and each round of panning were pre-treated with chicken GI tract fluid as well as pepsin, chymotrypsin and trypsin proteases. Three phage aliquots (125 µl each; 1×10¹² phage particles) were prepared in 1 mM Tris-HCl, pH 7.8 buffer. To the first phage aliquot, 12.5 µl GI tract chicken protease extract (10× dilution) was added and incubated for 2 h at 37° C. The second phage aliquot was incubated with equimolar mixture of chymotrypsin/trypsin (Roche) (R1: 2.5 µM of each protease, R2: 7.5 µM, and R3-4: 10 µM) in 1 mM HCl plus 20 mM $CaCl_2$ and incubated for 15 min (R1), 45 min (R2), and 60 min (R3-4). Similarly, different concentrations of pepsin (Roche) was prepared in PBS (R1: 2.5 µM, R2: 7.5 µM, R3-4 10 µM) and 1/10 volume of 100 mM HCl pH 2.0 to the 125 µl phage aliquot. The protease reaction was stopped either by adding 12.5 µl of protease inhibitor cocktail (Roche) for chicken protease and trypsin/chymotrysine or by adding ½ volume of 1 M Tris-HCl, pH 7.5 for pepsin.

The protease-treated phage aliquots were mixed and used for panning. A total of four rounds of panning were performed against flagella as described previously (Arbabi Ghahroudi et al., 2009). Briefly, wells of a 96-well Maxisorp™ plate (Nunc) were coated with 15 µg of flagella or PBS (as a blank) overnight at 4° C. The wells were rinsed with PBS and blocked with PBS/1% (w/v) casein for 2 h at 37° C. Mixed protease-treated phage particles (100 µl contain approximately 10¹¹ pfu) were added to the blocked wells and incubated for 2 h at 37° C. The wells were washed 6× with PBST (0.1% (v/v) Tween-20) and 6× with PBS. The bound phages were eluted with 0.1 M triethylamine, neutralized with 1 M Tris-HCl, pH 7.4 and incubated with exponentially growing TG1 *E. coli* cells. After 30 min incubation at 37° C., the cells were superinfected with M13KO7 for additional 15 min and grown in 2× YT-Amp-Kan overnight at 37° C. Panning was continued for three more rounds following the same conditions except that antigen concentration was reduced to 12.5, 10, and 10 µg/well and washing was increased 7, 10 and 12× with PBS-T and PBS for the second, third and fourth rounds of panning, respectively. After four rounds of panning, 24 randomly picked colonies were subjected to colony PCR and the PCR fragments were sequenced. A total of 9 anti-flagella $V_HH$ with 1-4 point mutations were identified. The mutant clones along with the parental V1 clone were grown and subjected to phage ELISA screening as described previously (Arbabi Ghahroudi et al., 2009) except that 5 µg/ml of flagella were coated onto microtiter plates.

In order to select phage antibodies resisting the chicken GI tract environment during panning, the phage antibodies were pre-incubated with either chicken GI tract fluids harboring various proteases or with the major GI proteases, namely, pepsin, trypsin and chymotrypsin (FIG. 15B). The filamentous phages (f1, fd, and M13) are known to be resistant to most GI tact fluid proteases and phage display, therefore, is an ideal display platform to select resistant $V_HH$ single domain antibodies. After panning, 9 different $V_HH$ were isolated; however, less than half of these clones turned out to be positive in phage ELISA assay (FIG. 15C). Following sub-cloning of the positive $V_HH$ in monomeric and pentameric expression vectors (pSJF2 and pVT2, respectively), only clone FlagV1F23M had a comparable ELISA signal and expression level to the parental V1 clone; other clones either turned out to be weak binders or had poor expression. The sequencing data showed that the only difference between FlagV1M $V_HH$ and FlagV1F23M is located in two residues (Lys→Gln at position 3, Glu→Val at position 5, IMGT numbering system) in framework 1. The FlagV1F23 clone was then expressed as a monomer and pentamer (SEQ ID NO:9 and SEQ ID NO:20; FIG. 1). The same mutations were applied to the FlagV6 antibody (using appropriate primers), yielding FlagV6F23M and FlagV6F23P (SEQ ID N0:14 and SEQ ID NO:22; FIG. 1).

Expression and purification of soluble and pentameric $V_HH$. FlagV1F23M, FlagV1F23P, FlagV6F23M, and FlagV6F23P were expressed and purified as described in Examples 4 and 5, as appropriate.

Example 8: Motility Assays

Inhibition of *Campylobacter* growth and motility by $V_HH$ and $V_HH$ pentabodies was studied using standard plate assay.

The motility assay was performed as described previously (Kalmokoff et al., 2006). Antibodies, at a final concentration of 0.25-1 µg/µl, were incubated with *C. jejuni* (strain 81-176) or *C. coli* (5×10⁷ CFUs) at RT for 30 minutes. The mixtures were plated in the center of a petri dish containing Muller-Hinton agar (0.4%) and incubated at 37° C. under microaerophilic conditions (5% $O_2$, 10% $CO_2$, and 85% $N_2$). Bacterial motility was determined by measuring the diameter of the circle produced by the growing bacteria at 24, 48, and 72 hrs after plating the bacteria. The cross-reactivity of the antibodies with *S. enterica* serovar *typhimurium* was also tested using the methods as just described. To test whether the combination of antibodies with antibiotics can further disrupt the motility, different concentration of tetracycline (0-64 µg/ml) were added to the culture plates in the presence of 1 µg/µl of FlagV1P, with the remainder of the assay performed as just described.

Results are shown in FIG. 9 and Table 3. *Campylobacter* strain 81-176 co-incubated with FlagV1M, FlagV1P, FlagV6P, or a combination of FlagV1P and FlagV6P showed a marked reduction in the bacterial motility. Another commonly used strain of *Campylobacter*, strain 11168 was also examined and demonstrated motility inhibition on plate assay with FlagV6P. Both FlagV1M and FlagV1P remained functional even after 48 hrs of incubation.

Table 3, below, illustrates *C. jejuni* 81-176 and 11168 motility on plates after incubation with FlagV1 and FlagV6 monomers and pentamers. The diameter of the circles representing the spread of bacteria from the inoculum site was measured. Asterisk indicates statistical significance of FlagV1 and FlagV6 antibody treatments vs the control unrelated pentabody.

TABLE 3

*C. jejuni* motility after incubation with FlagV1 and FlagV6 monomers and pentamers

| | Strain 81-176 | | Strain 1168 |
|---|---|---|---|
| Treatment | diameter (mm) ± SD - 24 h | diameter (mm) ± SD - 48 h | diameter (mm) ± SD - 24 h |
| PBS | 26.6 ± 2.25 | 82 ± 3.3 | 19.5.3 ± 1.5 |
| Unrelated pentabody | 24 ± 2.7 | 67.3 ± 4.5 | 20.2 ± 2.22 |
| FlagV1M | 8.6 ± 1.25* | 19.5 ± 0.5* | 18 ± 0.83 |
| FlagV1P | 8.8 ± 0.76* | 45.16 ± 5* | 16.8 ± 1.35 |
| FlagV6P | 8.75 ± 0.35* | 45.5 ± 14.08 | 12 ± 0.95* |
| FlagV1P + FlagV6P | 9 ± 1.32* | 28 ± 3.04* | 13.2 ± 0.66* |

The effect of a combination of FlagV1P and antibiotics on the motility of *C. jejuni* (strain 81-176) is shown in FIG. 10. The top row illustrates bacterial growth when treated with the control buffer while the bottom row represents the bacteria treated with FlagV1P pentabody at a concentration of 1 µg/µl. Plates contained an increasing concentration of tetracycline: 0 μg/ml (A), 4 μg/ml (B), 16 μg/ml (C) and 64 μg/ml (D). Pictures were taken after 24 h of incubation. Addition of FlagV1P pentabody enhances the effect of tetracycline on *Campylobacter* motility by approximately 35-fold.

Results of motility assays on pentabodies FlagV1P-treated *Campylobacter coli* and *Salmonella typhimurium* are shown in FIGS. 11A and B, respectively. The bacterial growth of *C. coli* strain VC167 (A) and *S. enterica* serovar *typhimurium* (B) were measured at various time points. Antibodies were used at a concentration of 1 μg/ul. None of the pentabodies appears to affect motility of *Salmonella*. Results of cross-reactivity of the pentabodies FlagV1P and FlagV6P with *C. coli* VC167 are also shown in Table B.

Table 4, below, provides the results of motility assays showing the cross-reactivity of the pentabodies FlagV1P and FlagV6P with *C. coli* VC167. Significant reduction in motility of *C. coli* was noticed with FlagV6P pentabody. The values were subjected to the Student's t-test for statistical analysis. *p value<0.05; **p value<0.005

TABLE 4

Motility assays showing cross-reactivity of pentabodies FlagV1P and FlagV6P with *C. coli* VC167

| Treatment | diameter (mm) ± SD - 24 h | diameter (mm) ± SD - 48 h | diameter (mm) ± SD - 72 h |
| --- | --- | --- | --- |
| PBS | 12.5 ± 0.5 | 25.3 ± 1.52 | 43.6 ± 4.5 |
| FlagV1P | 10.6 ± 0.6* | 22 ± 3 | 42.3 ± 4.1 |
| FlagV6P | 5.6 ± 0.66** | 11.5 ± 1.32** | 25.6 ± 3.05** |

Example 9: Pathogen Localization and Treatment of Chickens

Inhibition of *C. jejuni* colonization in the chicken gut using anti-flagella $V_HH$ monomer or pentamer is investigated as an alternative approach to prevent *campylobacter* outbreaks. Flagella of *C. jejuni* is a virulence factor that mediates the bacterial colonization in the cecum of chicken GI tract. Therefore interruption of flagella motility through binding to antibodies is proposed to interfere with the bacterial motility and proliferation in the gut.

*C. jejuni* colonization and treatment of leghorn chicks. Inoculates for chick colonization experiments were prepared by harvesting *C. jejuni* 81-176 bacteria grown for 18 h in a phosphate buffered saline solution. Bacterial cells were diluted in PBS and maintained on ice until immediately before use. The viable cell count was determined by plating serial dilutions onto Karmali agar (Bacto). One-day old specific pathogen free (SPF) leghorn chicks (mixed sex) were obtained from the hatchery at the Canadian Food Inspection Agency, Ottawa, Canada. They were randomly assigned into negative control, positive control, and treatment groups, weighed, ID tagged and housed in animal containment units and provided with feed and water ad libitum. The units were housed in an environmentally controlled level 2 bio-containment room. On arrival 10% of the birds were randomly tested for colonization by *C. jejuni*. On day two, positive control and treatment groups were orally challenged with 300 μl *C. jejuni* 81-176 $10^8$ cfu/ml in PBS. Positive control groups received 300 μl PBS and treatment groups (n=28/group, 14 chickens in each of 2 containment units) received 300 μl of FlagV1P or FlagV1F23P at 1 h, 24 h and 48 h after the challenge. An uninfected, negative control group was also included (n=15).

At 1 h or 4 h, or 48 h after antibody treatment, birds were euthanized by cervical dislocation according to the approved guidelines of the Canadian Council for Animal Care. Ceca were aseptically collected for qualitative as well as quantitative assessment of colonization. Cecal contents were serially plated onto Karmali agar (Oxoid) and *C. jejuni* counts were done after incubation for 2 days at 37° C. under microaerophilic conditions. The chicken body weight was also measured on day 1 and 4 after challenging with *C. jejuni* alone or following pentabody administration. PBS was used as control and body weights (in grams) were measured at day one and day four.

FIGS. 12A and 12B show the effect of oral administration of FlagV1P or FlagV1F23P on the pathogen levels in *Campylobacter jejuni*-colonized chickens. At 1 h, 24 h and 48 h after challenge with *C. jejuni*, chickens received 300 μl pentameric wild type FlagV1P or mutant FlagV1F23P. Bacterial burdens in the individual ceca show significant reductions in the pentabody-treated chickens (FIGS. 12A and 12B). The negative control group showed no detectable *C. jejuni* in the ceca of uninfected chickens.

The effect of gavaged FlagV1P on chicken body weight was investigated by weighing the chickens one day and four days after challenging with *Campylobacter* alone or when pentabodies were administered orally. PBS was used as control. The average body weight±standard deviation of the values obtained from 28 replicates is shown in FIG. 13 for each group; no significant difference was found between the groups.

Pentamer localization in Chicken GI Tract by Sandwich ELISA. Chickens were gavaged with 1 mg of FlagV1P pentabodies according to the schedule described for colonization and treatment (see above section). Wells of a Maxisorp 96-microtiter plate (Nunc) were coated with mouse monoclonal anti-verotoxin antibodies (10 μg/ml) overnight at 4° C. After blocking with PBS-casein (1%), collected intestinal fluids from cecum, ileum, jejunum and duodenum were added to the wells in 2-fold serial dilutions (1/2-1/2048) and the plate was incubated at 37° C. for 1 hour. Wells were then washed with PBST (0.05% v/v Tween-20); rabbit anti-His6 IgG conjugated to HRP (1:5000 in PBS) were added (100 μl/well) (Bethyl Laboratories) and incubated for 1 hour at room temperature. Binding was detected with TMB substrate (Kirkegaard and Perry Laboratories) and the reaction was stopped with 1M $H_3PO_4$. $A_{450}$ was measured using an ELISA plate reader as described in Example 2. Data are presented as means±SEM for each group, unless otherwise specified. Differences in tissue bacterial burdens were assessed by Student's t test or one-way analysis of variance (ANOVA) followed by Bonferroni's post-hoc multiple comparison tests, when appropriate. Differences were considered significant when p<0.05.

Intestinal fluids were collected from cecum, ileum, jejunum and duodenum to examine for the presence of gavaged pentabodies. FIG. 14 shows the detection of anti-*C. jejuni* FlagV1P in different parts of chicken intestinal track. As shown, on average, there is a relatively high concentration of FlagV1P in cecum. It is noteworthy to mention that the principal site of *Campylobacter jejuni* colonization is the cecum, large intestine and cloaca (Beery et al., 1988; Carrillo et al., 2005). This data suggest a co-localization effect of pentabodies in GI tract and site of *campylobacter* colonization.

Example 10: Preparation of Disulfide Mutant $V_HH$ $V_HH$ as described above were constructed to include an additional disulfide bridge engineering, which may further increase tolerance to enzymes found in the chicken gastrointestinal tract.

Construction of disulfide-bond mutant $V_HH$. An additional disulfide bond was introduced into the core of FlagV1M and FlagV1F23M by mutating residues at positions 54 and 104 to cysteine using splice-overlap extension PCR, essentially as described elsewhere (Hussack, 2011). To create FlagV1MDSB, which contains 2 disulfide bonds, FlagV1M was amplified using BbsI1-$V_H$H/V1-DSB-rev and V1-DSB-for/BamHI-$V_H$H primer sets (Table 2). Likewise, FlagV1F23MDSB was created by amplifying FlagV1F23M with F23-DSB-for/V1-DSB-rev and V1-DSB-for/BamHI-$V_H$H primer sets (Table 2). All were cloned into the pSJF2H expression vector and transformed into TG1 *E. coli* as described in Example 3. FlagV1MDSB and FlagV1F23MDSB (SEQ ID NO:30 and SEQ ID NO:31, respectively; FIG. 1) were expressed and purified as described in Example 4.

An additional disulfide bond was also introduced into the core of FlagV6M and FlagV6F23M, using methods as described above. The resulting constructs were dubbed FlagV6MDSB and FlagV6F23MDSB (SEQ ID NO:32 and SEQ ID NO:33, respectively; FIG. 1).

Analysis of the disulfide mutants by SDS-PAGE showed that FlagV1MDSB and FlagV1F23MDSB ran at their expected molecular weights and there were no signs of high-order multimers on the non-reducing gel (FIG. 16A). $V_H$H yields ranged from 9.5 mg/l (V1-DSB) to 21.0 mg/l (Table 2).

Size-exclusion chromatography and surface-plasmon resonance (SPR) analyses of disulfide bond mutants. Size-exclusion chromatography (SEC) was performed prior to SPR analysis using a Superdex 75 column and ~50 µM of $V_H$H (FlagV1M, FlagV1MDSB, FlagV1F23M, or FlagV1F23MDSB), as described previously (Hussack, PLoS ONE, 2011). Prior to SPR analysis on a Biacore 3000 (GE Healthcare), flagellin from *C. jejuni* strain 81-176 was biotinylated using EZ-Link Sulfo-NHS-Biotinylation kit (Thermo Scientific). 500 mL of flagellin A was prepared (Example 1) and used at a concentration of 1 mg/ml. Biotin was used at 20× molar concentration and according to the instruction provided by the manufacturer. Unincorporated biotin was removed by dialysis against 1000× volume of PBS for a total of 8 times. The running buffer for all SPR experiments was HBS-EP (10 mM HEPES, 150 mM NaCl, 3 mM EDTA, pH 7.4, 0.005% P20; GE Healthcare). For binding analysis, 2000 response units (RUs) of biotinylated flagella was immobilized onto a CAP sensor chip (GE Healthcare) previously loaded with the biotin CAPture reagent (50 µg/ml in HBS-EP buffer; GE Healthcare). $V_H$H eluted from the SEC column were injected over the immobilized flagella at concentrations ranging from 25-400 nM, using multiple injections of increasing concentrations. The surface was stripped after each $V_H$H using regeneration buffers (8 M guanidine hydrochloride and 1 M NaOH) and a fresh biotinylated flagella surface prepared as described above. Affinities ($K_D$s) were calculated using the BiaEvaluation 4.1 software updated with the single-cycle kinetics package.

Wild-type $V_H$H comprise a canonical disulfide bond at positions 23/104 (IMGT numbering). The introduction of an additional, non-canonical disulfide bond at positions 54/78 (IMGT numbering) into FlagV1M and FlagV1F23M variant gave disulfide mutants FlagV1MDSB and FlagV1F23MDSB. Soluble bacterial expression of the disulfide mutants yielded up to 23 mg/L $V_H$H. The affinity of the $V_H$H was determined by SPR using single-cycle kinetics. The sensorgrams and affinities of FlagV1M, FlagV1MDSB, FlagV1F23M, or FlagV1F23MDSB are shown in FIG. 16B and reported in Table 2. All of the $V_H$H s fit a 1:1 binding model and retained high affinity binding to *C. jejuni* flagella, with $K_D$ ranging from 23.9 nm (FlagV1M) to 17.3 nM (FlagV1F23MDSB). SEC chromatograms are shown (FIG. 16C) confirming all $V_H$H s were monomeric (Table 2). The elution volumes ($V_e$) are noted on each chromatogram.

Thermal unfolding analysis of $V_H$H. The thermal unfolding mid-point temperature ($T_m$) of all $V_H$H was determined using circular dichroism spectroscopy at pH 7.3 and pH 2.0 using a Jasco J-815 spectrophotometer (Jasco, Easton, Md.) by following $V_H$H unfolding at 215 nm, essentially as described (Hussack, PLoS ONE, 2011), except that data points were obtained every 0.2° C. $V_H$H unfolding was measured using protein concentrations of 50 µg/mL, except in the case of the V1 $V_H$H where 10 µg/ml was used for $T_m$ determination at pH 7.3 because of aggregation at high temperatures using 50 µg/ml.

Unfolding curves with a single-phase transition were obtained for all $V_H$H at pH 7.3. At this pH, the $T_m$ of disulfide mutant $V_H$H was higher than $V_H$H with a single disulfide bond. For example, the $T_m$ of FlagV1MDSB and FlagV1F23MDSB were 79.10±0.11° C. and 80.19±0.12° C., respectively, compared to 61.65±0.38° C. and 72.33±0.15° C. for FlagV1M and FlagV1F23M, respectively (FIG. 17; Table 2). It should be noted that FlagV1M aggregated at temperatures above 68° C. (FIG. 17, inset) when tested at 50 µg/ml; however, when the concentration was reduced to 10 µg/ml, no aggregation was detectable at higher temperatures and a single-phase unfolding curve was obtained. Next, the $T_m$ of $V_H$H were determined at pH 2.0. Before performing unfolding experiments, $V_H$H were incubated for at least 2 h at pH 2.0. As is evident from the unfolding plots in FIG. 17, V1 was completely unfolded at the starting temperature (25° C.) at pH 2.0 and a $T_m$ could not be determined. In contrast, FlagV1MDSB was folded at 25° C., pH 2.0 and a $T_m$ of 42.41±0.11° C. was determined, illustrating the significant impact the second disulfide bond has on FlagV1MDSB stability. The FlagV1F23M was partially unfolded at 25° C., pH 2.0 and a $T_m$ of 30.51±0.26° C. was determined, an improvement from FlagV1M. This result underscores the success of the protease-panning strategy in selecting for more stable binders. Similar to neutral pH, the clone with the highest $T_m$ at pH 2.0 was F23-DSB, with a $T_m$ of 44.55±0.03° C., suggesting the effects of the stabilizing mutations in FlagV1F23M and the effects of the second disulfide bond were partially synergistic in creating the hyper-stabilized FlagV1F23MDSB domain.

In vitro protease digestions of $V_H$H. FlagV1M, FlagV1MDSB, FlagV1F23M, and FlagV1F23MDSB $V_H$H were subjected to in vitro protease digestion assays with the major GI proteases pepsin (Sigma), trypsin (Roche), and chymotrypsin (Roche). $V_H$H digestions were performed exactly as described (Hussack, PLoS ONE, 2011) and analyzed by SDS-PAGE thereafter. Briefly, $V_H$H were digested with 100 µg/mL of pepsin for 60 min at 37° C., pH 2.0; control $V_H$H was incubated in the absence of pepsin. For trypsin and chymotrypsin digestions, $V_H$H were incubated with 10 µg/mL of protease for 60 min at 37° C., pH 7.3; control $V_H$H were incubated in the absence of protease. Digested $V_H$H and controls were separated by SDS-PAGE and densitometric analysis of the SDS-PAGE gels was performed. A total of 3 independent protease digestions were performed on each $V_H$H.

Results are shown in FIG. 18. Both FlagV1M and FlagV1F23M were susceptible to pepsin degradation, with 22.3±8.1% and 6.8±3.6% of $V_H$H remaining intact after 60 min, respectively. The disulfide-engineered variants were considerably more resistant to pepsin, with FlagV1MDSB showing complete resistance (100.5±6.7%) at the concentration of pepsin tested (100 μg/ml). FlagV1F23MDSB was also very resistant to pepsin, with 96.9±15.8% of the $V_HH$ remaining intact after 60 min. When digested with trypsin for 60 min, F23 was completely resistant (101.1±4.7%) followed by V1 (84.4±1.8%), FlagV1F23MDSB (49.1±15.4%) and FlagV1MDSB (41.3±2.7%). It is evident that the addition of the disulfide bond reduces trypsin resistance for both clones here. When digested with chymotrypsin for 60 min, FlagV1F23MDSB displayed the highest resistance (90.9±4.1%) followed by FlagV1F23M (85.4±3.3%), FlagV1M (52.9±6.5%), and FlagV1MDSB (49.5±6.7%). Therefore, the impact of the second disulfide bond does not increase chymotrypsin sensitivity but does increase trypsin sensitivity. Collectively, these data illustrates that the FlagV1F23M variant isolated from protease-panning has been selected for very high trypsin and chymotrypsin resistance or tolerance. Improved resistance to pepsin, trypsin and chymotrypsin degradation are desirable features for polypeptides that may be provided for oral administration.

In addition to individual protease digestions, a sequential digestion reaction was performed (see FIG. 19A) to mimic sequential protease digestion in the GI tract. $V_HH$ (50 μg) were first digested with pepsin (37° C., pH 2.0, 10 μg/ml final) for 15 or 30 min, followed by digestion with trypsin+chymotrypsin (37° C., pH 7.4, 10 μg/ml final for each) for 15 or 30 min, in a total volume of 50 μl. After the pepsin digestion, the pH of the reaction was neutralized with 1 M NaOH. After the trypsin+chymotrypsin digestion, protease inhibitor cocktail (Sigma) was added to stop the reaction. Sequentially digested $V_HH$ were compared to non-treated controls by SDS-PAGE.

The effect of the sequential digestions and non-treated controls by SDS-PAGE is shown in FIG. 19B. Near complete digestion of FlagV1M is evident at 15 and 30 min relative to control FlagV1M (compare "V1" to "V1(15)" and "V1(30)"). FlagV1F23M was more resistant than FlagV1M, with a strong band present after the sequential 15 min digest (compare "F23" to "F23(15)"). After 30 min, near-complete digestion of FlagV1F23M was found. Conversely, both disulfide-bond variants were strongly resistant to the sequential protease digestions, even after 30 min of treatment (compare "V1-DSB" to "V1-DSB(30)" and "F23-DSB" to "F23-DSB(30)"). Densitometry analysis of the bands revealed 74.5% of FlagV1F23MDSB $V_HH$ intact after the sequential 30 min digest compared to 47.6% of FlagV1MDSB $V_HH$ intact after the same treatment.

*C. jejuni* motility assay on protease-digested $V_HH$. Motility assay was performed as described previously (Kalmokoff et al, 2006). Antibodies, at a final concentration of 1 μg/ul, were incubated with *C. jejuni* ($5\times10^4$ CFUs) at RT for 30 minutes. The mixtures were plated in the center of a petri dish containing Muller-Hinton agar (0.4%) and incubated at 37° C. under microaerophilic conditions (5% $O_2$, 10% $CO_2$, and 85% $N_2$). Bacterial motility was determined by measuring the diameter of the circle produced by the growing bacteria at 24 hrs after plating the bacteria.

*C. jejuni* motility assay on protease-digested $V_HH$ mutants. $V_HH$ were exposed to a sequential protease digestion scheme as just described in the section above. The motility assay was then performed as described previously (Kalmokoff et al., 2006). Antibodies, at a final concentration of 1 μg/μl, were incubated with *C. jejuni* (strain 81-176) ($5\times10^4$ CFU) at RT for 30 minutes. The mixtures were plated in the center of a petri dish containing Muller-Hinton agar (0.4%) and incubated at 37° C. under microaerophilic conditions (5% $O_2$, 10% $CO_2$, and 85% $N_2$). Bacterial motility was determined by measuring the diameter of the circle produced by the growing bacteria at 24 hrs after plate inoculation.

The $V_HH$ were used in motility assays to determine if the sequentially-digested $V_HH$ were still functional in reducing *C. jejuni* motility (as depicted in FIG. 19C and FIG. 20). The $V_HH$ untreated with proteases remained effective in inhibiting the growth and spread of the bacteria on the plate after incubation for 24 hrs. The protease-treated FlagV1M and FlagV1F23M antibodies lost activity almost entirely after both 15 min and 30 min incubation conditions. In contrast, the growth-inhibiting activity of FlagV1MDSB and FlagV1F23MDSB mutants was almost unaffected by the protease treatment, further confirming the protease-treated $V_HH$ remain active and functional in the disulfide bond mutants.

Table 5, below, shows biophysical properties of *C. jejuni* flagella-specific $V_HH$. Rate and affinity constants, or "on" and "off" rates ($k_a$ or $k_{on}$ and $k_d$ or $k_{off}$), and resistance to gut enzymes pepsin, trypsin, and chymotrypsin are included. [a]Determined by Superdex 75 size-exclusion chromatography peak area integration; [b]10 μg/ml used due to aggregation of V1 at 50 μg/ml; [c]Digestions performed using 100 μg/ml protease; [d]Digestions performed using 10 μg/ml protease; n/a: proteins denatured at pH 2.0, 25° C.

TABLE 5

Biophysical properties of *C. jejuni* flagella-specific $V_HH$

|  | V1M | V1-DSB | F23 | F23-DSB | V6M |
|---|---|---|---|---|---|
| Yield (mg/l) | 17.0 | 9.5 | 21.0 | 16.5 | 20 |
| SEC (% monomer)[a] | 96.88 | 99.34 | 99.83 | 99.88 | 99.10 |
| $k_a$ ($M^{-1} s^{-1}$) | $2.36 \times 10^5$ | $1.53 \times 10^5$ | $2.29 \times 10^5$ | $1.65 \times 10^5$ | $1 \times 10^6$ |
| $k_d$ ($s^{-1}$) | $5.63 \times 10^{-3}$ | $2.80 \times 10^{-3}$ | $4.26 \times 10^{-3}$ | $2.86 \times 10^{-3}$ | $3 \times 10^{-2}$ |
| $K_D$ (nM) | 23.9 | 18.2 | 18.6 | 17.3 | 25.0 |
| $T_m$ pH 7.3 (° C.) | 61.65 ± 0.38[b] | 79.10 ± 0.11 | 72.33 ± 0.15 | 80.19 ± 0.12 | nd |
| $T_m$ pH 2.0 (° C.) | n/a | 42.41 ± 0.11 | 30.51 ± 0.26 | 44.55 ± 0.03 | nd |
| Pepsin resistance (%)[c] | 22.3 ± 8.1 | 100.5 ± 6.7 | 6.8 ± 3.6 | 96.9 ± 15.8 | nd |
| Trypsin resistance (%)[d] | 84.4 ± 1.8 | 41.3 ± 2.7 | 101.1 ± 4.7 | 49.1 ± 15.4 | nd |
| Chymotrypsin resistance (%)[d] | 52.9 ± 6.5 | 49.5 ± 6.7 | 85.4 ± 3.3 | 90.9 ± 4.1 | nd |

It is clear that single-domain $V_HH$ antibodies are emerging as novel tools against bacterial and viral infections. The small size of these polypeptides permits binding to epitopes that are inaccessible to conventional antibodies. Unique physical properties, such as resistance to proteolysis, denaturation and aggregation also allow applications in oral delivery therapeutics for human or livestock.

As described herein, phage display technology was used to construct and screen a library of $V_HH$ antibodies against *C. jejuni* flagella. It was demonstrated that the $V_HH$ and the pentameric versions thereof were able to bind to the antigen, and were effective in lowering *C. jejuni* loads in chickens when administered orally.

In vitro studies indicated that FlagV1M bound and disrupted the growth of *Campylobacter jejuni* on a plate assay, but was ineffective on a closely related strain of *Campylobacter* (*C. coli*). Both FlagV1M and FlagV1P were effective in disrupting the growth of bacteria in the motility assay at the concentrations used. Without wishing to be bound by theory, the mode of action could be through agglutination and/or intercalating of the $V_HH$ into a protein cavity causing disruption of the bacterial motility.

To determine the efficacy of the antibody in reducing *campylobacter* colonization, the pentameric version of the flagellin-specific $V_HH$ was constructed and used in the chicken studies on the assumption that the bacterial cells would become agglutinated by the $V_HH$ domains of the pentabodies, and this would impair the ability of *C. jejuni* to colonize the chicken gastrointestinal tract. The motility of *Campylobacter* is required for colonization of the viscous intestinal mucous, and the flagellin protein is the immunodominant antigen on the cell surface.

The protease-resistant and multimeric forms of the antibody or fragment thereof described above will advantageously reduce the colonization of *Campylobacter* in the chicken, for example, in the cecum. The technology described provides a new tool for controlling *Campylobacter* contamination.

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations of the particular embodiments described are encompassed herein, as would be evident to those of skill in the art.

REFERENCES

All patents, patent applications and publications referred to herein and throughout the application are hereby incorporated by reference.

Alfredson D. A., and Korolik V. 2007. Antibiotic resistance and resistance mechanisms in *Campylobacter jejuni* and *Campylobacter coli*-Review. FEMS Microbiol Lett. 277(2): 123-32.

Arbabi Ghahroudi, M. Desmyter A, Wyns L, Hamers R., and Muyldermans S (1997) Selection and identification of single domain antibody fragments from camel heavy-chain antibodies, FEBS Lett 414, 521-526.

Arbabi-Ghahroudi, M., Tanha, J., and Mackenzie, R. 2009. Isolation of monoclonal antibody fragments from phage display libraries. Methods Mol. Biol. 502: 341-64.

Beery J. T., Hugdahl M. B., and Doyle M. P. 1988. Colonization of gastrointestinal tracts of chicks by *Campylobacter jejuni*. Appl Environ Microbiol. 54(10):2365-70.

Behring, E. A. and Kitasato, S. 1890. Ueber das zustandekommen der diptherie-immunität und der tetanus-immunität bei thieren. Deutch. Med. Woch. 49, 1113-1114.

Bell, A., Wang, Z. J., Arbabi-Ghahroudi, M., Chang, T. A., Durocher, Y., Trojahn, U., Baardsnes, J., Jaramillo, M. L., Li, S., Baral, T. N., O'Connor-McCourt, M., Mackenzie, R. and Zhang, J. Differential tumor-targeting abilities of three single-domain antibody formats. Cancer Lett. 289, 81-90 (2010).

Blaser M J, Perez G P, Smith P F, Patton C, Tenover F C, Lastovica A J, Wang W I. 1986. Extraintestinal *Campylobacter jejuni* and *Campylobacter coli* infections: host factors and strain characteristics. J. Infect. Dis. 153:552-559.

Blaser M J., 1997. Epidemiologic and clinical features of *Campylobacter jejuni* infections. J. Infect. Dis. suppl. 2: S103-105.

Boyd Y., Herbert E. G., Marston K. L., Jones M. A. and Barrow P. A., 2005. Host genes affect intestinal colonisation of newly hatched chickens by *Campylobacter jejuni*. Immunogenetics, 57, 248-53.

Burr D H, Caldwell M B, Bourgeois A L, Morgan H R, Wistar R Jr, Walker R I. 1988. Mucosal and systemic immunity to *Campylobacter jejuni* in rabbits after gastric inoculation. Infect Immun. 1988: 56(1):99-105.

Buzby J C, Allos B M, Roberts T. 1997. The economic burden of *Campylobacter*-associated Guillain-Barré syndrome. J Infect Dis. 176 Suppl 2:S192-7.

Carrillo C, Atterbury R J, el-Shibiny A, Connerton P L, Dillon E, Scott A, Connerton I F. 2005. Bacteriophage therapy to reduce *Campylobacter jejuni* colonization of broiler chickens. Appl Environ Microbiol. 71(11):6554-63.

Carrillo, C. L., Atterbury, R. J., ElShibiny, A., Connerton, P. L. Scott, A., and Connerton, I. F. (2005). Bacteriophage therapy to reduce *Campylobacter jejuni* colonization of broiler chickens. Appl. Environ. Microbiol. 71, 6554-6563.

Casadevall A., Dadachova E., and Pirofski L. A. 2004. Passive antibody therapy for infectious diseases. Nat Rev Microbiol-Review. 2004 September; 2(9):695-703.

Castillo S. L., Heredia N., Contreras J. F., and Garcia S. 2011. Extracts of edible and medicinal plants in inhibition of growth, adherence, and cytotoxin production of *Campylobacter jejuni* and *Campylobacter coli*. J Food Sci. 76(6): M421-6.

Cawthraw S. A., Lind L., Kaijser B., and Newell D. G. 2000. Antibodies, directed towards *Campylobacter jejuni* antigens, in sera from poultry abattoir workers. Clin Exp Immunol. 122(1):55-60.

Chothia C, Lesk A M. Canonical structures for the hypervariable regions of immunoglobulins. J Mol Biol. 1987; 196(4):901-17.

Clark J. D., Oakes R. D., Redhead K., Crouch C. F., Francis M. J., Tomley F. M., and Blake D. P. 2012. *Eimeria* species parasites as novel vaccine delivery vectors: anti-*Campylobacter jejuni* protective immunity induced by *Eimeria tenella*-delivered CjaA. Vaccine. 30(16):2683-8.

Davies J., and L. Riechmann, Affinity improvement of single antibody VH domains: residues in all three hypervariable regions affect antigen binding. Immunotechnology 2 (1996) 169-179.

De Kruif, J. and Logtenberg, T. Leucine zipper dimerized bivalent and bispecific scFv antibodies from a semi-synthetic antibody phage display library. J. Biol. Chem. 271, 7630-7634 (1996).

de los Santos F., Donoghue A. M., Venkitanarayanan K., Metcalf J. H., Reyes-Herrera I., Dirain M. L., Aguiar V. F., Blore P. J., and Donoghue D. J. 2009. The natural feed additive caprylic acid decreases *Campylobacter jejuni* colonization in market-aged broiler chickens. Poult Sci. 88(1): 61-4.

de Zoete M. R., van Putten J. P. and Wagenaar J. A., 2007. Vaccination of chickens against *Campylobacter*. Vaccine, 25, 5548-57.

Dolby J M, Newell D G. 1986. The protection of infant mice from colonization with *Campylobacter jejuni* by vaccination of the dams. J Hyg (Lond). 1986: 96(2):143-51.

Eisenberg, D.; E. Schwarz; M. Komaromy & R. Wall (1984) Analysis of membrane and surface protein sequences with the hydrophobic moment plot. J Mol Biol, 179, 125-142

El-Shibiny A, Scott A, Timms A, Metawea Y, Connerton P, Connerton I. 2009. Application of a group II *Campylobacter* bacteriophage to reduce strains of *Campylobacter jejuni* and *Campylobacter coli* colonizing broiler chickens. J Food Prot. 72(4):733-40.

European Food Safety Authority (EFSA). Scientific Opinion on *Campylobacter* in broiler meat production: controloptions and performance objectives and/or targets at different stages of the food chain. 2011. EFSA Journal. 9(4) 2105:1-141

Gellynck X, Messens W, Halet D, Grijspeerdt K, Hartnett E, Viaene J. 2008. Economics of reducing *Campylobacter* at different levels within the Belgian poultry meat chain. J Food Prot. 71(3):479-85.

Goon S., Kelly J. F., Logan S. M., Ewing C. P., and Guerry P. 2003. Pseudaminic acid, the major modification on *Campylobacter* flagellin, is synthesized via the Cj1293 gene. Mol Microbiol. 50(2):659-71.

Greenberg A. S., Avila D., Hughes M., Hughes A., McKinney E. C., and Flajnik M. F. 1995. A new antigen receptor gene family that undergoes rearrangement and extensive somatic diversification in sharks. Nature. 374(6518):168-73.

Hamers-Casterman, C. Atarhouch T, Muyldermans S, Robinson G, Hamers C, Songa E B, Bendahman N, Hamers R. (1993) Naturally occurring antibodies devoid of light chains, Nature 363, 446-448.

Hariharan H, Murphy G, Kempt I. 2004. *Campylobacter jejuni*: Public health hazards and potential control methods in poultry: a review. Vet. Med.—Czech, 49: 441-446.

Hermans D, Pasmans F, Messens W, Martel A, Van Immerseel F, Rasschaert G, Heyndrickx M, Van Deun K, Haesebrouck F. 2011. Poultry as a host for the zoonotic pathogen *Campylobacter jejuni*. Review Vector Borne Zoonotic Dis. 2012 February; 12(2):89-98.

Hermans D., Martel A., Van Deun K., Verlinden M., Van Immerseel F., Garmyn A., Messens W., Heyndrickx M., Haesebrouck F., and Pasmans F. 2010. Intestinal mucus protects *Campylobacter jejuni* in the ceca of colonized broiler chickens against the bactericidal effects of medium-chain fatty acids. Poult Sci. 89(6):1144-55.

Jespers, L., Schon, O., Famm, K. and Winter, G. Aggregation-resistant domain antibodies selected on phage by heat denaturation. Nat. Biotechnol. 22, 1161-1165 (2004).

Kabat E A, Wu T T. Identical V region amino acid sequences and segments of sequences in antibodies of different specificities. Relative contributions of VH and VL genes, minigenes, and complementarity-determining regions to binding of antibody-combining sites. J Immunol. 1991a; 147:1709-19.

Kabat E A, Wu, T. T, Perry, H. M, Gottesman, K. S. and Koeler, C. Sequences of proteins of immunological interest. Publication 1991b: 91-3242.

Kaiser P., Howell M. M. J., Fife M., Sadeyen J. R., Salmon N., Rothwell L., Young J., Poh T. Y., Stevens M., Smith J., Burt D., Swaggerty C. and Kogut M., 2009. Towards the selection of chickens resistant to *Salmonella* and *Campylobacter* infections. Bull Mem Acad R Med Belg, 164, 17-25; discussion 25-6.

Kalmokoff et al., J. Bacteriol 2006; 188(12):4312-4320.

Layton S. L., Morgan M. J., Cole K., Kwon Y. M., Donoghue D. J., Hargis B. M., and Pumford N. R. 2011. Evaluation of *Salmonella*-vectored *Campylobacter* peptide epitopes for reduction of *Campylobacter jejuni* in broiler chickens. Clin Vaccine Immunol. 2011 March; 18(3):449-54.

Lefranc, M.-P., Pommié, C., Ruiz, M., Giudicelli, V., Foulquier, E., Truong, L., Thouvenin-Contet, V. and Lefranc, G. "IMGT unique numbering for immunoglobulin and T cell receptor variable domains and Ig superfamily V-like domains". Dev. Comp. Immunol., 27, 55-77 (2003)

Lin J. 2009. Novel approaches for *Campylobacter* control in poultry-review. Foodborne Pathog Dis. 6(7):755-65.

Luangtongkum T., Jeon B., Han J., Plummer P., Logue C. M. and Zhang Q. 2009. Antibiotic resistance in *Campylobacter*: emergence, transmission and persistence-Review. Future Microbiol. 4(2):189-200.

Man S M. 2011 The clinical importance of emerging *Campylobacter* species. Nat Rev Gastroenterol Hepatol. 25; 8(12):669-85.

Merritt, E. A. and Hol, W. G. AB5 toxins. Current Opinion in Structural Biology 5, 165-171 (1995).

Messaoudi S., Kergourlay G., Rossero A., Ferchichi M., Prévost H., Drider D., Manai M., and Dousset X. 2011. Identification of lactobacilli residing in chicken ceca with antagonism against *Campylobacter*. Int Microbiol. 14(2): 103-10.

Muyldermans, S. (2001) Single domain camel antibodies: current status, J Biotechnol 74, 277-302.

Newell D. G., and Wagenaar J. A. 2000. Poultry infections and their control at the farm level. In: *Campylobacter,* 2nd edition. Navhamkin I. and Blaser M. J. (eds.). Washington, D.C.: American Society for Microbiology, 200, pp. 497-509.

Newell D G, Fearnley C. 2003. Sources of *Campylobacter* colonization in broiler chickens. Appl Environ Microbiol. 69(8):4343-51.

Nielsen, U. B., Adams, G. P., Weiner, L. M. and Marks, J. D. Targeting of bivalent anti-ErbB2 diabody antibody fragments to tumor cells is independent of the intrinsic antibody affinity. Cancer Research 60, 6434-6440 (2000).

Nurmi E., and Rantala M. 1973. New aspects of *Salmonella* infection in broiler production. Nature. 241(5386): 210-1

Nuttall, S. D., Krishnan, U. V., Doughty, L., Pearson, K., Ryan, M. T., Hoogenraad, N. J., Hattarki, M., Carmichael, J. A., Irving, R. A. and Hudson, P. J. Isolation and characterization of an IgNAR variable domain specific for the human mitochondrial translocase receptor Tom70. Eur. J. Biochem. 270, 3543-3554 (2003).

Nyachuba D G. 2010 Foodborne illness: is it on the rise? Nutr Rev. 68(5):257-69.

Pace C N, Vajdos F, Fee L, Grimsley G, and Gray T. 1995. How to measure and predict the molar absorption coefficient of a protein. Protein Sci. (11):2411-2423.

Padlan, E. A. Anatomy of the antibody molecule. Molecular immunology 31, 169-217 (1994).

Pavlovskis O R, Rollins D M, Haberberger R L Jr, Green A E, Habash L, Strocko S, Walker R I. 1991. Significance of flagella in colonization resistance of rabbits immunized with *Campylobacter* spp. Infect Immun. 59(7):2259-64.

Power et al., J. Bacteriol (2003) 176:3303-3313.

Ridgway J B B, Presta L G, Carter P. "Knobs-into-holes" engineering of antibody CH3 domains for heavy chain heterodimerization. Prot Eng 1996; 9:617-621

Rollwagen F M, Pacheco N D, Clements J D, Pavlovskis O, Rollins D M, Walker R I. Killed *Campylobacter* elicits immune response and protection when administered with an oral adjuvant. Vaccine 1993. 11(13):1316-20.

Sahin O, Luo N, Huang S, Zhang Q. 2003. Effect of *Campylobacter*-specific maternal antibodies on *Campylobacter jejuni* colonization in young chickens. Appl Environ Microbiol. 69(9): 5372-9.

Santini C., Baffoni L., Gaggia F., Granata M., Gasbarri R., Di Gioia D., and Biavati B. 2010. Characterization of probiotic strains: an application as feed additives in poultry against *Campylobacter jejuni*. Int J Food Microbiol. 141 Suppl 1:S98-108.

Silva J, Leite D, Fernandes M, Mena C, Gibbs P A, Teixeira P. 2011. *Campylobacter* spp. as a Foodborne Pathogen: A Review. Front Microbiol. 2:200:1-12.

Smith J. L., and Fratamico P. M. 2010. Fluoroquinolone resistance in *campylobacter*-review. J Food Prot. 2010 June; 73(6):1141-52.

Stern N. J., Meinersmann R. J., and Dickerson H. W. 1990. Influence of antibody treatment of *Campylobacter jejuni* on the dose required to colonize chicks. Avian Dis. 34(3):595-601.

Stern N. J., and Robach M. C. 2003. Enumeration of *Campylobacter* spp. in broiler feces and in corresponding processed carcasses. J Food Prot. 66(9):1557-63.

Svetoch E. A. and Stern N. J. (2010) Bacteriocins to control *Campylobacter* spp. in poultry—A review. Poult Sci. 89(8):1763-8. Review.

Thibault P., Logan S. M., Kelly J. F., Brisson J. R., Ewing C. P., Trust T. J., and Guerry P. 2001. Identification of the carbohydrate moieties and glycosylation motifs in *Campylobacter jejuni* flagellin. J Biol Chem. 276(37):34862-70.

To, R., Hirama, T., Arbabi-Ghahroudi, M., MacKenzie, R., Wang, P., Xu, P., Ni, F. and Tanha, J. Isolation of monomeric human VHs by a phage selection. J. Biol. Chem. 280, 41395-41403 (2005).

Ueki Y, Umeda A, Fujimoto S, Mitsuyama M, Amako K. (1987) Protection against *Campylobacter jejuni* infection in suckling mice by anti-flagellar antibody. Microbiol Immunol 31: 1161-1171.

Wagenaar J. A., Jacob-Reitsma W., Hoshagen, M., and Newell D. G. 2008. Poultry colonization with *campylobacter* and its control at the primary production level. In: *Campylobacter*, 3rd edition. Navhamkin I., Szymanski C. M. and Blaser M. J. (eds.). Washington, D.C.: American Society for Microbiology, 2008, pp. 667-678.

Wagenaar J. A., Mevius D. J., and Havelaar A. H. 2006. *Campylobacter* in primary animal production and control strategies to reduce the burden of human campylobacteriosis. Rev Sci Tech. 25(2):581-94. Review Wagenaar J. A., Van Bergen M. A., Mueller M. A., Wassenaar T. M. and Carlton R. M. 2005. Phage therapy-reduces *Campylobacter jejuni* colonization in broilers. Vet Microbiol, 109, 275-83.

Wassenaar, T. M., Bleumink-Pluym, N. M. C. & Van der Zeijst, B. A. M. (1991). Inactivation of *Campylobacter jejuni* flagellin genes by homologous recombination demonstrates that PaA but not PaB is required for invasion. EMBO J 10, 2055-2061.

Willis W. L., and Reid L. 2008. Investigating the effects of dietary probiotic feeding regimens on broiler chicken production and *Campylobacter jejuni* presence. Poult Sci. 87(4):606-11.

Zeng X., Xu F., and Lin J. 2010. Development and Evaluation of CmeC Subunit Vaccine against *Campylobacter jejuni*. J Vaccines Vaccin. 1(3): 1-21.

Zhang G., Ma L., and Doyle M. P. 2007. Potential competitive exclusion bacteria from poultry inhibitory to *Campylobacter jejuni* and *Salmonella*. J Food Prot. 70(4): 867-73.

Zhang J, Li Q, Nguyen T D, Tremblay T L, Stone E, To R, Kelly J, Roger MacKenzie C. 2004. A pentavalent single-domain antibody approach to tumor antigen discovery and the development of novel proteomics reagents. J Mol Biol. 341(1):161-9.

Zhu et al., Immunology and Cell Biology (2010) 88:667-675.

U.S. Pat. No. 8,173,130
US 2009/0208506
US 2010/0239583
WO2003/046560
U.S. Pat. No. 6,180,370
U.S. Pat. No. 5,693,761
U.S. Pat. No. 6,054,297
U.S. Pat. No. 5,859,205
EP 626390
U.S. Pat. No. 5,869,619
U.S. Pat. No. 5,766,886
U.S. Pat. No. 5,821,123
EP 519596

What is claimed is:

1. An isolated or purified single-domain antibody (sdAb) to *Campylobacter jejuni* (*C. jejuni*), comprising CDR1 of sequence GLTFRNFHMA (SEQ ID NO:1), CDR2 of sequence ISWSRDRQ (SEQ ID NO:2), and CDR3 of sequence AARTASASGDWYKGSYQY (SEQ ID NO:3).

2. The isolated or purified single-domain antibody of claim 1, comprising the sequence:

(SEQ ID NO: 7)
QVX$_1$LX$_2$ESGGGLVQAGGSRRLSCATSGLTFRNFHMAWFRQVAGKEREV

VX$_3$AISWSRDRQYYPDPVKGRFTX$_4$TRDNAKNTVYLQMNSLKPEDTAVY

YCAARTASASGDWYKGSYQYWGQGTQVTVSS, where $X_1$=K or Q; $X_2$=E or V; $X_3$=A or C; $X_4$=I or C; or a sequence substantially identical thereto.

3. The isolated or purified single-domain antibody of claim 1, comprising the sequence:

(SEQ ID NO: 8)
QVKLEESGGGLVQAGGSRRLSCATSGLTFRNFHMAWFRQVAGKEREVVAA

ISWSRDRQYYPDPVKGRFTITRDNAKNTVYLQMNSLKPEDTAVYYCAART

ASASGDWYKGSYQYWGQGTQVTVSS;

(SEQ ID NO: 9)
QVQLVESGGGLVQAGGSRRLSCATSGLTFRNFHMAWFRQVAGKEREVVAA

ISWSRDRQYYPDPVKGRFTITRDNAKNTVYLQMNSLKPEDTAVYYCAART

ASASGDWYKGSYQYWGQGTQVTVSS;

(SEQ ID NO: 10)
QVKLEESGGGLVQAGGSRRLSCATSGLTFRNFHMAWFRQVAGKEREVVCA

ISWSRDRQYYPDPVKGRFTCTRDNAKNTVYLQMNSLKPEDTAVYYCAART

ASASGDWYKGSYQYWGQGTQVTVSS;

(SEQ ID NO: 11)
QVQLVESGGGLVQAGGSRRLSCATSGLTFRNFHMAWFRQVAGKEREVVCA

ISWSRDRQYYPDPVKGRFTCTRDNAKNTVYLQMNSLKPEDTAVYYCAART

ASASGDWYKGSYQYWGQGTQVTVSS;

or a sequence substantially identical thereto.

4. The isolated or purified single-domain antibody of claim 1, wherein the isolated or purified single-domain antibody specifically binds to the Fla A component of flagellin.

5. The isolated or purified single-domain antibody of claim 1, wherein the single-domain antibody is in a multivalent display.

6. The isolated or purified single-domain antibody of claim 1, wherein the single-domain antibody is linked to a detectable label.

7. A method of reducing the presence of *C. jejuni* in an animal or an animal environment comprising administering to the animal the isolated or purified single-domain antibody of claim 1.

8. The method of claim 7, further comprising administering to the animal an antibiotic, bacteriocin, or other plant- or animal-derived compound effective against *C. jejuni*.

9. The method of claim 7, further comprising administering a competing microbe to the animal together with the isolated or purified single-domain antibody of claim 1, optionally co-expressed or co-contained in a probiotic system.

10. A method of reducing introduction of *C. jejuni* into an animal environment comprising administering to an inductee animal the isolated or purified single-domain antibody of claim 1, prior to introducing the inductee animal into the animal environment.

11. A method of treating a *C. jejuni* infected subject, comprising administering to the subject the isolated or purified single-domain antibody of claim 1.

12. The method of claim 11, further comprising administering to the subject an antibiotic effective against *C. jejuni*.

13. The method of claim 11, wherein the subject is a livestock animal selected from the group consisting of chicken, cow, and sheep.

14. A formulation for use in treating *C. jejuni* infection, comprising the isolated or purified single-domain antibody of claim 1, and an excipient.

15. A method of detecting *C. jejuni* in a sample, comprising contacting the sample with the isolated or purified single-domain antibody of claim 1, and detecting the presence of a bound isolated or purified single-domain antibody.

* * * * *

SEQUENCE LISTING

```
<160> NUMBER OF SEQ ID NOS: 42

<210> SEQ ID NO 1
<211> LENGTH: 10
<212> TYPE: PRT
<213> ORGANISM: Lama glama
<220> FEATURE:
<221> NAME/KEY: MISC_FEATURE
<222> LOCATION: (1)..(10)
<223> OTHER INFORMATION: FlagV1 CDR1

<400> SEQUENCE: 1

Gly Leu Thr Phe Arg Asn Phe His Met Ala
1               5                   10

<210> SEQ ID NO 2
<211> LENGTH: 8
<212> TYPE: PRT
<213> ORGANISM: Lama glama
```

```
<220> FEATURE:
<221> NAME/KEY: MISC_FEATURE
<222> LOCATION: (1)..(8)
<223> OTHER INFORMATION: FlagV1 CDR2

<400> SEQUENCE: 2

Ile Ser Trp Ser Arg Asp Arg Gln
1               5

<210> SEQ ID NO 3
<211> LENGTH: 18
<212> TYPE: PRT
<213> ORGANISM: Lama glama
<220> FEATURE:
<221> NAME/KEY: MISC_FEATURE
<222> LOCATION: (1)..(18)
<223> OTHER INFORMATION: FlagV1 CDR3

<400> SEQUENCE: 3

Ala Ala Arg Thr Ala Ser Ala Ser Gly Asp Trp Tyr Lys Gly Ser Tyr
1               5                   10                  15
Gln Tyr

<210> SEQ ID NO 4
<211> LENGTH: 10
<212> TYPE: PRT
<213> ORGANISM: Lama glama
<220> FEATURE:
<221> NAME/KEY: MISC_FEATURE
<222> LOCATION: (1)..(10)
<223> OTHER INFORMATION: FlagV6 CDR1

<400> SEQUENCE: 4

Val Ser Thr Phe Ser Ile Asn Ala Leu Gly
1               5                   10

<210> SEQ ID NO 5
<211> LENGTH: 7
<212> TYPE: PRT
<213> ORGANISM: Lama glama
<220> FEATURE:
<221> NAME/KEY: MISC_FEATURE
<222> LOCATION: (1)..(7)
<223> OTHER INFORMATION: FlagV6 CDR2

<400> SEQUENCE: 5

Ile Gly Ser Asp Gly Thr Val
1               5

<210> SEQ ID NO 6
<211> LENGTH: 22
<212> TYPE: PRT
<213> ORGANISM: Lama glama
<220> FEATURE:
<221> NAME/KEY: MISC_FEATURE
<222> LOCATION: (1)..(22)
<223> OTHER INFORMATION: FlagV6 CDR3

<400> SEQUENCE: 6

Asn Ala Ala Gly Lys Arg Ile Gly Ser Asp Gly Ser Ile Trp Phe Ala
1               5                   10                  15
Val Ala Ser Phe Gly Ser
            20

<210> SEQ ID NO 7
<211> LENGTH: 125
<212> TYPE: PRT
```

```
<213> ORGANISM: Lama glama
<220> FEATURE:
<221> NAME/KEY: MISC_FEATURE
<222> LOCATION: (1)..(125)
<223> OTHER INFORMATION: FlagV1 consensus sequence
<220> FEATURE:
<221> NAME/KEY: MISC_FEATURE
<222> LOCATION: (3)..(3)
<223> OTHER INFORMATION: Xaa is K (Lys) or Q (Gln)
<220> FEATURE:
<221> NAME/KEY: MISC_FEATURE
<222> LOCATION: (5)..(5)
<223> OTHER INFORMATION: Xaa is E (Glu) or V (Val)
<220> FEATURE:
<221> NAME/KEY: MISC_FEATURE
<222> LOCATION: (49)..(49)
<223> OTHER INFORMATION: Xaa is A (Ala) or C (Cys)
<220> FEATURE:
<221> NAME/KEY: MISC_FEATURE
<222> LOCATION: (70)..(70)
<223> OTHER INFORMATION: Xaa is I (Ile) or C (Cys)

<400> SEQUENCE: 7

Gln Val Xaa Leu Xaa Glu Ser Gly Gly Gly Leu Val Gln Ala Gly Gly
1               5                   10                  15

Ser Arg Arg Leu Ser Cys Ala Thr Ser Gly Leu Thr Phe Arg Asn Phe
            20                  25                  30

His Met Ala Trp Phe Arg Gln Val Ala Gly Lys Glu Arg Glu Val Val
        35                  40                  45

Xaa Ala Ile Ser Trp Ser Arg Asp Arg Gln Tyr Tyr Pro Asp Pro Val
    50                  55                  60

Lys Gly Arg Phe Thr Xaa Thr Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Thr Ala Ser Ala Ser Gly Asp Trp Tyr Lys Gly Ser Tyr
            100                 105                 110

Gln Tyr Trp Gly Gln Gly Thr Gln Val Thr Val Ser Ser
        115                 120                 125

<210> SEQ ID NO 8
<211> LENGTH: 125
<212> TYPE: PRT
<213> ORGANISM: Lama glama
<220> FEATURE:
<221> NAME/KEY: MISC_FEATURE
<222> LOCATION: (1)..(125)
<223> OTHER INFORMATION: FlagV1M

<400> SEQUENCE: 8

Gln Val Lys Leu Glu Glu Ser Gly Gly Gly Leu Val Gln Ala Gly Gly
1               5                   10                  15

Ser Arg Arg Leu Ser Cys Ala Thr Ser Gly Leu Thr Phe Arg Asn Phe
            20                  25                  30

His Met Ala Trp Phe Arg Gln Val Ala Gly Lys Glu Arg Glu Val Val
        35                  40                  45

Ala Ala Ile Ser Trp Ser Arg Asp Arg Gln Tyr Tyr Pro Asp Pro Val
    50                  55                  60

Lys Gly Arg Phe Thr Ile Thr Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Thr Ala Ser Ala Ser Gly Asp Trp Tyr Lys Gly Ser Tyr
```

-continued

```
                100             105             110
Gln Tyr Trp Gly Gln Gly Thr Gln Val Thr Val Ser Ser
        115             120             125

<210> SEQ ID NO 9
<211> LENGTH: 125
<212> TYPE: PRT
<213> ORGANISM: Lama glama
<220> FEATURE:
<221> NAME/KEY: MISC_FEATURE
<222> LOCATION: (1)..(125)
<223> OTHER INFORMATION: FlagV1F23M

<400> SEQUENCE: 9

Gln Val Gln Leu Val Glu Ser Gly Gly Gly Leu Val Gln Ala Gly Gly
1               5                   10                  15

Ser Arg Arg Leu Ser Cys Ala Thr Ser Gly Leu Thr Phe Arg Asn Phe
            20                  25                  30

His Met Ala Trp Phe Arg Gln Val Ala Gly Lys Glu Arg Glu Val Val
        35                  40                  45

Ala Ala Ile Ser Trp Ser Arg Asp Arg Gln Tyr Tyr Pro Asp Pro Val
    50                  55                  60

Lys Gly Arg Phe Thr Ile Thr Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Thr Ala Ser Ala Ser Gly Asp Trp Tyr Lys Gly Ser Tyr
            100                 105                 110

Gln Tyr Trp Gly Gln Gly Thr Gln Val Thr Val Ser Ser
        115             120             125

<210> SEQ ID NO 10
<211> LENGTH: 125
<212> TYPE: PRT
<213> ORGANISM: Lama glama
<220> FEATURE:
<221> NAME/KEY: MISC_FEATURE
<222> LOCATION: (1)..(125)
<223> OTHER INFORMATION: FlagV1MDSB

<400> SEQUENCE: 10

Gln Val Lys Leu Glu Glu Ser Gly Gly Gly Leu Val Gln Ala Gly Gly
1               5                   10                  15

Ser Arg Arg Leu Ser Cys Ala Thr Ser Gly Leu Thr Phe Arg Asn Phe
            20                  25                  30

His Met Ala Trp Phe Arg Gln Val Ala Gly Lys Glu Arg Glu Val Val
        35                  40                  45

Cys Ala Ile Ser Trp Ser Arg Asp Arg Gln Tyr Tyr Pro Asp Pro Val
    50                  55                  60

Lys Gly Arg Phe Thr Cys Thr Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Thr Ala Ser Ala Ser Gly Asp Trp Tyr Lys Gly Ser Tyr
            100                 105                 110

Gln Tyr Trp Gly Gln Gly Thr Gln Val Thr Val Ser Ser
        115             120             125

<210> SEQ ID NO 11
```

```
<211> LENGTH: 125
<212> TYPE: PRT
<213> ORGANISM: Lama glama
<220> FEATURE:
<221> NAME/KEY: MISC_FEATURE
<222> LOCATION: (1)..(125)
<223> OTHER INFORMATION: FlagV1F23MDSB

<400> SEQUENCE: 11
```

Gln Val Gln Leu Val Glu Ser Gly Gly Gly Leu Val Gln Ala Gly Gly
1               5                   10                  15

Ser Arg Arg Leu Ser Cys Ala Thr Ser Gly Leu Thr Phe Arg Asn Phe
            20                  25                  30

His Met Ala Trp Phe Arg Gln Val Ala Gly Lys Glu Arg Glu Val Val
        35                  40                  45

Cys Ala Ile Ser Trp Ser Arg Asp Arg Gln Tyr Tyr Pro Asp Pro Val
50                  55                  60

Lys Gly Arg Phe Thr Cys Thr Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Thr Ala Ser Ala Ser Gly Asp Trp Tyr Lys Gly Ser Tyr
            100                 105                 110

Gln Tyr Trp Gly Gln Gly Thr Gln Val Thr Val Ser Ser
        115                 120                 125

```
<210> SEQ ID NO 12
<211> LENGTH: 128
<212> TYPE: PRT
<213> ORGANISM: Lama glama
<220> FEATURE:
<221> NAME/KEY: MISC_FEATURE
<222> LOCATION: (1)..(128)
<223> OTHER INFORMATION: FlagV6 consensus sequence
<220> FEATURE:
<221> NAME/KEY: MISC_FEATURE
<222> LOCATION: (3)..(3)
<223> OTHER INFORMATION: Xaa is K (Lys) or Q (Gln)
<220> FEATURE:
<221> NAME/KEY: MISC_FEATURE
<222> LOCATION: (5)..(5)
<223> OTHER INFORMATION: Xaa is E (Glu) or V (Val)
<220> FEATURE:
<221> NAME/KEY: MISC_FEATURE
<222> LOCATION: (49)..(49)
<223> OTHER INFORMATION: Xaa is A (Ala) or C (Cys)
<220> FEATURE:
<221> NAME/KEY: MISC_FEATURE
<222> LOCATION: (69)..(69)
<223> OTHER INFORMATION: Xaa is I (Ile) or C (Cys)

<400> SEQUENCE: 12
```

Gln Val Xaa Leu Xaa Glu Ser Gly Gly Gly Leu Val Gln Ala Gly Gly
1               5                   10                  15

Ser Leu Arg Val Ser Cys Thr Ala Ser Val Ser Thr Phe Ser Ile Asn
            20                  25                  30

Ala Leu Gly Trp Tyr Arg Gln Ala Pro Gly Lys Ala Arg Glu Leu Val
        35                  40                  45

Xaa Ala Ile Gly Ser Asp Gly Thr Val Tyr Tyr Thr Asp Ser Val Lys
50                  55                  60

Gly Arg Phe Thr Xaa Ser Arg Asp Asn Ala Lys Asn Thr Val Ser Leu
65                  70                  75                  80

Gln Met Ser Ser Leu Lys Pro Glu Asp Thr Ala Val Tyr Tyr Cys Asn
                85                  90                  95

```
Ala Ala Gly Lys Arg Ile Gly Ser Asp Gly Ser Ile Trp Phe Ala Val
            100                 105                 110

Ala Ser Phe Gly Ser Trp Gly Gln Gly Thr Gln Val Thr Val Ser Ser
            115                 120                 125

<210> SEQ ID NO 13
<211> LENGTH: 128
<212> TYPE: PRT
<213> ORGANISM: Lama glama
<220> FEATURE:
<221> NAME/KEY: MISC_FEATURE
<222> LOCATION: (1)..(128)
<223> OTHER INFORMATION: FlagV6M

<400> SEQUENCE: 13

Gln Val Lys Leu Glu Glu Ser Gly Gly Leu Val Gln Ala Gly Gly
1               5                   10                  15

Ser Leu Arg Val Ser Cys Thr Ala Ser Val Ser Thr Phe Ser Ile Asn
            20                  25                  30

Ala Leu Gly Trp Tyr Arg Gln Ala Pro Gly Lys Ala Arg Glu Leu Val
            35                  40                  45

Ala Ala Ile Gly Ser Asp Gly Thr Val Tyr Tyr Thr Asp Ser Val Lys
50                  55                  60

Gly Arg Phe Thr Ile Ser Arg Asp Asn Ala Lys Asn Thr Val Ser Leu
65                  70                  75                  80

Gln Met Ser Ser Leu Lys Pro Glu Asp Thr Ala Val Tyr Tyr Cys Asn
                85                  90                  95

Ala Ala Gly Lys Arg Ile Gly Ser Asp Gly Ser Ile Trp Phe Ala Val
            100                 105                 110

Ala Ser Phe Gly Ser Trp Gly Gln Gly Thr Gln Val Thr Val Ser Ser
            115                 120                 125

<210> SEQ ID NO 14
<211> LENGTH: 128
<212> TYPE: PRT
<213> ORGANISM: Lama glama
<220> FEATURE:
<221> NAME/KEY: MISC_FEATURE
<222> LOCATION: (1)..(128)
<223> OTHER INFORMATION: FlagV6F23M

<400> SEQUENCE: 14

Gln Val Gln Leu Val Glu Ser Gly Gly Gly Leu Val Gln Ala Gly Gly
1               5                   10                  15

Ser Leu Arg Val Ser Cys Thr Ala Ser Val Ser Thr Phe Ser Ile Asn
            20                  25                  30

Ala Leu Gly Trp Tyr Arg Gln Ala Pro Gly Lys Ala Arg Glu Leu Val
            35                  40                  45

Ala Ala Ile Gly Ser Asp Gly Thr Val Tyr Tyr Thr Asp Ser Val Lys
50                  55                  60

Gly Arg Phe Thr Ile Ser Arg Asp Asn Ala Lys Asn Thr Val Ser Leu
65                  70                  75                  80

Gln Met Ser Ser Leu Lys Pro Glu Asp Thr Ala Val Tyr Tyr Cys Asn
                85                  90                  95

Ala Ala Gly Lys Arg Ile Gly Ser Asp Gly Ser Ile Trp Phe Ala Val
            100                 105                 110

Ala Ser Phe Gly Ser Trp Gly Gln Gly Thr Gln Val Thr Val Ser Ser
            115                 120                 125
```

<210> SEQ ID NO 15
<211> LENGTH: 128
<212> TYPE: PRT
<213> ORGANISM: Lama glama
<220> FEATURE:
<221> NAME/KEY: MISC_FEATURE
<222> LOCATION: (1)..(128)
<223> OTHER INFORMATION: FlagV6MDSB

<400> SEQUENCE: 15

Gln Val Lys Leu Glu Glu Ser Gly Gly Gly Leu Val Gln Ala Gly Gly
1               5                   10                  15

Ser Leu Arg Val Ser Cys Thr Ala Ser Val Ser Thr Phe Ser Ile Asn
            20                  25                  30

Ala Leu Gly Trp Tyr Arg Gln Ala Pro Gly Lys Ala Arg Glu Leu Val
        35                  40                  45

Cys Ala Ile Gly Ser Asp Gly Thr Val Tyr Tyr Thr Asp Ser Val Lys
    50                  55                  60

Gly Arg Phe Thr Cys Ser Arg Asp Asn Ala Lys Asn Thr Val Ser Leu
65                  70                  75                  80

Gln Met Ser Ser Leu Lys Pro Glu Asp Thr Ala Val Tyr Tyr Cys Asn
                85                  90                  95

Ala Ala Gly Lys Arg Ile Gly Ser Asp Gly Ser Ile Trp Phe Ala Val
            100                 105                 110

Ala Ser Phe Gly Ser Trp Gly Gln Gly Thr Gln Val Thr Val Ser Ser
        115                 120                 125

<210> SEQ ID NO 16
<211> LENGTH: 128
<212> TYPE: PRT
<213> ORGANISM: Lama glama
<220> FEATURE:
<221> NAME/KEY: MISC_FEATURE
<222> LOCATION: (1)..(128)
<223> OTHER INFORMATION: FlagV6F23MDSB

<400> SEQUENCE: 16

Gln Val Gln Leu Val Glu Ser Gly Gly Gly Leu Val Gln Ala Gly Gly
1               5                   10                  15

Ser Leu Arg Val Ser Cys Thr Ala Ser Val Ser Thr Phe Ser Ile Asn
            20                  25                  30

Ala Leu Gly Trp Tyr Arg Gln Ala Pro Gly Lys Ala Arg Glu Leu Val
        35                  40                  45

Cys Ala Ile Gly Ser Asp Gly Thr Val Tyr Tyr Thr Asp Ser Val Lys
    50                  55                  60

Gly Arg Phe Thr Cys Ser Arg Asp Asn Ala Lys Asn Thr Val Ser Leu
65                  70                  75                  80

Gln Met Ser Ser Leu Lys Pro Glu Asp Thr Ala Val Tyr Tyr Cys Asn
                85                  90                  95

Ala Ala Gly Lys Arg Ile Gly Ser Asp Gly Ser Ile Trp Phe Ala Val
            100                 105                 110

Ala Ser Phe Gly Ser Trp Gly Gln Gly Thr Gln Val Thr Val Ser Ser
        115                 120                 125

<210> SEQ ID NO 17
<211> LENGTH: 69
<212> TYPE: PRT
<213> ORGANISM: Artificial Sequence
<220> FEATURE:
<223> OTHER INFORMATION: Pentamerization domain

```
<400> SEQUENCE: 17

Thr Pro Asp Cys Val Thr Gly Lys Val Glu Tyr Thr Lys Tyr Asn Asp
1               5                   10                  15

Glu Asp Thr Phe Thr Val Lys Val Gly Asp Lys Glu Leu Phe Thr Asn
            20                  25                  30

Arg Ala Asn Leu Gln Ser Leu Leu Ser Ala Gln Ile Thr Gly Met
        35                  40                  45

Thr Val Thr Ile Lys Thr Asn Ala Cys His Asn Gly Gly Phe Ser
    50                  55                  60

Glu Val Ile Phe Arg
65

<210> SEQ ID NO 18
<211> LENGTH: 11
<212> TYPE: PRT
<213> ORGANISM: Artificial Sequence
<220> FEATURE:
<223> OTHER INFORMATION: Linker

<400> SEQUENCE: 18

Gly Pro Gly Gly Gly Ser Gly Gly Gly Ser
1               5                   10

<210> SEQ ID NO 19
<211> LENGTH: 205
<212> TYPE: PRT
<213> ORGANISM: Lama glama
<220> FEATURE:
<221> NAME/KEY: MISC_FEATURE
<222> LOCATION: (1)..(205)
<223> OTHER INFORMATION: FlagV1P

<400> SEQUENCE: 19

Gln Val Lys Leu Glu Glu Ser Gly Gly Leu Val Gln Ala Gly Gly
1               5                   10                  15

Ser Arg Arg Leu Ser Cys Ala Thr Ser Gly Leu Thr Phe Arg Asn Phe
            20                  25                  30

His Met Ala Trp Phe Arg Gln Val Ala Gly Lys Glu Arg Glu Val Val
        35                  40                  45

Ala Ala Ile Ser Trp Ser Arg Asp Arg Gln Tyr Tyr Pro Asp Pro Val
    50                  55                  60

Lys Gly Arg Phe Thr Ile Thr Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Thr Ala Ser Ala Ser Gly Asp Trp Tyr Lys Gly Ser Tyr
            100                 105                 110

Gln Tyr Trp Gly Gln Gly Thr Gln Val Thr Val Ser Ser Pro Gly
        115                 120                 125

Gly Gly Ser Gly Gly Gly Ser Thr Pro Asp Cys Val Thr Gly Lys
    130                 135                 140

Val Glu Tyr Thr Lys Tyr Asn Asp Glu Asp Thr Phe Thr Val Lys Val
145                 150                 155                 160

Gly Asp Lys Glu Leu Phe Thr Asn Arg Ala Asn Leu Gln Ser Leu Leu
                165                 170                 175

Leu Ser Ala Gln Ile Thr Gly Met Thr Val Thr Ile Lys Thr Asn Ala
            180                 185                 190
```

Cys His Asn Gly Gly Gly Phe Ser Glu Val Ile Phe Arg
            195                 200                 205

<210> SEQ ID NO 20
<211> LENGTH: 205
<212> TYPE: PRT
<213> ORGANISM: Lama glama
<220> FEATURE:
<221> NAME/KEY: MISC_FEATURE
<222> LOCATION: (1)..(205)
<223> OTHER INFORMATION: FlagV1F23P

<400> SEQUENCE: 20

Gln Val Gln Leu Val Glu Ser Gly Gly Gly Leu Val Gln Ala Gly Gly
1               5                   10                  15

Ser Arg Arg Leu Ser Cys Ala Thr Ser Gly Leu Thr Phe Arg Asn Phe
            20                  25                  30

His Met Ala Trp Phe Arg Gln Val Ala Gly Lys Glu Arg Glu Val Val
        35                  40                  45

Ala Ala Ile Ser Trp Ser Arg Asp Arg Gln Tyr Tyr Pro Asp Pro Val
    50                  55                  60

Lys Gly Arg Phe Thr Ile Thr Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Thr Ala Ser Ala Ser Gly Asp Trp Tyr Lys Gly Ser Tyr
            100                 105                 110

Gln Tyr Trp Gly Gln Gly Thr Gln Val Thr Val Ser Ser Gly Pro Gly
        115                 120                 125

Gly Gly Ser Gly Gly Gly Ser Thr Pro Asp Cys Val Thr Gly Lys
    130                 135                 140

Val Glu Tyr Thr Lys Tyr Asn Asp Glu Asp Thr Phe Thr Val Lys Val
145                 150                 155                 160

Gly Asp Lys Glu Leu Phe Thr Asn Arg Ala Asn Leu Gln Ser Leu Leu
                165                 170                 175

Leu Ser Ala Gln Ile Thr Gly Met Thr Val Thr Ile Lys Thr Asn Ala
            180                 185                 190

Cys His Asn Gly Gly Gly Phe Ser Glu Val Ile Phe Arg
        195                 200                 205

<210> SEQ ID NO 21
<211> LENGTH: 208
<212> TYPE: PRT
<213> ORGANISM: Lama glama
<220> FEATURE:
<221> NAME/KEY: MISC_FEATURE
<222> LOCATION: (1)..(208)
<223> OTHER INFORMATION: FlagV6P

<400> SEQUENCE: 21

Gln Val Lys Leu Glu Glu Ser Gly Gly Gly Leu Val Gln Ala Gly Gly
1               5                   10                  15

Ser Leu Arg Val Ser Cys Thr Ala Ser Val Thr Phe Ser Ile Asn
            20                  25                  30

Ala Leu Gly Trp Tyr Arg Gln Ala Pro Gly Lys Ala Arg Glu Leu Val
        35                  40                  45

Ala Ala Ile Gly Ser Asp Gly Thr Val Tyr Tyr Thr Asp Ser Val Lys
    50                  55                  60

Gly Arg Phe Thr Ile Ser Arg Asp Asn Ala Lys Asn Thr Val Ser Leu

Gln Met Ser Ser Leu Lys Pro Glu Asp Thr Ala Val Tyr Tyr Cys Asn
                85                  90                  95

Ala Ala Gly Lys Arg Ile Gly Ser Asp Gly Ser Ile Trp Phe Ala Val
            100                 105                 110

Ala Ser Phe Gly Ser Trp Gly Gln Gly Thr Gln Val Thr Val Ser Ser
        115                 120                 125

Gly Pro Gly Gly Ser Gly Gly Gly Ser Thr Pro Asp Cys Val
    130                 135                 140

Thr Gly Lys Val Glu Tyr Thr Lys Tyr Asn Asp Glu Asp Thr Phe Thr
145                 150                 155                 160

Val Lys Val Gly Asp Lys Glu Leu Phe Thr Asn Arg Ala Asn Leu Gln
                165                 170                 175

Ser Leu Leu Leu Ser Ala Gln Ile Thr Gly Met Thr Val Thr Ile Lys
            180                 185                 190

Thr Asn Ala Cys His Asn Gly Gly Phe Ser Glu Val Ile Phe Arg
        195                 200                 205

<210> SEQ ID NO 22
<211> LENGTH: 208
<212> TYPE: PRT
<213> ORGANISM: Lama glama
<220> FEATURE:
<221> NAME/KEY: MISC_FEATURE
<222> LOCATION: (1)..(208)
<223> OTHER INFORMATION: FlagV6F23P

<400> SEQUENCE: 22

Gln Val Gln Leu Val Glu Ser Gly Gly Gly Leu Val Gln Ala Gly Gly
1               5                   10                  15

Ser Leu Arg Val Ser Cys Thr Ala Ser Val Ser Thr Phe Ser Ile Asn
                20                  25                  30

Ala Leu Gly Trp Tyr Arg Gln Ala Pro Gly Lys Ala Arg Glu Leu Val
            35                  40                  45

Ala Ala Ile Gly Ser Asp Gly Thr Val Tyr Tyr Thr Asp Ser Val Lys
        50                  55                  60

Gly Arg Phe Thr Ile Ser Arg Asp Asn Ala Lys Asn Thr Val Ser Leu
65                  70                  75                  80

Gln Met Ser Ser Leu Lys Pro Glu Asp Thr Ala Val Tyr Tyr Cys Asn
                85                  90                  95

Ala Ala Gly Lys Arg Ile Gly Ser Asp Gly Ser Ile Trp Phe Ala Val
            100                 105                 110

Ala Ser Phe Gly Ser Trp Gly Gln Gly Thr Gln Val Thr Val Ser Ser
        115                 120                 125

Gly Pro Gly Gly Ser Gly Gly Gly Ser Thr Pro Asp Cys Val
    130                 135                 140

Thr Gly Lys Val Glu Tyr Thr Lys Tyr Asn Asp Glu Asp Thr Phe Thr
145                 150                 155                 160

Val Lys Val Gly Asp Lys Glu Leu Phe Thr Asn Arg Ala Asn Leu Gln
                165                 170                 175

Ser Leu Leu Leu Ser Ala Gln Ile Thr Gly Met Thr Val Thr Ile Lys
            180                 185                 190

Thr Asn Ala Cys His Asn Gly Gly Phe Ser Glu Val Ile Phe Arg
        195                 200                 205

<210> SEQ ID NO 23

```
<211> LENGTH: 38
<212> TYPE: DNA
<213> ORGANISM: Artificial Sequence
<220> FEATURE:
<223> OTHER INFORMATION: BbsI1-VHH forward primer

<400> SEQUENCE: 23
tatgaagaca ccaggcccag gtaaagctgg aggagtct                                 38

<210> SEQ ID NO 24
<211> LENGTH: 30
<212> TYPE: DNA
<213> ORGANISM: Artificial Sequence
<220> FEATURE:
<223> OTHER INFORMATION: BamHI-VHH reverse primer

<400> SEQUENCE: 24
ttgttcggat cctgaggaga cggtgacctg                                          30

<210> SEQ ID NO 25
<211> LENGTH: 36
<212> TYPE: DNA
<213> ORGANISM: Artificial Sequence
<220> FEATURE:
<223> OTHER INFORMATION: ApaI-VHH reverse primer

<400> SEQUENCE: 25
attattatgg gccctgagga gacggtgacc tgggtc                                   36

<210> SEQ ID NO 26
<211> LENGTH: 41
<212> TYPE: DNA
<213> ORGANISM: Artificial Sequence
<220> FEATURE:
<223> OTHER INFORMATION: MJ7BACK primer

<400> SEQUENCE: 26
catgtgcatg gcctagactc gcggcccagc cggccatggc c                             41

<210> SEQ ID NO 27
<211> LENGTH: 31
<212> TYPE: DNA
<213> ORGANISM: Artificial Sequence
<220> FEATURE:
<223> OTHER INFORMATION: MJFOR 11 primer

<400> SEQUENCE: 27
catgtgtaga ttctgcctgg ccggcctggc c                                        31

<210> SEQ ID NO 28
<211> LENGTH: 52
<212> TYPE: DNA
<213> ORGANISM: Artificial Sequence
<220> FEATURE:
<223> OTHER INFORMATION: V1-DSB-for primer

<400> SEQUENCE: 28
tagacagtat tatccagatc ccgtgaaggg ccgattcacc tgcaccagag ac                 52

<210> SEQ ID NO 29
<211> LENGTH: 44
<212> TYPE: DNA
<213> ORGANISM: Artificial Sequence
<220> FEATURE:
<223> OTHER INFORMATION: V1-DSB-rev primer

<400> SEQUENCE: 29
```

-continued

```
ggataatact gtctatctct actccaggaa atagcgcaca ctac                44
```

```
<210> SEQ ID NO 30
<211> LENGTH: 125
<212> TYPE: PRT
<213> ORGANISM: Lama glama
<220> FEATURE:
<221> NAME/KEY: MISC_FEATURE
<222> LOCATION: (1)..(125)
<223> OTHER INFORMATION: FlagV1MDSB

<400> SEQUENCE: 30

Gln Val Lys Leu Glu Glu Ser Gly Gly Gly Leu Val Gln Ala Gly Gly
1               5                  10                  15

Ser Arg Arg Leu Ser Cys Ala Thr Ser Gly Leu Thr Phe Arg Asn Phe
            20                  25                  30

His Met Ala Trp Phe Arg Gln Val Ala Gly Lys Glu Arg Glu Val Val
        35                  40                  45

Cys Ala Ile Ser Trp Ser Arg Asp Arg Gln Tyr Tyr Pro Asp Pro Val
    50                  55                  60

Lys Gly Arg Phe Thr Cys Thr Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Thr Ala Ser Ala Ser Gly Asp Trp Tyr Lys Gly Ser Tyr
            100                 105                 110

Gln Tyr Trp Gly Gln Gly Thr Gln Val Thr Val Ser Ser
        115                 120                 125

<210> SEQ ID NO 31
<211> LENGTH: 125
<212> TYPE: PRT
<213> ORGANISM: Lama glama
<220> FEATURE:
<221> NAME/KEY: MISC_FEATURE
<222> LOCATION: (1)..(125)
<223> OTHER INFORMATION: FlagV1F23MDSB

<400> SEQUENCE: 31

Gln Val Gln Leu Val Glu Ser Gly Gly Gly Leu Val Gln Ala Gly Gly
1               5                  10                  15

Ser Arg Arg Leu Ser Cys Ala Thr Ser Gly Leu Thr Phe Arg Asn Phe
            20                  25                  30

His Met Ala Trp Phe Arg Gln Val Ala Gly Lys Glu Arg Glu Val Val
        35                  40                  45

Cys Ala Ile Ser Trp Ser Arg Asp Arg Gln Tyr Tyr Pro Asp Pro Val
    50                  55                  60

Lys Gly Arg Phe Thr Cys Thr Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Thr Ala Ser Ala Ser Gly Asp Trp Tyr Lys Gly Ser Tyr
            100                 105                 110

Gln Tyr Trp Gly Gln Gly Thr Gln Val Thr Val Ser Ser
        115                 120                 125

<210> SEQ ID NO 32
<211> LENGTH: 128
<212> TYPE: PRT
```

<213> ORGANISM: Lama glama
<220> FEATURE:
<221> NAME/KEY: MISC_FEATURE
<222> LOCATION: (1)..(128)
<223> OTHER INFORMATION: FlagV6MDSB

<400> SEQUENCE: 32

Gln Val Lys Leu Glu Glu Ser Gly Gly Gly Leu Val Gln Ala Gly Gly
1               5                   10                  15

Ser Leu Arg Val Ser Cys Thr Ala Ser Val Ser Thr Phe Ser Ile Asn
            20                  25                  30

Ala Leu Gly Trp Tyr Arg Gln Ala Pro Gly Lys Ala Arg Glu Leu Val
        35                  40                  45

Cys Ala Ile Gly Ser Asp Gly Thr Val Tyr Tyr Thr Asp Ser Val Lys
    50                  55                  60

Gly Arg Phe Thr Cys Ser Arg Asp Asn Ala Lys Asn Thr Val Ser Leu
65                  70                  75                  80

Gln Met Ser Ser Leu Lys Pro Glu Asp Thr Ala Val Tyr Tyr Cys Asn
                85                  90                  95

Ala Ala Gly Lys Arg Ile Gly Ser Asp Gly Ser Ile Trp Phe Ala Val
            100                 105                 110

Ala Ser Phe Gly Ser Trp Gly Gln Gly Thr Gln Val Thr Val Ser Ser
        115                 120                 125

<210> SEQ ID NO 33
<211> LENGTH: 128
<212> TYPE: PRT
<213> ORGANISM: Lama glama
<220> FEATURE:
<221> NAME/KEY: MISC_FEATURE
<222> LOCATION: (1)..(128)
<223> OTHER INFORMATION: FlagV6MF23DSB

<400> SEQUENCE: 33

Gln Val Gln Leu Val Glu Ser Gly Gly Gly Leu Val Gln Ala Gly Gly
1               5                   10                  15

Ser Leu Arg Val Ser Cys Thr Ala Ser Val Ser Thr Phe Ser Ile Asn
            20                  25                  30

Ala Leu Gly Trp Tyr Arg Gln Ala Pro Gly Lys Ala Arg Glu Leu Val
        35                  40                  45

Cys Ala Ile Gly Ser Asp Gly Thr Val Tyr Tyr Thr Asp Ser Val Lys
    50                  55                  60

Gly Arg Phe Thr Cys Ser Arg Asp Asn Ala Lys Asn Thr Val Ser Leu
65                  70                  75                  80

Gln Met Ser Ser Leu Lys Pro Glu Asp Thr Ala Val Tyr Tyr Cys Asn
                85                  90                  95

Ala Ala Gly Lys Arg Ile Gly Ser Asp Gly Ser Ile Trp Phe Ala Val
            100                 105                 110

Ala Ser Phe Gly Ser Trp Gly Gln Gly Thr Gln Val Thr Val Ser Ser
        115                 120                 125

<210> SEQ ID NO 34
<211> LENGTH: 205
<212> TYPE: PRT
<213> ORGANISM: Lama glama
<220> FEATURE:
<221> NAME/KEY: MISC_FEATURE
<222> LOCATION: (1)..(205)
<223> OTHER INFORMATION: FlagV1PDSB

<400> SEQUENCE: 34

```
Gln Val Lys Leu Glu Glu Ser Gly Gly Gly Leu Val Gln Ala Gly Gly
  1               5                  10                  15

Ser Arg Arg Leu Ser Cys Ala Thr Ser Gly Leu Thr Phe Arg Asn Phe
                 20                  25                  30

His Met Ala Trp Phe Arg Gln Val Ala Gly Lys Glu Arg Glu Val Val
             35                  40                  45

Cys Ala Ile Ser Trp Ser Arg Asp Arg Gln Tyr Tyr Pro Asp Pro Val
 50                  55                  60

Lys Gly Arg Phe Thr Cys Thr Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Arg Thr Ala Ser Ala Ser Gly Asp Trp Tyr Lys Gly Ser Tyr
            100                 105                 110

Gln Tyr Trp Gly Gln Gly Thr Gln Val Thr Val Ser Ser Gly Pro Gly
            115                 120                 125

Gly Gly Ser Gly Gly Gly Ser Thr Pro Asp Cys Val Thr Gly Lys
            130                 135                 140

Val Glu Tyr Thr Lys Tyr Asn Asp Glu Asp Thr Phe Thr Val Lys Val
145                 150                 155                 160

Gly Asp Lys Glu Leu Phe Thr Asn Arg Ala Asn Leu Gln Ser Leu Leu
            165                 170                 175

Leu Ser Ala Gln Ile Thr Gly Met Thr Val Thr Ile Lys Thr Asn Ala
            180                 185                 190

Cys His Asn Gly Gly Phe Ser Glu Val Ile Phe Arg
            195                 200                 205

<210> SEQ ID NO 35
<211> LENGTH: 205
<212> TYPE: PRT
<213> ORGANISM: Lama glama
<220> FEATURE:
<221> NAME/KEY: MISC_FEATURE
<222> LOCATION: (1)..(205)
<223> OTHER INFORMATION: FlagV1F23PDSB

<400> SEQUENCE: 35

Gln Val Gln Leu Val Glu Ser Gly Gly Gly Leu Val Gln Ala Gly Gly
  1               5                  10                  15

Ser Arg Arg Leu Ser Cys Ala Thr Ser Gly Leu Thr Phe Arg Asn Phe
                 20                  25                  30

His Met Ala Trp Phe Arg Gln Val Ala Gly Lys Glu Arg Glu Val Val
             35                  40                  45

Cys Ala Ile Ser Trp Ser Arg Asp Arg Gln Tyr Tyr Pro Asp Pro Val
 50                  55                  60

Lys Gly Arg Phe Thr Cys Thr Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Arg Thr Ala Ser Ala Ser Gly Asp Trp Tyr Lys Gly Ser Tyr
            100                 105                 110

Gln Tyr Trp Gly Gln Gly Thr Gln Val Thr Val Ser Ser Gly Pro Gly
            115                 120                 125

Gly Gly Ser Gly Gly Gly Ser Thr Pro Asp Cys Val Thr Gly Lys
            130                 135                 140
```

Val Glu Tyr Thr Lys Tyr Asn Asp Glu Asp Thr Phe Thr Val Lys Val
145                 150                 155                 160

Gly Asp Lys Glu Leu Phe Thr Asn Arg Ala Asn Leu Gln Ser Leu Leu
            165                 170                 175

Leu Ser Ala Gln Ile Thr Gly Met Thr Val Thr Ile Lys Thr Asn Ala
        180                 185                 190

Cys His Asn Gly Gly Phe Ser Glu Val Ile Phe Arg
    195                 200                 205

<210> SEQ ID NO 36
<211> LENGTH: 208
<212> TYPE: PRT
<213> ORGANISM: Lama glama
<220> FEATURE:
<221> NAME/KEY: MISC_FEATURE
<222> LOCATION: (1)..(208)
<223> OTHER INFORMATION: FlagV6PDSB

<400> SEQUENCE: 36

Gln Val Lys Leu Glu Glu Ser Gly Gly Gly Leu Val Gln Ala Gly Gly
1               5                   10                  15

Ser Leu Arg Val Ser Cys Thr Ala Ser Val Ser Thr Phe Ser Ile Asn
            20                  25                  30

Ala Leu Gly Trp Tyr Arg Gln Ala Pro Gly Lys Ala Arg Glu Leu Val
        35                  40                  45

Cys Ala Ile Gly Ser Asp Gly Thr Val Tyr Tyr Thr Asp Ser Val Lys
    50                  55                  60

Gly Arg Phe Thr Cys Ser Arg Asp Asn Ala Lys Asn Thr Val Ser Leu
65                  70                  75                  80

Gln Met Ser Ser Leu Lys Pro Glu Asp Thr Ala Val Tyr Tyr Cys Asn
                85                  90                  95

Ala Ala Gly Lys Arg Ile Gly Ser Asp Gly Ser Ile Trp Phe Ala Val
            100                 105                 110

Ala Ser Phe Gly Ser Trp Gly Gln Gly Thr Gln Val Thr Val Ser Ser
        115                 120                 125

Gly Pro Gly Gly Gly Ser Gly Gly Gly Ser Thr Pro Asp Cys Val
130                 135                 140

Thr Gly Lys Val Glu Tyr Thr Lys Tyr Asn Asp Glu Asp Thr Phe Thr
145                 150                 155                 160

Val Lys Val Gly Asp Lys Glu Leu Phe Thr Asn Arg Ala Asn Leu Gln
            165                 170                 175

Ser Leu Leu Leu Ser Ala Gln Ile Thr Gly Met Thr Val Thr Ile Lys
        180                 185                 190

Thr Asn Ala Cys His Asn Gly Gly Phe Ser Glu Val Ile Phe Arg
    195                 200                 205

<210> SEQ ID NO 37
<211> LENGTH: 208
<212> TYPE: PRT
<213> ORGANISM: Lama glama
<220> FEATURE:
<221> NAME/KEY: MISC_FEATURE
<222> LOCATION: (1)..(208)
<223> OTHER INFORMATION: FlagV6F23PDSB

<400> SEQUENCE: 37

Gln Val Gln Leu Val Glu Ser Gly Gly Gly Leu Val Gln Ala Gly Gly
1               5                   10                  15

Ser Leu Arg Val Ser Cys Thr Ala Ser Val Ser Thr Phe Ser Ile Asn

```
                 20                  25                  30
Ala Leu Gly Trp Tyr Arg Gln Ala Pro Gly Lys Ala Arg Glu Leu Val
             35                  40                  45

Cys Ala Ile Gly Ser Asp Gly Thr Val Tyr Tyr Thr Asp Ser Val Lys
         50                  55                  60

Gly Arg Phe Thr Cys Ser Arg Asp Asn Ala Lys Asn Thr Val Ser Leu
 65                  70                  75                  80

Gln Met Ser Ser Leu Lys Pro Glu Asp Thr Ala Val Tyr Tyr Cys Asn
                 85                  90                  95

Ala Ala Gly Lys Arg Ile Gly Ser Asp Gly Ser Ile Trp Phe Ala Val
            100                 105                 110

Ala Ser Phe Gly Ser Trp Gly Gln Gly Thr Gln Val Thr Val Ser Ser
            115                 120                 125

Gly Pro Gly Gly Ser Gly Gly Gly Ser Thr Pro Asp Cys Val
            130                 135                 140

Thr Gly Lys Val Glu Tyr Thr Lys Tyr Asn Asp Glu Asp Thr Phe Thr
145                 150                 155                 160

Val Lys Val Gly Asp Lys Glu Leu Phe Thr Asn Arg Ala Asn Leu Gln
            165                 170                 175

Ser Leu Leu Leu Ser Ala Gln Ile Thr Gly Met Thr Val Thr Ile Lys
            180                 185                 190

Thr Asn Ala Cys His Asn Gly Gly Gly Phe Ser Glu Val Ile Phe Arg
            195                 200                 205

<210> SEQ ID NO 38
<211> LENGTH: 24
<212> TYPE: DNA
<213> ORGANISM: Artificial Sequence
<220> FEATURE:
<223> OTHER INFORMATION: Portion of the pMED6 vector

<400> SEQUENCE: 38
ggccaggccg gccaggcata gact                                            24

<210> SEQ ID NO 39
<211> LENGTH: 375
<212> TYPE: DNA
<213> ORGANISM: Lama glama
<220> FEATURE:
<221> NAME/KEY: misc_feature
<222> LOCATION: (1)..(375)
<223> OTHER INFORMATION: FlagV1M

<400> SEQUENCE: 39
caggtaaagc tggaggagtc tgggggagga ttggtgcagg ctgggggctc tcggagactc      60
tcctgtgcaa cctctggtct cacatttagg aattttcaca tggcatggtt ccgccaggtc    120
gccgggaagg agcgtgaggt agtggcagct atttcctgga gtagagatag acagtattat    180
ccagatcccg tgaagggccg attcaccatc accagagaca cgccaagaa cacggtgtat     240 ctgcagatga acagcctgaa acctgaggac acggccgttt attactgtgc tgcaagaaca    300
gcgtccgcat ctggtgactg gtataaggga tcgtatcaat actggggcca ggggacccag    360
gtcaccgtct cctca                                                    375

<210> SEQ ID NO 40
<211> LENGTH: 375
<212> TYPE: DNA
<213> ORGANISM: Lama glama
<220> FEATURE:
```

```
<221> NAME/KEY: misc_feature
<222> LOCATION: (1)..(375)
<223> OTHER INFORMATION: FlagV1F23M

<400> SEQUENCE: 40
caggtgcagc tggtggagtc tgggggagga ttggtgcagg ctgggggctc tcggagactc      60
tcctgtgcaa cctctggtct cacatttagg aattttcaca tggcatggtt ccgccaggtc     120
gccgggaagg agcgtgaggt agtggcagct atttcctgga gtagagatag acagtattat     180
ccagatcccg tgaagggccg attcaccatc accagagaca acgccaagaa cacggtgtat     240
ctgcagatga acagcctgaa acctgaggac acggccgttt attactgtgc tgcaagaaca     300
gcgtccgcat ctggtgactg gtataaggga tcgtatcaat actggggcca ggggacccag     360
gtcaccgtct cctca                                                      375

<210> SEQ ID NO 41
<211> LENGTH: 375
<212> TYPE: DNA
<213> ORGANISM: Lama glama
<220> FEATURE:
<221> NAME/KEY: misc_feature
<222> LOCATION: (1)..(375)
<223> OTHER INFORMATION: FlagV1MDSB

<400> SEQUENCE: 41
caggtaaagc tggaggagtc tgggggagga ttggtgcagg ctgggggctc tcggagactc      60
tcctgtgcaa cctctggtct cacatttagg aattttcaca tggcatggtt ccgccaggtc     120
gccgggaagg agcgtgaggt agtgtgcgct atttcctgga gtagagatag acagtattat     180
ccagatcccg tgaagggccg attcacctgc accagagaca acgccaagaa cacggtgtat     240
ctgcagatga acagcctgaa acctgaggac acggccgttt attactgtgc tgcaagaaca     300
gcgtccgcat ctggtgactg gtataaggga tcgtatcaat actggggcca ggggacccag     360
gtcaccgtct cctca                                                      375

<210> SEQ ID NO 42
<211> LENGTH: 375
<212> TYPE: DNA
<213> ORGANISM: Lama glama
<220> FEATURE:
<221> NAME/KEY: misc_feature
<222> LOCATION: (1)..(375)
<223> OTHER INFORMATION: FlagV1F23MDSB

<400> SEQUENCE: 42
caggtgcagc tggtggagtc tgggggagga ttggtgcagg ctgggggctc tcggagactc      60
tcctgtgcaa cctctggtct cacatttagg aattttcaca tggcatggtt ccgccaggtc     120
gccgggaagg agcgtgaggt agtgtgcgct atttcctgga gtagagatag acagtattat     180
ccagatcccg tgaagggccg attcacctgc accagagaca acgccaagaa cacggtgtat     240
ctgcagatga acagcctgaa acctgaggac acggccgttt attactgtgc tgcaagaaca     300
gcgtccgcat ctggtgactg gtataaggga tcgtatcaat actggggcca ggggacccag     360
gtcaccgtct cctca                                                      375
```